(12) United States Patent
Bonini et al.

(10) Patent No.: US 7,416,848 B2
(45) Date of Patent: *Aug. 26, 2008

(54) DNA ENCODING SNORF25 RECEPTOR

(75) Inventors: James A. Bonini, Oakland, NJ (US);
Beth E. Borowsky, Montclair, NJ (US);
Nika Adham, Ridgewood, NJ (US);
Noel Boyle, Cliffside Park, NJ (US);
Thelma O. Thompson, Passaic Park, NJ (US)

(73) Assignee: H. Lundbeck A/S, Valby/Copenhagen (DK)

( * ) Notice: Subject to any disclaimer, the term of this patent is extended or adjusted under 35 U.S.C. 154(b) by 850 days.

This patent is subject to a terminal disclaimer.

(21) Appl. No.: 10/278,437

(22) Filed: Oct. 22, 2002

(65) Prior Publication Data

US 2003/0139590 A1 Jul. 24, 2003

Related U.S. Application Data

(63) Continuation-in-part of application No. 09/641,259, filed on Aug. 17, 2000, now Pat. No. 6,468,756, which is a continuation-in-part of application No. PCT/US00/04413, filed on Feb. 22, 2000, which is a continuation of application No. 09/387,699, filed on Aug. 13, 1999, now Pat. No. 6,221,660, which is a continuation-in-part of application No. 09/255,376, filed on Feb. 22, 1999, now abandoned.

(51) Int. Cl.
*G01N 33/53* (2006.01)
*C07K 14/705* (2006.01)
*C07H 21/04* (2006.01)

(52) U.S. Cl. .................. 435/7.1; 435/7.2; 435/325; 435/348; 435/357; 435/361; 435/356; 435/365; 435/369; 435/354; 530/350; 536/23.5

(58) Field of Classification Search .............. None
See application file for complete search history.

(56) References Cited

U.S. PATENT DOCUMENTS 6,221,660 B1 4/2001 Bonini et al.
6,468,756 B1 10/2002 Bonini et al.
2003/0017528 A1* 1/2003 Chen et al. ............. 435/69.1
2003/0139590 A1 7/2003 Bonini et al.

FOREIGN PATENT DOCUMENTS

| WO | 9325677 | 12/1993 |
|---|---|---|
| WO | 0022131 | 4/2000 |
| WO | 0031258 | 6/2000 |
| WO | WO0050562 | 8/2000 |
| WO | 0142288 | 6/2001 |

OTHER PUBLICATIONS

GenEMBL Database Accession No. AC002537, Birren, B., et al., "Homo sapiens chromosome 17, clone hRPC864M4," published Apr. 18, 1998.
GenEMBL Database Accession No. AF017283, Hauer, D.A., et al., "Direct Submission," published Sep. 18, 1997.
GenEMBL Database Accession No. AL035423, A. Pearce, "Direct Submission," published Nov. 23, 1999.

* cited by examiner

*Primary Examiner*—Eileen B. O'Hara
(74) *Attorney, Agent, or Firm*—Stephen G. Kalinchak; Margaret M. Buck

(57) ABSTRACT

This invention provides isolated nucleic acids encoding mammalian SNORF25 receptors, purified mammalian SNORF25 receptors, vectors comprising nucleic acid encoding mammalian SNORF25 receptors, cells comprising such vectors, antibodies directed to mammalian SNORF25 receptors, nucleic acid probes useful for detecting nucleic acid encoding mammalian SNORF25 receptors, antisense oligonucleotides complementary to unique sequences of nucleic acid encoding mammalian SNORF25 receptors, transgenic, nonhuman animals which express DNA encoding normal or mutant mammalian SNORF25 receptors, methods of isolating mammalian SNORF25 receptors, methods of treating an abnormality that is linked to the activity of the mammalian SNORF25 receptors, as well as methods of determining binding of compounds to mammalian SNORF25 receptors, methods of identifying agonists and antagonists of SNORF25 receptors, and agonists and antagonists so identified.

14 Claims, 20 Drawing Sheets

FIGURE 1A

```
  1  TGAGAATTTCAGCTGGAGAGATAGCATGCCCTGGTAAGTGAAGTCCTGCCACTTCGAGAC   60
 61  ATGGAATCATCTTTCTCATTTGGAGTGATCCTTGCTGTCCTGTGCTGTGTTGATCCACAAGAATGATGGTGTCAGT  120
```

```
  1  TGAGAATTTCAGCTGGAGAGATAGCATGCCCTGGTAAGTGAAGTCCTGCCACTTCGAGAC   60
 61  ATGGAATCATCTTTCTCATTTGGAGTGATCCTTGCTGTCCTGTGCTGTGTTGATCCACAAGAATGATGGTGTCAGT  120
121  ACTAACACACTAGTGGCTGTGTGGCTGTGTGGCTGACACCTTGATTGGTGTGGCCATCTCTGGC  180
181  CTCTGCTTCACCTTGAATCTGGCTCCCTTCTCCAGCTCTCCAGACCAGCTCTGTGCCACAGAAGACCCTGTGCAGCCTG  240
241  CTACTCACAGACCAGCTCTGTCACTTCCCTGCCTCTGTCCTCACGGTCATGCTGATCACC  300
301  CGGATGGCATTGTCCATCAAGCAGCCCTTCCGCTACTTGAAGATCATGAGTGGGTTC  360
361  TTTGACAGGTACCTTGCCATTGCCGGGCTGTGGTAGTGTCTTACCTCATTGGCTTCCTCCCA  420
421  GTGGCCCGGGCCTGCATTGCCGGGCTGTGTTAGTGTCTTACCTCATTGGCTTCCTCCCA  480
481  CTCGGAATCCCCCATGTTCCAGCAGACTGCCTACAAAGGGCAGTGCAGCTTCTTTGCTGTA  540
541  TTTCACCCTCACTTCGTGTGCTGACCCTCTCCCTGCGTTGGCTTCTTCCCAGCCATGCTCCTC  600
```

FIGURE 1B

```
601   TTTGTCTCTTCTACTGCGACATGCTCAAGATTGCCTCCATGCACAGCCAGCAGATTCGA   660
661   AAGATGGAACATGCAGGAGCCATGGCTGGAGGTTATCGATCCCCACGGACTCCCAGCGAC   720
721   TTCAAAGCTCTCCGTACTGTGTCTGTTCTCATTGGGAGCTTTGCTCTATCCTGGACCCCC   780
781   TTCCTTATCACTGGCATTGTGCAGGTGGCCTGCCAGGAGTGTCACCTCTACCTAGTGCTG   840
841   GAACGGGTACCTGTGGCTCGCGCTGGGCAACTCCCTGCTCAACCCACTCATCTATGCC    900
901   TATTGGCAGAAGGAGGTGCGACTGCAGCTCTACCACATGCCCCTAGGAGTGAAGAAGGTG   960
961   CTCACCTCATTCCCTCCTCTTTCTCTCGGGCCAGGAATTGTGGCCCAGAGAGGGCCCAGGGAA  1020
1021  AGTTCCTGTCACATCGTCACTATCTCCAGCTCAGAGTTTGATGGCTAAGACGGTAAGGGC  1080
1081  AGAGAAGTTTCAAAGTGCCTTTCTCCTCCCACTCTGGAGCCCCAACTAG            1129
```

```
1    TCAAGACCCAGCATGCCCCTTATAAGTGGGAGTCCTGCTACCTCGAACCATGGAGTCATCT    60
61   TTCTCATTGGAGTGATCCTTGCTGTCCTGACCATCCTTATCATTGCTGTTAATGCGCTG    120
121  GTGGTTGTGGCTATGCTGCTATCAATCTACAAGAATGATGGTGTTGGCCCTTTGCTTCACC   180
181  TTAAATCTGGCCCGTGGCTGATACCTTGATTGGCCGTGGCTATTTCTGGGCTAGTTACAGAC   240
241  CAGCTCTCCAGCTCTGCTCAGCACACAGAAGACCTTGTGTAGCCTTCGATGGCATTC       300
301  GTCACTTCTTCTGCAGCCGCCTCTGTCCTCACGTCGTCATGCTGATTGCCTTTGACAGGTAC  360
361  CTGGCCATTAAGCAGCCCCTCGTTGGTTGATATCTTACCTTATCGGCTTCCTCCCACTTGGAGTCTCC 420
421  TGCATTGCAGGGCTGTGGTTGATATCTTACCTTATCGGCTTCCTCCCACTTGGAGTCTCC    480
481  ATATTCCAGCAGACCAGCCACCTACCATGGGCCCTGCCACCTTCTTTGCTGTGTTTCACCCAAGG 540
541  TTTGTGCTGACCCTCTCCTGGCTTCCCCAGCTGTGCTCCTCTTTGTCTTCTTC          600
601  TACTGTGACATGCTCAAGATTGCCTCTGTGCACAGCCAGCACATCCGGAAGATGGAACAT   660
```

FIGURE 3B

```
661   GCAGGAGCCATGGTTGGAGCTTGCCGGCCCCCACGGCCTGTCAATGACTTCAAGGCTGTC   720
721   CGGACTGTATCTGTCCTTATTGGGAGCTTCACCCTGTCCTGGTCTCCGTTTCTCATCACT   780
781   AGCATTGTGCAGGTGGCCTGCCACAAATGCTGCCTCTACCAAGTGCTGGAAAAATACCTC   840
841   TGGCTCCCTTGGAGTTGGCAACTCCCTGCTCAACCCACTCATCTATGCCTATTGGCAGAGG   900
901   GAGGTTCGGCAGCAGCTCTGCCACATGGCCCTGGGGGTGAAGAAGTTCTTTACTTCAATC   960
961   TTCCTCCTTCTCTCGGCCAGGAATCGTGGTCCACAGAGGACCCGAGAAAGCTCCTATCAC   1020
1021  ATCGTCACTATCAGCCAGCCGGAGCTCGATGGCTAGGATGGTAAGGAATGGATGTTTCCA   1080
1081  AG                                                             1082
```

Effect of ATRA on cAMP release in Cos-7 cells transfected with various cyclase stimulatory receptors

SNORF25 + CFTR

ATRA

CFTR alone

ATRA 200 nA 100 s

B2AR + CFTR

Epi

FIGURE 13A

```
  1  AGTGGAAGTGCTGCTACCTCACCATGGAGTCATCCTTCTCATTGGAGTGATCCTTGCTG    60
 61  TCCTAACCATCCTCATCATTGCTGTGTAATGCACTGGTAGTTGTGGCTATGCTGCTATCAA  120
121  TCTACAAGAATGATGGTGTTGGCCTTTGCTTCACCTTGAATCTGGCCGTGGCTGATACCT  180
181  TGATTGGCGTGGCTATTTCTGGTCTAGTTACAGACCAGCTCTCCAGCTCTGCTCAGCATA  240
241  CACAGAAGACCTTGTGTAGCCTTCGGATGGCATTTGTCACTTCTTCTGCAGCTGCCTCTG  300
301  TCCTCACCGTCATGCTGATTGCCTTTGACAGATACCTTGCCATTAAGCAGCCCCTCCGTT  360
361  ACTTCCAGATCATGAATGGGCTTGTGCTGGAGCATGCATTGCAGGACTGTGGTTGGTAT  420
421  CTTACCTTATCGGCTTCCTCCCCACTCGGAGTCTCCATATTCCAGCAGACCACCTACCATG  480
481  GACCCTGCAGCTTCTTTGCTGTGTTCACCCAAGGTTTGTGCTGACCCTCTCCTGTGCTG  540
541  GCTTCTTCCCAGCTGTGCTCCTCTTTGTCTTCTTCTACTGTGACATGCTCAAGATTGCCT  600
601  CTGTGCACAGCCAGCAGATCCGGAAGATGAACATGCAGGAGCCATGGGCCGGAGCTTATC  660
661  GGCCCCCACGGTCTGTCAATGACTTCAAGGCTGTGTTCGTACTATAGCTGTTCTTATTGGGA  720
```

FIGURE 13B

```
721  GCTTCACTCTGTCCCTGGTCTCCCCTTTCTCATAACTAGCATTGTGCAGGTGGCCTGCCACA  780
781  AATGCTGCCTTTACCAAGTGCTGGAAAAGTACCTGTGGCTCCTTGGAGTTGGCAACTCCC   840
841  TACTCAACCCACTCATCTATGCCTATTGGCAGAGGGAGGTTCGGCAGCAGCTCTACCACA    900
901  TGGCCCTGGGAGTGAAAAAGTTCTTCACTTCAATCCTCCTCCTTCCCAGCCAGGAATC     960
961  GTGGTCCAGAGAGGACCAGAGAAAGCGCCTATCACATCGTCACTATCAGCCATCCGGAGC  1020
1021 TCGATGGCTAAGACGGTAAGGAAGGAATGTTTCAAA                          1056
```

DNA ENCODING SNORF25 RECEPTOR

This application is a continuation-in-part of U.S. Ser. No. 09/641,259, filed Aug. 17, 2000, now U.S. Pat. No. 6,468,756, which claims priority of PCT International Application Ser. No. PCT/US00/04413, filed Feb. 22, 2000, which claims priority of U.S. Ser. No. 09/387,699, filed Aug. 13, 1999, now U.S. Pat. No. 6,221,660, issued on Apr. 24, 2001, which is a continuation-in-part of U.S. Ser. No. 09/255,376, filed Feb. 22, 1999, now abandoned, the contents of which are hereby incorporated by reference.

BACKGROUND OF THE INVENTION

Throughout this application various publications are referred to by partial citations within parentheses. Full citations for these publications may be found at the end of the specification immediately preceding the claims. The disclosures of these publications, in their entireties, are hereby incorporated by reference into this application in order to more fully describe the state of the art to which the invention pertains.

Neuroregulators comprise a diverse group of natural products that subverse or modulate communication in the nervous system. They include, but are not limited to, neuropeptides, amino acids, biogenic amines, lipids, and lipid metabolites, and other metabolic byproducts. Many of these neuroregulator substances interact with specific cell surface receptors, which transduce signals from the outside to the inside of the cell. G-protein coupled receptors (GPCRs) represent a major class of cell surface receptors with which many neurotransmitters interact to mediate their effects. GPCRs are characterized by seven membrane-spanning domains and are coupled to their effectors via G-proteins linking receptor activation with intracellular biochemical sequelae such as stimulation of adenylyl cyclase.

Vitamin $A_1$ (all-trans-retinol) is oxidized to vitamin $A_1$ aldehyde (all-trans-retinal) by an alcohol dehydrogenase. All-trans-retinal is critical for the synthesis of rhodopsin in retinal cells, where it plays a key role in the visual system. All-trans-retinal can also be converted to all-trans-retinoic acid (ATRA) by aldehyde dehydrogenase and oxidase in other cell types (Bowman, W. C. and Rand, M. J., 1980).

Historically, ATRA and the other active metabolites of vitamin A, 9-cis-retinoic acid (9CRA), were thought to only mediate their cellular effects through the action of nuclear retinoic acid receptors (RARα, β, γ) and retinoid X receptors (RXRα, β, γ) (Mangelsdorf, D. J., et al, 1994). These receptors are members of a superfamily of ligand-dependent transcription factors, which include the vitamin D receptor (VDR), thyroid hormone receptor (TR), and peroxisome proliferator activator receptors (PPAR). They form heterodimers and homodimers that bind to DNA response elements in the absence of ligand. In response to ligand binding the dimer changes conformation which leads to transactivation and regulation of transcription of a set(s) of cell type-specific genes (Mangelsdorf, D. J., et al, 1994; Hofman, C. and Eichele, G., 1994; and Gudas, L. J. et al, 1994).

Since retinoic acid produces a wide variety of biological effects, it is not surprising that it is proposed to play an important role in various physiological and pathophysiological processes. Retinoids control critical physiological events including cell growth, differentiation, reproduction, metabolism, and hematopoiesis in a wide variety of tissues. At a cellular level, retinoids are capable of inhibiting cell proliferation, inducing differentiation, and inducing apoptosis (Breitman, T. et al, 1980; Sporn, M. and Roberts, A., 1984, and Martin, S., et al, 1990). These diverse effects of retinoid treatment prompted a series of investigations evaluating retinoids for cancer chemotherapy as well as cancer chemoprevention. Clinically, retinoids are used for the treatment of a wide variety of malignant diseases including: acute promyelocytic leukemia (APL), cutaneous T-cell malignancies, dermatological malignancies, squamous cell carcinomas of skin and of the cervix and neuroblastomas (Redfern, C. P. et al, 1995 for review). Retinoids have also been examined for their ability to suppress carcinogenesis and prevent development of invasive cancer. 13-cis retinoic acid reverses oral leukoplakia, the most common premalignant lesion of the aerodigestive tract, and is also used in the chemoprevention of bladder cancer (Sabichi, A. L. et al, 1998, for review). Also, 13-cis retinoic acid treatment as adjuvant therapy after surgery and radiation in head and neck cancer caused a significant delay in the occurrence of second primary cancers (Gottardis, M. M. et al, 1996, for review).

Interestingly, retinoids also have an effect on pancreatic function. It has been demonstrated that retinoic acid (or retinol) is required for insulin secretion from isolated islets (Chertow, B. S., et al, 1987) and from RINm5F rat insulinoma cells (Chertow, B. S., et al, 1989). Retinoic acid may also have an effect on cell-to-cell adhesion and aggregation (Chertow, B. S., et al, 1983). In addition, a single intragastric administration of 9CRA (but not ATRA) induced a wave of DNA synthesis in the pancreatic acinar cells and in the proximal tubular epithelial cells of the kidneys (Ohmura, T., et al, 1997). Therefore, retinoic acid could play a role in the normal pancreatic function and possibly in the development of diabetes. There is also some evidence that retinoids could be useful in the treatment of pancreatic malignancies (El-Metwally, T. H. et al, 1999; Rosenwicz, S. et al, 1997; and Rosenwicz, S. et al, 1995).

Retinoids have been shown to affect epidermal cell growth and differentiation as well as sebaceous gland activity and exhibit immunomodulatory and anti-inflammatory properties. Therefore, retinoids have been increasingly used for treatment of a variety of skin disorders including: psoriasis and other hyperkeratotic and parakeratotic skin disorders, keratotic genodermatosis, severe acne and acne-related dermatoses, and also for therapy and/or chemoprevention of skin cancer and other neoplasia (Orfanos, C. E., et al, 1997 for review).

Retinoids are also involved in lung development. Fetal lung branching leading to development of the alveolar tree is accelerated by retinoic acid. Currently, prematurely delivered infants who have immature lungs are treated with vitamin A, but other applications may exist that require further investigation (Chytil, F., 1996).

Lastly, there is some evidence that suggests that retinoids may play a role in schizophrenia (Goodman, A. B. 1998) and Alzheimer's disease (Connor, M. J. and Sidell, N., 1997).

The extensive list of retinoid-mediated effects indicate that retinoic acid receptors (non-nuclear) are attractive as targets for therapeutic intervention for several disorders and would be useful in developing drugs with higher specificity and fewer side effects for a wide variety of diseases.

Platelet-Activating Factor (PAF) is a lipid mediator with multitude of physiological and pathophysiological effects. Originally recognized as a 'soluble factor' responsible for serotonin secretion (Henson, 1970), its chemical identity was revealed in 1979 when Demopoulos et al. demonstrated that a semisynthetic phospholipid 1-O-alkyl-2-acetyl-sn-glycero-3-phosphocholine had properties identical to PAF. Naturally-occurring PAF is in fact a mixture of phospholipids containing the alkyl side chains of varying lengths. The exact composition of naturally-occuring PAF is dependent on the site of biosynthesis. A wide variety of cells, such as leukocytes, neutrophils, endothelial cells, platelets and macrophages, can synthesize PAF (Chao and Olson, 1993).

PAF can be generated via two pathways: de novo and remodeling pathways (Maclennan et al., 1996). The precursor in the de novo pathway is 1-alkyl-2-lyso-sn-glycero-3-phosphate which is, several enzymatic steps later, converted to PAF. Alternatively, in the remodeling pathway, PAF is synthesized from 1-alkyl-2-acyl-sn-glycero-3-phosphocholine via the actions of the enzymes phospholipase $A_2$ ($PLA_2$) and acetyltransferase. The intermediates in this pathway are free polyunsaturated fatty acid, such as arachidonic acid, and lyso-PAF. A critical difference between the de novo and remodeling pathways is that, while the former pathway may be responsible for physiological levels of PAF, the latter pathway is believed to be activated only upon stimulation of cells leading to abnormally high levels of PAF. Some of the potent stimuli for PAF secretion involve thrombin, bradykinin and tumor necrosis factor. Additionally, PAF itself can enhance its own synthesis and secretion.

PAF binding has been observed in numerous cell types, suggesting that specific PAF receptors exist in different cells (Chao and Olson, 1993). Platelets from several species exhibit high affinity binding sites for [$^3$H]-PAF with the $K_d$ values ranging from 0.5 nM to 37 nM. In contrast, rat platelets show only nonspecific binding to [$^3$H]-PAF, perhaps explaining the lack of platelet aggregating response to PAF in these cells (Sanchez-Crespo et al., 1981). Specific binding sites for [$^3$H]-PAF are also present on smooth muscle cells, leukocytes, macrophages, and Kupffer cells (Chao et al., 1989; Hwang et al., 1983; Ng and Wong, 1988; Valone, 1988). The [$^3$H]-PAF binding on human neutrophils reveals two binding sites, a high affinity site with the $K_d$ value of 0.2 nM and a low affinity site with the $K_d$ value of 500 nM (Chao and Olson, 1993). [$^3$H]-PAF binding is observed also in the CNS-associated cells such as NG108-15 cells as well as in the CNS areas such as hypothalamus and cerebral cortex (Chau et al., 1992; Hosford et al., 1990; Junier et al., 1988; Marcheselli et al., 1990). Interestingly, high affinity sites on rat cerebral cortex correspond to intracellular sites on microsomal membranes while the low affinity site is present on the plasma membrane (Marcheselli et al., 1990).

PAF produces a diverse array of intracellular actions. Several cell types release arachidonic acid in response to PAF stimulation. This action of PAF may involve the heterotrimeric G-protein and $PLA_2$ since it is blocked by pertussis toxin and the $PLA_2$ inhibitors (Nakashima et al., 1989). Importantly, some physiological actions of PAF are mediated through arachidonic acid metabolites such as leukotrienes and prostaglandins. For example, PAF induced coronary vasoconstriction in the isolated perfused rat heart through the release of $LTC_4$ (Piper and Stewart, 1986). Similarly, PAF-mediated pulmonary vasoconstriction and edema in isolated lungs were accompanied by increased $LTC_4$ and $LTD_4$ levels in the lung effluent perfusate (Voelkel et al., 1982). In addition to arachidonic release, PAF also induces phosphoinositide turnover and increase in intracellular calcium in a wide variety of cells such as platelets, neutrophils and macrophages (Chao and Olson, 1993). Hydrolysis of phosphatidylinositol 4,5-bisphosphate may involve a specific phospholipase C, leading to formation of two second messengers, inositol 1,4,5-triphosphate and diacylglycerol. Prpic et al. (1988) demonstrated that PAF-induced increase in intracellular calcium in macrophages was the result of inositol phosphate generation. However, in rabbit platelets, PAF induces elevation of intracellular calcium via influx of extracellular calcium through calcium channels since the calcium channel blocker could block the PAF action (Lee et al., 1981; Lee et al., 1983). Other biochemical effects of PAF include stimulation of tyrosine phosphorylation of cellular proteins and induction of immediate early genes such as c-fos and c-jun (Chao and Olson, 1993).

Several studies have linked the PAF binding and signaling to the heterotrimeric G-proteins. PAF stimulated GTPase activity in platelets, and GTP caused a shift in PAF binding (Shukla, 1992). Additionally, injection of an inactive GTP analogue reduced PAF-induced chloride current in oocytes (Shimizu et al., 1992). These evidences suggested that PAF might produce its cellular effects via a GPCR. This was confirmed upon cloning of a PAF receptor from guinea pig lungs in 1991 (Honda et al., 1991). This receptor and its species homologues are predicted to have seven transmembrane-spanning regions and contain several highly conserved amino acids present in other GPCRs (Bito et al., 1994; Honda et al., 1991; Nakamura et al., 1991). In a heterologous expression system, the PAF receptor activates primarily the Gq family of G-proteins, although the stimulation of Gi class of G-proteins has also been suggested (Honda et al., 1994).

Through the cloned PAF receptor and possibly through as yet unidentified other PAF receptors, PAF produces a diverse array of physiological and pathophysiological effects. As the name suggests, PAF is a potent activator of platelet aggregation in many species, the notable exception being rat platelets, and enhances secretion of thromboxanes from platelets (Chao and Olson, 1993). It also stimulates aggregation of monocytes and leukocytes (Ford-Hutchinson, 1983; Yasaka et al., 1982), synthesis of leukotrienes from leukocytes (Gorman et al., 1983), and degranulation of eosinophils (Bartemes et al., 1999). In addition, it behaves as a chemotactic factor for several cell types such as monocytes and eosinophils (Del Sorbo et al., 1999; Liu et al., 1998). When injected intravenously, it can cause thrombocytopenia and leukopenia (Demopoulos et al., 1981).

PAF has potent effects on cardiovascular parameters. When given systemically, it causes vasodilation and hypotension (Handa et al., 1990; Yamanaka et al., 1992). However, its effect on coronary and pulmonary circulations is dependent on the dose (Goldstein et al., 1986). It also increases vascular permeability, allowing plasma extravasation. When infused into the carotid artery, PAF causes a decrease in cerebral blood flow (Kochanek et al., 1988). Similarly, PAF administration reduces spinal cord blood flow (Faden and Holt, 1992). These effects of PAF are independent of any direct action on cerebral vasculature, but may be the result of the change in blood-brain barrier (Kumar et al., 1988). PAF contracts other smooth muscles such as gastrointestinal, uterine and pulmonary smooth muscles directly as well as via release of other mediators (Martinez-Cuesta et al., 1996; Pritze et al., 1991; Zhu et al., 1992). It also contracts the airway smooth muscle, increasing airway resistance and responsiveness to other bronchoconstrictors (Austin and Foreman, 1993; Nagase et al., 1997). This mechanism may contribute to the role of PAF in asthma.

In addition to several effects in periphery, PAF plays an important role in various CNS-associated processes (Maclennan et al., 1996). It has been suggested that PAF is involved in long-term potentiation (LTP) (Bazan, 1998). Application of PAF antagonist inhibited the development of LTP, and PAF induction of LTP prevented subsequent high-frequency stimulation-induced LTP (Del Cerro et al., 1990; Wierraszko et al., 1993). Furthermore, PAF increases glutamate release in the brain, a property expected in a retrograde messenger involved in LTP (Kato et al., 1994). Administration of PAF also modulates levels of adrenocorticotrophic hormone, beta-endorphin and corticosterone (Maclennan et al., 1996). Furthermore, PAF can regulate neuronal differentiation in cultured rat cerebral neurons and NG 108-15 cells (Kornecki and Ehrlich, 1988; Ved et al., 1991).

Due to its varied biological properties, PAF has been suggested to play a pivotal role in many pathophysiological processes, for example, inflammation and allergy, and ischemia-reperfusion injury (Maclennan et al., 1996). PAF acts directly on leukocytes as well as promotes interaction of leukocytes and endothelial cells, leading to the activation of leukocytes and release of inflammatory mediators, such as oxygen radicals, cytokines, prostaglandins and leukotrienes. Some of the inflammatory diseases that may involve PAF as a mediator are acute and chronic pancreatitis, acute renal failure, chronic bowel inflammation, Crohn's disease, ulcerative colitis, rheumatoid arthritis, psoriasis, sepsis and septic shock, cutaneous inflammation, bacterial meningitis, inflammatory bullous diseases and acute endotoxemia (Fink, 1998; Gardner et al., 1995; Heller et al., 1998; Johnson, 1999; Konturek et al., 1992; Lopez-Novoa 1999; Loucks et al., 1997; Stack and Hawkey, 1997; Zhou et al., 1990). PAF also produces pathological features characteristic of asthma (Heller et al., 1998; Page, 1992). It constricts bronchial tissue, produces tracheal and bronchial edema, stimulates secretion of mucus and causes bronchial hyperresponsiveness. PAF also produces many signs and symptoms of anaphylactic shock, suggesting its potential role in this condition (Lefort et al., 1992). Furthermore, PAF may play an important role in ischemia-reperfusion injury in various tissues such as heart and brain (Loucks et al., 1997; Maclennan et al., 1996). And finally, it has been suggested that PAF is an HIV-1-induced neurotoxin and plays a role in HIV-associated dementia (Maclennen et al., 1996).

In summary, PAF is a potent lipid mediator with a variety of biological actions. It is suggested to play a pivotal role in various pathophysiological conditions. Therefore, any ligand targeted towards altering PAF synthesis, biological actions and degradation may provide useful pharmacological therapies.

SUMMARY OF THE INVENTION

This invention provides an isolated nucleic acid encoding a mammalian SNORF25 receptor.

This invention further provides a purified mammalian SNORF25 receptor protein.

This invention also provides a vector comprising a nucleic acid in accordance with this invention.

This invention still further provides a cell comprising a vector in accordance with this invention.

This invention additionally provides a membrane preparation isolated from a cell in accordance with this invention.

Furthermore, this invention provides a nucleic acid probe comprising at least 15 nucleotides, which probe specifically hybridizes with a nucleic acid encoding a mammalian SNORF25 receptor, wherein the probe has a sequence complementary to a unique sequence present within one of the two strands of the nucleic acid encoding the mammalian SNORF25 receptor contained in plasmid pEXJT3T7-hS-NORF25 (ATCC Accession No. 203495).

This invention further provides a nucleic acid probe comprising at least 15 nucleotides, which probe specifically hybridizes with a nucleic acid encoding a mammalian SNORF25 receptor, wherein the probe has a sequence complementary to a unique sequence present within (a) the nucleic acid sequence shown in FIGS. 1A–1B (SEQ ID NO: 1) or (b) the reverse complement thereof.

This invention provides an antisense oligonucleotide having a sequence capable of specifically hybridizing to RNA encoding a mammalian SNORF25 receptor, so as to prevent translation of such RNA.

This invention further provides an antisense oligonucleotide having a sequence capable of specifically hybridizing to genomic DNA encoding a mammalian SNORF25 receptor, so as to prevent transcription of such genomic DNA.

This invention also provides an antibody capable of binding to a mammalian SNORF25 receptor encoded by a nucleic acid in accordance with this invention.

Moreover, this invention provides an agent capable of competitively inhibiting the binding of an antibody in accordance with this invention to a mammalian SNORF25 receptor.

This invention still further provides a pharmaceutical composition comprising (a) an amount of an oligonucleotide in accordance with this invention capable of passing through a cell membrane and effective to reduce expression of a mammalian SNORF25 receptor and (b) a pharmaceutically acceptable carrier capable of passing through the cell membrane.

This invention also provides a pharmaceutical composition which comprises an amount of an antibody in accordance with this invention effective to block binding of a ligand to a human SNORF25 receptor and a pharmaceutically acceptable carrier.

This invention further provides a transgenic, nonhuman mammal expressing DNA encoding a mammalian SNORF25 receptor in accordance with this invention.

This invention still further provides a transgenic, nonhuman mammal comprising a homologous recombination knockout of a native mammalian SNORF25 receptor.

This invention further provides a transgenic, nonhuman mammal whose genome comprises antisense DNA complementary to DNA encoding a mammalian SNORF25 receptor in accordance with this invention so placed within such genome as to be transcribed into antisense mRNA which is complementary to and hybridizes with mRNA encoding the mammalian SNORF25 receptor so as to reduce translation of of such mRNA and expression of such receptor.

This invention provides a process for identifying a chemical compound which specifically binds to a mammalian SNORF25 receptor which comprises contacting cells containing DNA encoding, and expressing on their cell surface, the mammalian SNORF25 receptor, wherein such cells do not normally express the mammalian SNORF25 receptor, with the compound under conditions suitable for binding, and detecting specific binding of the chemical compound to the mammalian SNORF25 receptor.

This invention further provides a process for identifying a chemical compound which specifically binds to a mammalian SNORF25 receptor which comprises contacting a membrane preparation from cells containing DNA encoding, and expressing on their cell surface, the mammalian SNORF25 receptor, wherein such cells do not normally express the mammalian SNORF25 receptor, with the compound under conditions suitable for binding, and detecting specific binding of the chemical compound to the mammalian SNORF25 receptor.

This invention still further provides a process involving competitive binding for identifying a chemical compound which specifically binds to a mammalian SNORF25 receptor which comprises separately contacting cells expressing on their cell surface the mammalian SNORF25 receptor, wherein such cells do not normally express the mammalian SNORF25 receptor, with both the chemical compound and a second chemical compound known to bind to the receptor, and with only the second chemical compound, under conditions suitable for binding of such compounds to the receptor, and detecting specific binding of the chemical compound to the mammalian SNORF25 receptor, a decrease in the binding of the second chemical compound to the mammalian SNORF25 receptor in the presence of the chemical compound being tested indicating that such chemical compound binds to the mammalian SNORF25 receptor.

This invention further provides a process involving competitive binding for identifying a chemical compound which specifically binds to a mammalian SNORF25 receptor which comprises separately contacting a membrane preparation from cells expressing on their cell surface the mammalian SNORF25 receptor, wherein such cells do not normally express the mammalian SNORF25 receptor, with both the chemical compound and a second chemical compound known to bind to the receptor, and with only the second chemical compound, under conditions suitable for binding of such compounds to the receptor, and detecting specific binding of the chemical compound to the mammalian SNORF25 receptor, a decrease in the binding of the second chemical compound to the mammalian SNORF25 receptor in the presence of the chemical compound indicating that the chemical compound binds to the mammalian SNORF25 receptor.

In an embodiment of the invention, the second compound is a lipid-like molecule including, but not limited to, ATRA and phospholipids. Examples of phospholipids include, but are not limited to, PAF(C18), PAF(C16), lyso-PAF(C18) and lyso-PAF(C16).

This invention further provides a compound identified by one of the processes of this invention.

This invention provides a method of screening a plurality of chemical compounds not known to bind to a mammalian SNORF25 receptor to identify a compound which specifically binds to the mammalian SNORF25 receptor, which comprises (a) contacting cells transfected with, and expressing, DNA encoding the mammalian SNORF25 receptor with a compound known to bind specifically to the mammalian SNORF25 receptor; (b) contacting the cells of step (a) with the plurality of compounds not known to bind specifically to the mammalian SNORF25 receptor, under conditions permitting binding of compounds known to bind to the mammalian SNORF25 receptor; (c) determining whether the binding of the compound known to bind to the mammalian SNORF25 receptor is reduced in the presence of the plurality of compounds, relative to the binding of the compound in the absence of the plurality of compounds; and if so (d) separately determining the binding to the mammalian SNORF25 receptor of each compound included in the plurality of compounds, so as to thereby identify any compound included therein which specifically binds to the mammalian SNORF25 receptor.

This invention further provides a method of screening a plurality of chemical compounds not known to bind to a mammalian SNORF25 receptor to identify a compound which specifically binds to the mammalian SNORF25 receptor, which comprises (a) contacting a membrane preparation from cells transfected with, and expressing, DNA encoding the mammalian SNORF25 receptor with the plurality of compounds not known to bind specifically to the mammalian SNORF25 receptor under conditions permitting binding of compounds known to bind to the mammalian SNORF25 receptor; (b) determining whether the binding of a compound known to bind to the mammalian SNORF25 receptor is reduced in the presence of any compound within the plurality of compounds, relative to the binding of the compound in the absence of the plurality of compounds; and if so (c) separately determining the binding to the mammalian SNORF25 receptor of each compound included in the plurality of compounds, so as to thereby identify any compound included therein which specifically binds to the mammalian SNORF25 receptor.

This invention also provides a method of detecting expression of a mammalian SNORF25 receptor by detecting the presence of mRNA coding for the mammalian SNORF25 receptor which comprises obtaining total mRNA from the cell and contacting the mRNA so obtained with a nucleic acid probe according to this invention under hybridizing conditions, detecting the presence of mRNA hybridized to the probe, and thereby detecting the expression of the mammalian SNORF25 receptor by the cell.

This invention further provides a method of detecting the presence of a mammalian SNORF25 receptor on the surface of a cell which comprises contacting the cell with an antibody according to this invention under conditions permitting binding of the antibody to the receptor, detecting the presence of the antibody bound to the cell, and thereby detecting the presence of the mammalian SNORF25 receptor on the surface of the cell.

This invention still further provides a method of determining the physiological effects of varying levels of activity of mammalian SNORF25 receptors which comprises producing a transgenic, nonhuman mammal in accordance with this invention whose levels of mammalian SNORF25 receptor activity are varied by use of an inducible promoter which regulates mammalian SNORF25 receptor expression.

This invention additionally provides a method of determining the physiological effects of varying levels of activity of mammalian SNORF25 receptors which comprises producing a panel of transgenic, nonhuman mammals in accordance with this invention each expressing a different amount of mammalian SNORF25 receptor.

Moreover, this invention provides a method for identifying an antagonist capable of alleviating an abnormality wherein the abnormality is alleviated by decreasing the activity of a mammalian SNORF25 receptor comprising administering a compound to a transgenic, nonhuman mammal according to this invention, and determining whether the compound alleviates any physiological and/or behavioral abnormality displayed by the transgenic, nonhuman mammal as a result of overactivity of a mammalian SNORF25 receptor, the alleviation of such an abnormality identifying the compound as an antagonist.

This invention also provides an antagonist identified by the preceding method.

This invention further provides a composition, e.g. a pharmaceutical composition, comprising an antagonist according to this invention and a carrier, e.g. a pharmaceutically acceptable carrier.

This invention additionally provides a method of treating an abnormality in a subject wherein the abnormality is alleviated by decreasing the activity of a mammalian SNORF25 receptor which comprises administering to the subject an effective amount of the pharmaceutical composition according to this invention so as to thereby treat the abnormality.

In addition, this invention provides a method for identifying an agonist capable of alleviating an abnormality in a subject wherein the abnormality is alleviated by increasing the activity of a mammalian SNORF25 receptor comprising administering a compound to a transgenic, nonhuman mammal according to this invention, and determining whether the compound alleviates any physiological and/or behavioral abnormality displayed by the transgenic, nonhuman mammal, the alleviation of such an abnormality identifying the compound as an agonist.

This invention further provides an agonist identified by the preceding method.

This invention still further provides a composition, e.g. a pharmaceutical composition, comprising an agonist according to this invention and a carrier, e.g. pharmaceutically acceptable carrier.

Moreover, this invention provides a method of treating an abnormality in a subject wherein the abnormality is alleviated by increasing the activity of a mammalian SNORF25 receptor which comprises administering to the subject an effective amount of the pharmaceutical composition according to this invention so as to thereby treat the abnormality.

Yet further, this invention provides a method for diagnosing a predisposition to a disorder associated with the activity of a specific mammalian allele which comprises: (a) obtaining DNA of subjects suffering from the disorder; (b) performing a restriction digest of the DNA with a panel of restriction enzymes; (c) electrophoretically separating the resulting DNA fragments on a sizing gel; (d) contacting the resulting gel with a nucleic acid probe capable of specifically hybridizing with a unique sequence included within the sequence of a nucleic acid molecule encoding a mammalian SNORF25 receptor and labeled with a detectable marker; (e) detecting labeled bands which have hybridized to the DNA encoding a mammalian SNORF25 receptor to create a unique band pattern specific to the DNA of subjects suffering from the disorder; (f) repeating steps (a)–(e) with DNA obtained for diagnosis from subjects not yet suffering from the disorder; and (g) comparing the unique band pattern specific to the DNA of subjects suffering from the disorder from step (e) with the band pattern from step (f) for subjects not yet suffering from the disorder so as to determine whether the patterns are the same or different and thereby diagnose predisposition to the disorder if the patterns are the same.

This invention also provides a method of preparing a purified mammalian SNORF25 receptor according to the invention which comprises: (a) culturing cells which express the mammalian SNORF25 receptor; (b) recovering the mammalian SNORF25 receptor from the cells; and (c) purifying the mammalian SNORF25 receptor so recovered.

This invention further provides a method of preparing the purified mammalian SNORF25 receptor according to the invention which comprises: (a) inserting a nucleic acid encoding the mammalian SNORF25 receptor into a suitable expression vector; (b) introducing the resulting vector into a suitable host cell; (c) placing the resulting host cell in suitable conditions permitting the production of the mammalian SNORF25 receptor; (d) recovering the mammalian SNORF25 receptor so produced; and optionally (e) isolating and/or purifying the mammalian SNORF25 receptor so recovered.

Furthermore, this invention provides a process for determining whether a chemical compound is a mammalian SNORF25 receptor agonist which comprises contacting cells transfected with and expressing DNA encoding the mammalian SNORF25 receptor with the compound under conditions permitting the activation of the mammalian SNORF25 receptor, and detecting any increase in mammalian SNORF25 receptor activity, so as to thereby determine whether the compound is a mammalian SNORF25 receptor agonist.

This invention also provides a process for determining whether a chemical compound is a mammalian SNORF25 receptor antagonist which comprises contacting cells transfected with and expressing DNA encoding the mammalian SNORF25 receptor with the compound in the presence of a known mammalian SNORF25 receptor agonist, under conditions permitting the activation of the mammalian SNORF25 receptor, and detecting any decrease in mammalian SNORF25 receptor activity, so as to thereby determine whether the compound is a mammalian SNORF25 receptor antagonist.

This invention still further provides a composition, for example a pharmaceutical composition, which comprises an amount of a mammalian SNORF25 receptor agonist determined by a process according to this invention effective to increase activity of a mammalian SNORF25 receptor and a carrier, for example, a pharmaceutically acceptable carrier.

Also, this invention provides a composition, for example a pharmaceutical composition, which comprises an amount of a mammalian SNORF25 receptor antagonist determined by a process according to this invention effective to reduce activity of a mammalian SNORF25 receptor and a carrier, for example, a pharmaceutically acceptable carrier.

This invention moreover provides a process for determining whether a chemical compound specifically binds to and activates a mammalian SNORF25 receptor, which comprises contacting cells producing a second messenger response and expressing on their cell surface the mammalian SNORF25 receptor, wherein such cells do not normally express the mammalian SNORF25 receptor, with the chemical compound under conditions suitable for activation of the mammalian SNORF25 receptor, and measuring the second messenger response in the presence and in the absence of the chemical compound, a change, e.g. an increase, in the second messenger response in the presence of the chemical compound indicating that the compound activates the mammalian SNORF25 receptor.

This invention still further provides a process for determining whether a chemical compound specifically binds to and inhibits activation of a mammalian SNORF25 receptor, which comprises separately contacting cells producing a second messenger response and expressing on their cell surface the mammalian SNORF25 receptor, wherein such cells do not normally express the mammalian SNORF25 receptor, with both the chemical compound and a second chemical compound known to activate the mammalian SNORF25 receptor, and with only the second chemical compound, under conditions suitable for activation of the mammalian SNORF25 receptor, and measuring the second messenger response in the presence of only the second chemical compound and in the presence of both the second chemical compound and the chemical compound, a smaller change, e.g. increase, in the second messenger response in the presence of both the chemical compound and the second chemical compound than in the presence of only the second chemical compound indicating that the chemical compound inhibits activation of the mammalian SNORF25 receptor.

In an embodiment of the invention, the second compound is a lipid-like molecule including, but not limited to, ATRA and phospholipids. Examples of phospholipids include, but are not limited to, PAF(C18), PAF(C16), lyso-PAF(C18) and lyso-PAF(C16).

Further, this invention provides a compound determined by a process according to the invention and a composition, for example, a pharmaceutical composition, which comprises an amount of a mammalian SNORF25 receptor agonist determined to be such by a process according to the invention, effective to increase activity of the mammalian SNORF25 receptor and a carrier, for example, a pharmaceutically acceptable carrier.

This invention also provides a composition, for example, a pharmaceutical composition, which comprises an amount of a mammalian SNORF25 receptor antagonist determined to be such by a process according to the invention, effective to reduce activity of the mammalian SNORF25 receptor and a carrier, for example, a pharmaceutically acceptable carrier.

This invention yet further provides a method of screening a plurality of chemical compounds not known to activate a mammalian SNORF25 receptor to identify a compound which activates the mammalian SNORF25 receptor which comprises: (a) contacting cells transfected with and expressing the mammalian SNORF25 receptor with the plurality of compounds not known to activate the mammalian SNORF25 receptor, under conditions permitting activation of the mammalian SNORF25 receptor; (b) determining whether the activity of the mammalian SNORF2S receptor is increased in the presence of one or more the compounds; and if so (c) separately determining whether the activation of the mammalian SNORF25 receptor is increased by any compound included in the plurality of compounds, so as to thereby identify each compound which activates the mammalian SNORF25 receptor.

This invention provides a method of screening a plurality of chemical compounds not known to inhibit the activation of a mammalian SNORF25 receptor to identify a compound which inhibits the activation of the mammalian SNORF2S receptor, which comprises: (a) contacting cells transfected with and expressing the mammalian SNORF25 receptor with the plurality of compounds in the presence of a known mammalian SNORF25 receptor agonist, under conditions permitting activation of the mammalian SNORF25 receptor; (b) determining whether the extent or amount of activation of the mammalian SNORF25 receptor is reduced in the presence of one or more of the compounds, relative to the extent or amount of activation of the mammalian SNORF25 receptor in the absence of such one or more compounds; and if so (c) separately determining whether each such compound inhibits activation of the mammalian SNORF25 receptor for each compound included in the plurality of compounds, so as to thereby identify any compound included in such plurality of compounds which inhibits the activation of the mammalian SNORF25 receptor.

This invention also provides a composition, for example a pharmaceutical composition, comprising a compound identified by a method according to this invention in an amount effective to increase mammalian SNORF25 receptor activity and a carrier, for example, a pharmaceutically acceptable carrier.

This invention still further provides a composition, for example, a pharmaceutical composition, comprising a compound identified by a method according to this invention in an amount effective to decrease mammalian SNORF25 receptor activity and a carrier, for example, a pharmaceutically acceptable carrier.

Furthermore, this invention provides a method of treating an abnormality in a subject wherein the abnormality is alleviated by increasing the activity of a mammalian SNORF25 receptor which comprises administering to the subject a compound which is a mammalian SNORF25 receptor agonist in an amount effective to treat the abnormality.

This invention additionally provides a method of treating an abnormality in a subject wherein the abnormality is alleviated by decreasing the activity of a mammalian SNORF25 receptor which comprises administering to the subject a compound which is a mammalian SNORF25 receptor antagonist in an amount effective to treat the abnormality.

This invention also provides a process for making a composition of matter which specifically binds to a mammalian SNORF25 receptor which comprises identifying a chemical compound using a process in accordance with this invention and then synthesizing the chemical compound or a novel structural and functional analog or homolog thereof.

This invention further provides a process for preparing a composition, for example, a pharmaceutical composition which comprises admixing a carrier, for example, a pharmaceutically acceptable carrier, and a pharmaceutically effective amount of a chemical compound identified by a process in accordance with this invention or a novel structural and functional analog or homolog thereof.

BRIEF DESCRIPTION OF THE FIGURES

FIGS. 1A–1B Nucleotide sequence including sequence encoding a human SNORF25 receptor (SEQ ID NO: 1). The putative open reading frame is indicated by underlining one start (ATG) codon (at positions 61–63) and the stop codon (at positions 1066–1068). In addition, partial 5' and 3' untranslated sequences are shown.

FIGS. 2A–2B Deduced amino acid sequence (SEQ ID NO: 2) of the human SNORF25 receptor encoded by the longest open reading frame indicated in the nucleotide sequence shown in FIGS. 1A–1B (SEQ ID NO: 1). The seven putative transmembrane (TM) regions are underlined.

FIGS. 3A–3B Nucleotide sequence including sequence encoding a rat SNORF25 receptor (SEQ ID NO: 3). The putative oven reading frame is indicated by underlining one start (ATG) codon (at positions 49–51) and the stop codon (at positions 1054–1056). In addition, partial 5' and 3' untranslated sequences are shown.

FIGS. 4A–4B Deduced amino acid sequence (SEQ ID NO: 4) of the rat SNORF25 receptor encoded by the longest open reading frame indicated in the nucleotide sequence shown in FIGS. 3A–3B (SEQ ID NO: 3). The seven putative transmembrane (TM) regions are underlined.

FIGS. 13A–13B Nucleotide sequence including sequence encoding a mouse SNORF25 receptor (SEQ ID NO: 24). The putative open reading frame is indicated by underlining one start (ATG) codon (at positions 24–26) and the stop codon (at positions 1029–1031). In addition, partial 5' and 3' untranslated sequences are shown.

FIGS. 14A–14B Deduced amino acid sequence (SEQ ID NO: 25) of the mouse SNORF25 receptor encoded by the longest open reading frame indicated in the nucleotide sequence shown in FIGS. 13A–13B (SEQ ID NO: 24). The seven putative transmembrane (TM) regions are underlined.

DETAILED DESCRIPTION OF THE INVENTION

Figure 5:
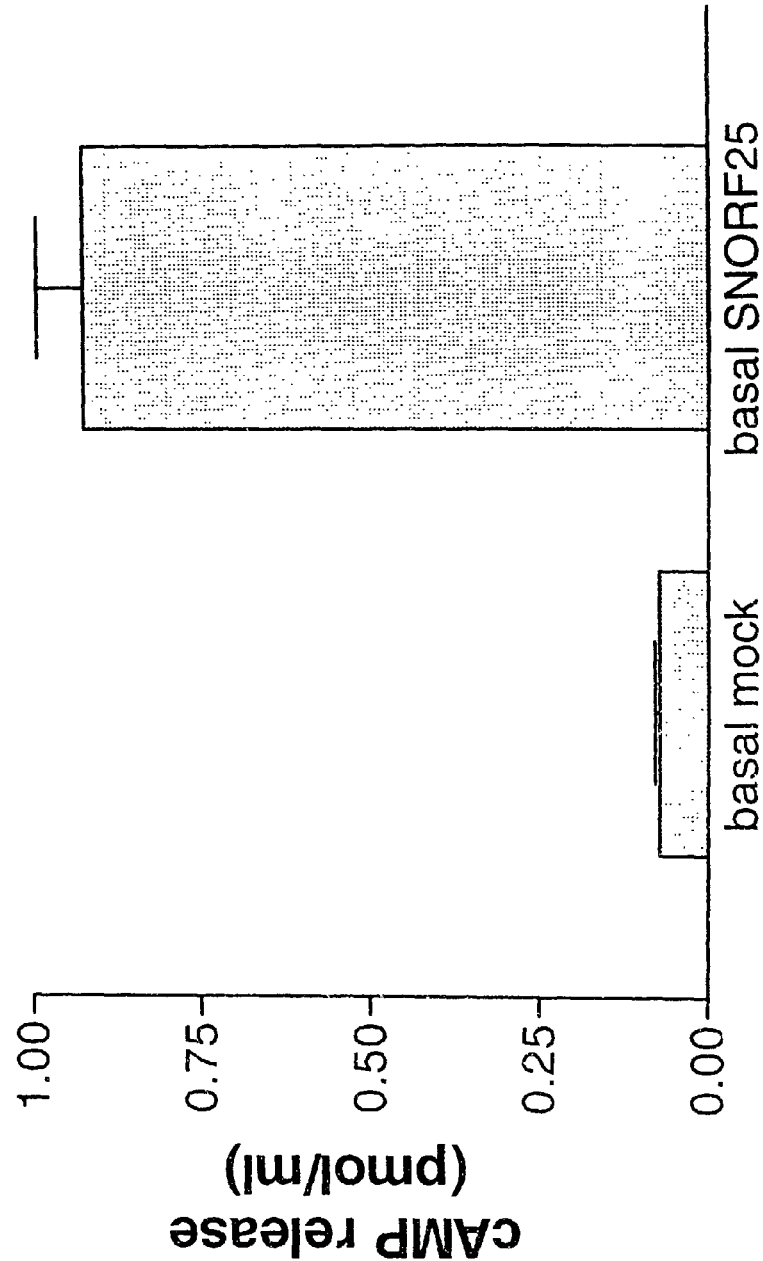
FIG. 5 Comparison of basal cAMP levels of SNORF25- and mock-transfected CHO cells. SNORF25 or empty vector (mock) DNA was transfected into CHO cells as described in Materials and Methods. The transfectants were plated into 96-well plates, and assayed for cAMP release as described. The results of a representative experiment are shown.

This invention provides a recombinant nucleic acid comprising a nucleic acid encoding a mammalian SNORF25 receptor, wherein the mammalian receptor-encoding nucleic acid hybridizes under high stringency conditions to (a) a nucleic acid encoding a human SNORF25 receptor and having a sequence identical to the sequence of the human SNORF25 receptor-encoding nucleic acid contained in plasmid pEXJT3T7-hSNORF25 (ATCC Accession No. 203495) or (b) a nucleic acid encoding a rat SNORF25 receptor and having a sequence identical to the sequence of the rat SNORF25 receptor-encoding nucleic acid contained in plasmid pcDNA3.1-rSNORF25 (ATCC Accession No. 203494).

This invention further provides a recombinant nucleic acid comprising a nucleic acid encoding a human SNORF25 receptor, wherein the human SNORF25 receptor comprises an amino acid sequence identical to the sequence of the human SNORF25 receptor encoded by the shortest open reading frame indicated in FIGS. 1A–1B (SEQ ID NO: 1).

This invention also provides a recombinant nucleic acid comprising a nucleic acid encoding a rat SNORF25 receptor, wherein the rat SNORF25 receptor comprises an amino acid sequence identical to the sequence of the rat SNORF25 receptor encoded by the shortest open reading frame indicated in FIGS. 3A–3B (SEQ ID NO: 3).

This invention also provides a recombinant nucleic acid comprising a nucleic acid encoding a mouse SNORF25 receptor, wherein the mouse SNORF25 receptor comprises an amino acid sequence identical to the sequence of the mouse SNORF25 receptor encoded by the shortest open reading frame indicated in FIGS. 13A–13B (SEQ ID NO: 24).

Plasmid pEXJT3T7-hSNORF25 and plasmid pcDNA3.1-rSNORF25 were both deposited on Nov. 24, 1998, with the American Type Culture Collection (ATCC), 10801 University Blvd., Manassas, Va. 20110-2209, U.S.A. under the provisions of the Budapest Treaty for the International Recognition of the Deposit of Microorganisms for the Purposes of Patent Procedure and were accorded ATCC Accession Nos. 203495 and 203494, respectively.

Plasmid pEXJ-mSNORF25-f was deposited on Jul. 25, 2000, with the American Type Culture Collection (ATCC), 10801 University Blvd., Manassas, Va. 20110-2209, U.S.A. under the provisions of the Budapest Treaty for the International Recognition of the Deposit of Microorganisms for the Purposes of Patent Procedure and was accorded ATCC Patent Depository No. PTA-2263.

Hybridization methods are well known to those of skill in the art. For purposes of this invention, hybridization under high stringency conditions means hybridization performed at 40° C. in a hybridization buffer containing 50% formamide, 5×SSC, 7 mM Tris, 1×Denhardt's, 25 µg/ml salmon sperm DNA; wash at 50° C. in 0.1×SSC, 0.1% SDS.

Throughout this application, the following standard abbreviations are used to indicate specific nucleotide bases:

A=adenine
G=guanine
C=cytosine
T=thymine
M=adenine or cytosine
R=adenine or guanine
W=adenine or thymine
S=cytosine or guanine
Y=cytosine or thymine
K=guanine or thymine
V=adenine, cytosine, or guanine (not thymine)
H=adenine, cytosine, or thymine (not cytosine)
B=cytosine, guanine, or thymine (not adenine)
N=adenine, cytosine, guanine, or thymine (or other modified base such as inosine)
I=inosine Furthermore, the term "agonist" is used throughout this application to indicate any peptide or non-peptidyl compound which increases the activity of any of the polypeptides of the subject invention. The term "antagonist" is used throughout this application to indicate any peptide or non-peptidyl compound which decreases the activity of any of the polypeptides of the subject invention.

Furthermore, as used herein, the phrase "pharmaceutically acceptable carrier" means any of the standard pharmaceutically acceptable carriers. Examples include, but are not limited to, phosphate buffered saline, physiological saline, water, and emulsions, such as oil/water emulsions.

It is possible that the mammalian SNORF25 receptor gene contains introns and furthermore, the possibility exists that additional introns could exist in coding or non-coding regions. In addition, spliced form(s) of mRNA may encode additional amino acids either upstream of the currently defined starting methionine or within the coding region. Further, the existence and use of alternative exons is possible, whereby the mRNA may encode different amino acids within the region comprising the exon. In addition, single amino acid substitutions may arise via the mechanism of RNA editing such that the amino acid sequence of the expressed protein is different than that encoded by the original gene. (Burns, et al., 1996; Chu, et al., 1996). Such variants may exhibit pharmacologic properties differing from the polypeptide encoded by the original gene.

This invention provides splice variants of the mammalian SNORF25 receptors disclosed herein. This invention further provides alternate translation initiation sites and alternately spliced or edited variants of nucleic acids encoding the SNORF25 receptors in accordance with this invention.

This invention also contemplates recombinant nucleic acids which comprise nucleic acids encoding naturally occurring allelic variants of the SNORF25 receptors disclosed herein.

Figure 2A:
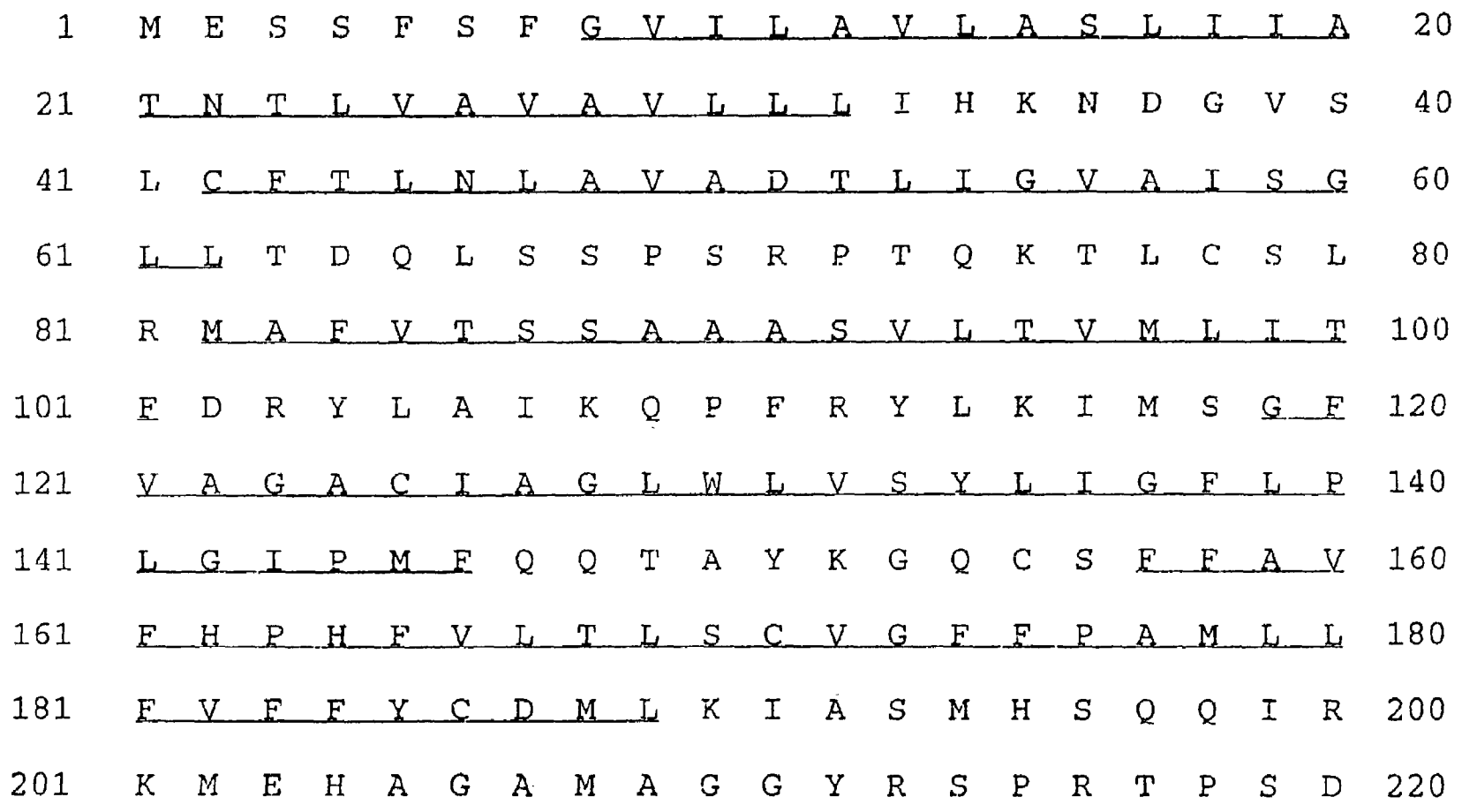

The nucleic acids of the subject invention also include nucleic acid analogs of the human SNORF25 receptor genes, wherein the human SNORF25 receptor gene comprises the nucleic acid sequence shown in FIGS. 1A–1B or contained in plasmid pEXJT3T7-hSNORF25 (ATCC Accession No. 203495). Nucleic acid analogs of the human SNORF25 receptor genes differ from the human SNORF25 receptor genes described herein in terms of the identity or location of one or more nucleic acid bases (deletion analogs containing less than all of the nucleic acid bases shown in FIGS. 1A–1B or contained in plasmid pEXJT3T7-hSNORF25 (ATCC Accession No. 203495), substitution analogs wherein one or more nucleic acid bases shown in FIGS. 1A–1B or contained in plasmid pEXJT3T7-hSNORF25 (ATCC Accession No. 203495), are replaced by other nucleic acid bases, and addition analogs, wherein one or more nucleic acid bases are added to a terminal or medial portion of the nucleic acid sequence) and which encode proteins which share some or all of the properties of the proteins encoded by the nucleic acid sequences shown in FIGS. 1A–1B or contained in plasmid pEXJT3T7-hSNORF25 (ATCC Accession No. 203495). In one embodiment of the present invention, the nucleic acid analog encodes a protein which has an amino acid sequence identical to that shown in FIGS. 2A–2B or encoded by the nucleic acid sequence contained in plasmid pEXJT3T7-hSNORF25 (ATCC Accession No. 203495). In another embodiment, the nucleic acid analog encodes a protein having an amino acid sequence which differs from the amino acid sequences shown in FIGS. 2A–2B or encoded by the nucleic acid contained in plasmid pEXJT3T7-hSNORF25 (ATCC Accession No. 203495). In a further embodiment, the protein encoded by the nucleic acid analog has a function which is the same as the function of the receptor proteins having the amino acid sequence shown in FIGS. 2A–2B. In another embodiment, the function of the protein encoded by the nucleic acid analog differs from the function of the receptor protein having the amino acid sequence shown in FIGS. 2A–2B. In another embodiment, the variation in the nucleic acid sequence occurs within the transmembrane (TM) region of the protein. In a further embodiment, the variation in the nucleic acid sequence occurs outside of the TM region.

Figure 4A:
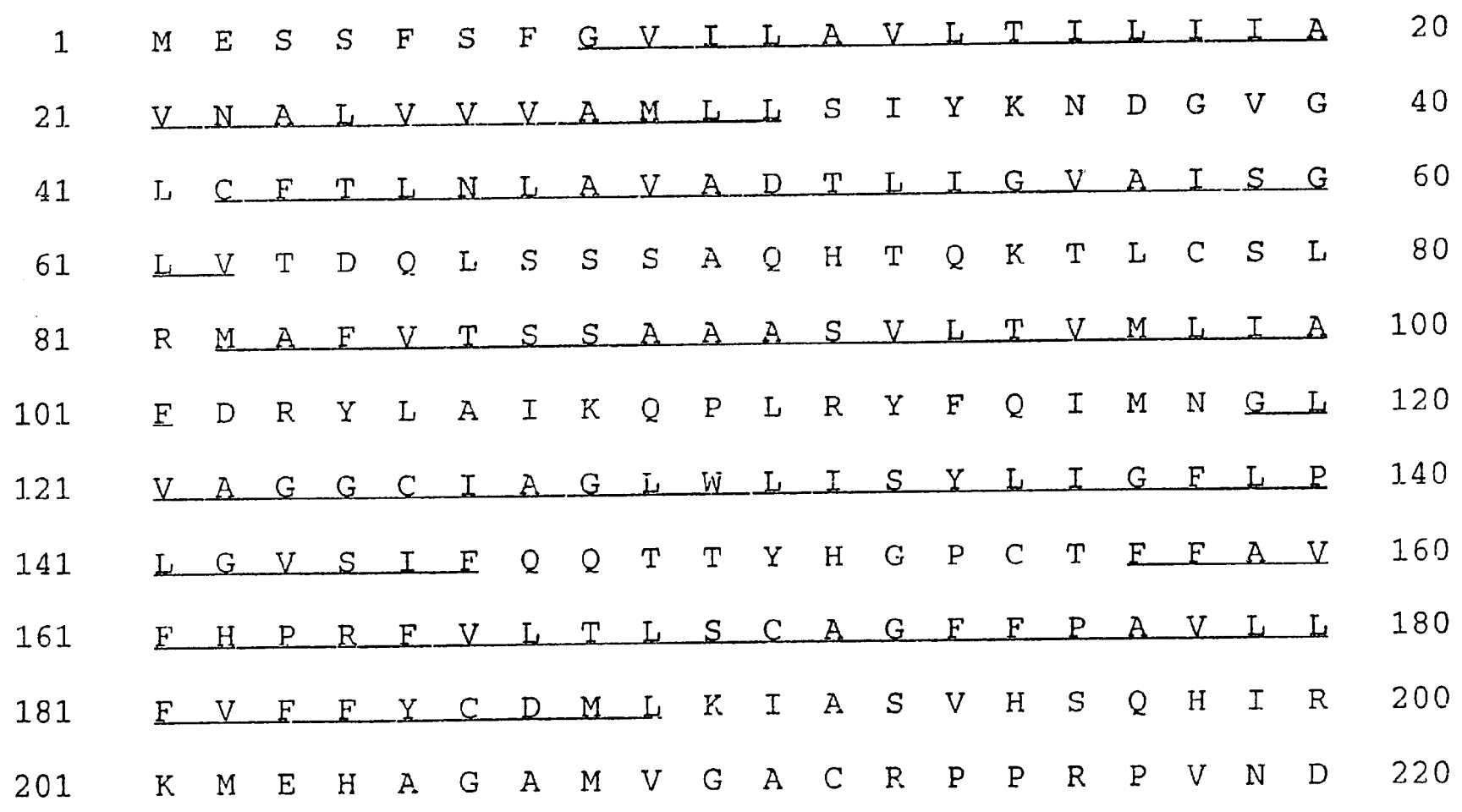
Figure 4B:
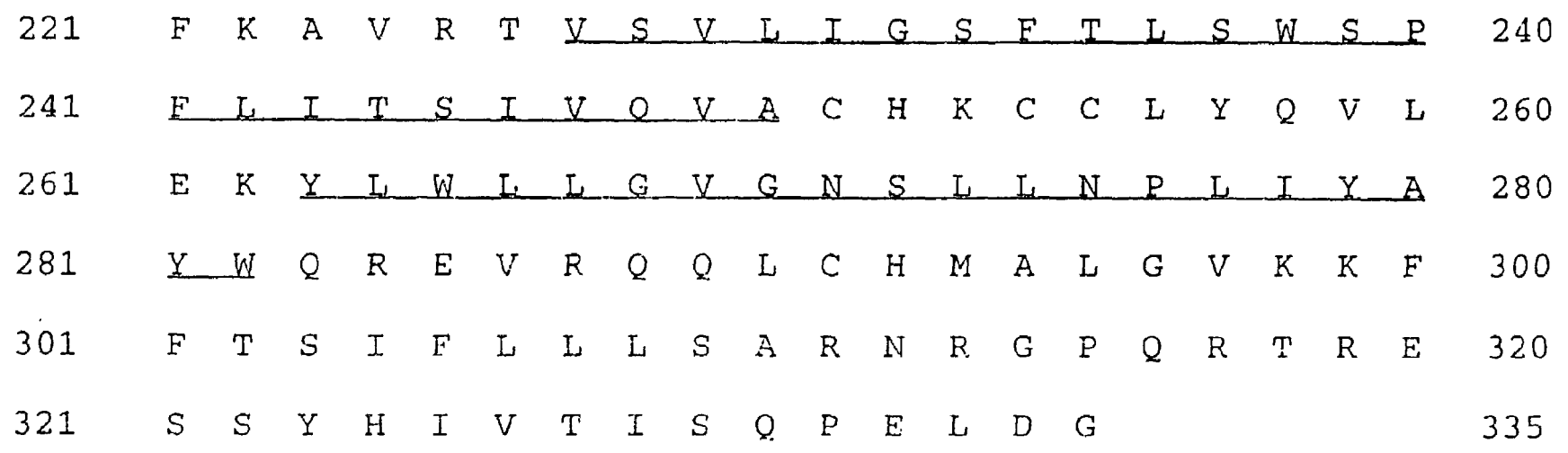

The nucleic acids of the subject invention also include nucleic acid analogs of the rat SNORF25 receptor genes, wherein the rat SNORF25 receptor gene comprises the nucleic acid sequence shown in FIGS. 3A–3B or contained in plasmid pcDNA3.1-rSNORF25 (ATCC Accession No. 203494). Nucleic acid analogs of the rat SNORF25 receptor genes differ from the rat SNORF25 receptor genes described herein in terms of the identity or location of one or more nucleic acid bases (deletion analogs containing less than all of the nucleic acid bases shown in FIGS. 3A–3B or contained in plasmid pcDNA3.1-rSNORF25 (ATCC Accession No. 203494) substitution analogs wherein one or more nucleic acid bases shown in FIGS. 3A–3B or contained in plasmid pcDNA3.1-rSNORF25 (ATCC Accession No. 203494), are replaced by other nucleic acid bases, and addition analogs, wherein one or more nucleic acid bases are added to a terminal or medial portion of the nucleic acid sequence) and which encode proteins which share some or all of the properties of the proteins encoded by the nucleic acid sequences shown in FIGS. 3A–3B or contained in plasmid pcDNA3.1-rSNORF25 (ATCC Accession No. 203494). In one embodiment of the present invention, the nucleic acid analog encodes a protein which has an amino acid sequence identical to that shown in FIGS. 4A–4B or encoded by the nucleic acid sequence contained in plasmid pcDNA3.1-rSNORF25 (ATCC Accession No. 203494). In another embodiment, the nucleic acid analog encodes a protein having an amino acid sequence which differs from the amino acid sequences shown in FIGS. 4A–4B or encoded by the nucleic acid contained in plasmid pcDNA3.1-rSNORF25 (ATCC Accession No. 203494). In a further embodiment, the protein encoded by the nucleic acid analog has a function which is the same as the function of the receptor proteins having the amino acid sequence shown in FIGS. 4A–4B. In another embodiment, the function of the protein encoded by the nucleic acid analog differs from the function of the receptor protein having the amino acid sequence shown in FIGS. 4A–4B. In another embodiment, the variation in the nucleic acid sequence occurs within the transmembrane (TM) region of the protein. In a further embodiment, the variation in the nucleic acid sequence occurs outside of the TM region.

Figure 14A:
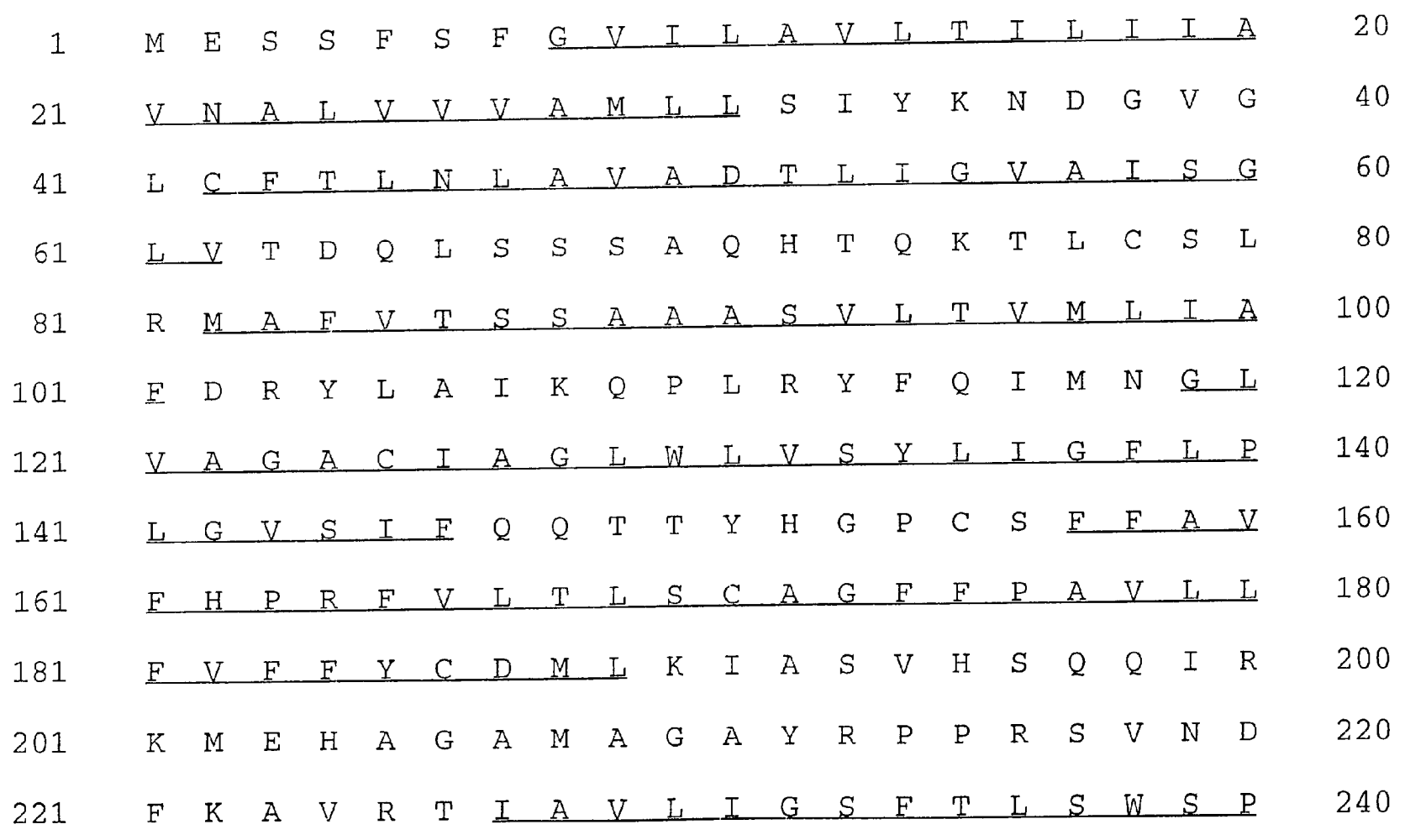
Figure 14B:
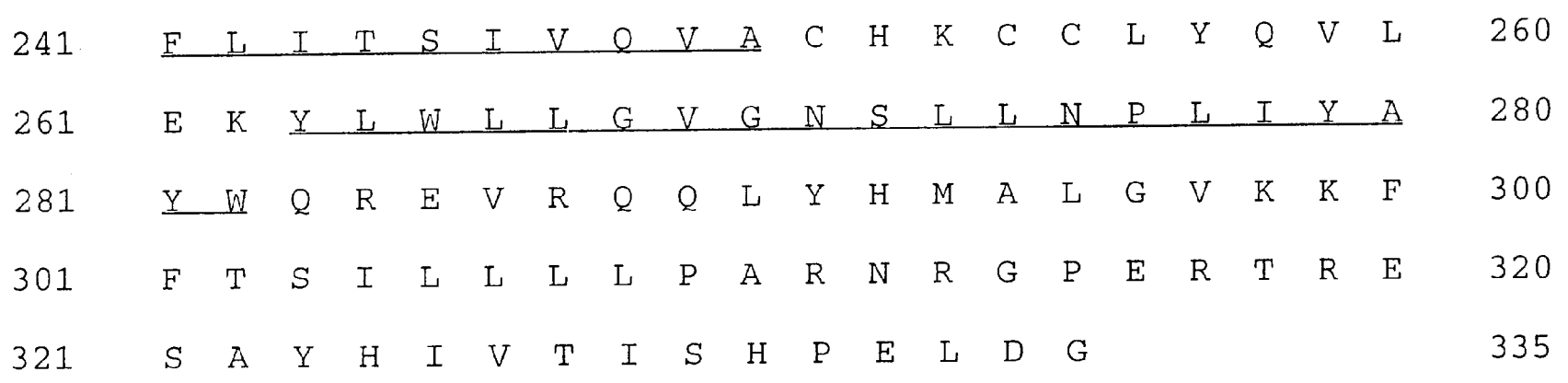

The nucleic acids of the subject invention also include nucleic acid analogs of the mouse SNORF25 receptor genes, wherein the mouse SNORF25 receptor gene comprises the nucleic acid sequence shown in FIGS. 13A–13B or contained in plasmid pEXJ-mSNORF25-f (ATCC Patent Depository No. PTA-2263). Nucleic acid analogs of the mouse SNORF25 receptor genes differ from the mouse SNORF25receptor genes described herein in terms of the identity or location of one or more nucleic acid bases (deletion analogs containing less than all of the nucleic acid bases shown in FIGS. 13A–13B or contained in plasmid pEXJ-mSNORF25-f (ATCC Patent Depository No. PTA-2263) substitution analogs wherein one or more nucleic acid bases shown in FIGS. 13A–13B or contained in plasmid pEXJ-mSNORF25-f (ATCC Patent Depository No. PTA-2263), are replaced by other nucleic acid bases, and addition analogs, wherein one or more nucleic acid bases are added to a terminal or medial portion of the nucleic acid sequence) and which encode proteins which share some or all of the properties of the proteins encoded by the nucleic acid sequences shown in FIG. 13A–13B or contained in plasmid pEXJ-mSNORF25-f (ATCC Patent Depository No. PTA-2263). In one embodiment of the present invention, the nucleic acid analog encodes a protein which has an amino acid sequence identical to that shown in FIGS. 14A–14B or encoded by the nucleic acid sequence contained in plasmid pEXJ-mSNORF25-f (ATCC Patent Depository No. PTA-2263. In another embodiment, the nucleic acid analog encodes a protein having an amino acid sequence which differs from the amino acid sequences shown in FIGS. 14A–14B or encoded by the nucleic acid contained in plasmid pEXJ-mSNORF25-f (ATCC Patent Depository No. PTA-2263). In a further embodiment, the protein encoded by the nucleic acid analog has a function which is the same as the function of the receptor proteins having the amino acid sequence shown in FIGS. 14A–14B. In another embodiment, the function of the protein encoded by the nucleic acid analog differs from the function of the receptor protein having the amino acid sequence shown in FIGS. 14A–14B. In another embodiment, the variation in the nucleic acid sequence occurs within the transmembrane (TM) region of the protein. In a further embodiment, the variation in the nucleic acid sequence occurs outside of the TM region.

This invention provides the above-described isolated nucleic acid, wherein the nucleic acid is DNA. In an embodiment, the DNA is cDNA. In another embodiment, the DNA is genomic DNA. In still another embodiment, the nucleic acid is RNA. Methods for production and manipulation of nucleic acid molecules are well known in the art.

This invention further provides nucleic acid which is degenerate with respect to the DNA encoding any of the polypeptides described herein. In an embodiment, the nucleic acid comprises a nucleotide sequence which is degenerate with respect to the nucleotide sequence shown in FIGS. 1A–1B (SEQ ID NO: 1) or the nucleotide sequence contained in the plasmid pEXJT3T7-hSNORF25 (ATCC Accession No. 203495), that is, a nucleotide sequence which is translated into the same amino acid sequence.

This invention further provides nucleic acid which is degenerate with respect to the DNA encoding any of the polypeptides described herein. In an embodiment, the nucleic acid comprises a nucleotide sequence which is degenerate with respect to the nucleotide sequence shown in FIGS. 3A–3B (SEQ ID NO: 3) or the nucleotide sequence contained in the plasmid pcDNA3.1-rSNORF25 (ATCC Accession No. 203494), that is, a nucleotide sequence which is translated into the same amino acid sequence. In another embodiment, the nucleic acid comprises a nucleotide sequence which is degenerate with respect to the nucleotide sequence shown in FIGS. 13A–13B (SEQ ID NO: 24 ) or the nucleotide sequence contained In the plasmid pEXJ-mSNORF25-f (ATCC Patent Depository No. PTA-2283), that is, a nucleotide sequence which is translated into the same amino acid sequence.

This invention also encompasses DNAs and cDNAs which encode amino acid sequences which differ from those of the polypeptides according to this invention, but which should not produce phenotypic changes. Alternately, this invention also encompasses DNAs, cDNAs, and RNAs which hybridize with the DNA, cDNA, and RNA according to the subject invention. Hybridization methods are well known to those of skill in the art.

The nucleic acids according to the subject invention also include nucleic acid molecules coding for polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs wherein one or more amino acid residues is added to a terminal or medial portion of the polypeptides) and which share some or all properties of naturally-occurring forms. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors. The creation of polypeptide analogs is well known to those of skill in the art (Spurney, R. F. et al. (1997); Fong, T. M. et al. (1995); Underwood, D. J. et al. (1994); Graziano, M. P. et al. (1996); Guan X. M. et al. (1995)).

The modified polypeptides according to this invention may be transfected into cells either transiently or stably using methods well-known in the art, examples of which are disclosed herein. This invention also provides binding assays using the modified polypeptides, in which the polypeptide is expressed either transiently or in stable cell lines. This invention further provides a compound identified using a modified polypeptide in a binding assay such as the binding assays described herein.

The nucleic acids described and claimed herein are useful for the information which they provide concerning the amino acid sequence of the polypeptide and as products for the large scale synthesis of the polypeptides by a variety of recombinant techniques. The nucleic acid molecule is useful for generating new cloning and expression vectors, transformed and transfected prokaryotic and eukaryotic host cells, and new and useful methods for cultured growth of such host cells capable of expression of the polypeptide and related products.

This invention also provides an isolated nucleic acid encoding species homologs of the SNORF25 receptors encoded by the nucleic acid sequence shown in FIGS. 1A–1B (SEQ ID NO: 1) or encoded by the plasmid pEXJT3T7-hSNORF25 (ATCC Accession No. 203495). In one embodiment, the nucleic acid encodes a mammalian SNORF25 receptor homolog which has substantially the same amino acid sequence as does the SNORF25 receptor encoded by the plasmid pEXJT3T7-hSNORF25 (ATCC Accession No. 203495). In another embodiment, the nucleic acid encodes a mammalian SNORF25 receptor homolog which has above 75% amino acid identity to the SNORF25 receptor encoded by the plasmid pEXJT3T7-hSNORF25 (ATCC Accession No. 203495); preferably above 85% amino acid identity to the SNORF25 receptor encoded by the plasmid pEXJT3T7-hSNORF25 (ATCC Accession No. 203495); most preferably above 95% amino acid identity to the SNORF25 receptor encoded by the plasmid pEXJT3T7-hSNORF25 (ATCC Accession No. 203495). In another embodiment, the mammalian SNORF25 receptor homolog has above 70% nucleic acid identity to the SNORF25 receptor gene contained in plasmid pEXJT3T7-hSNORF25 (ATCC Accession No. 203495); preferably above 80% nucleic acid identity to the SNORF25 receptor gene contained in the plasmid pEXJT3T7-hSNORF25 (ATCC Accession No. 203495); more preferably above 90% nucleic acid identity to the SNORF25 receptor gene contained in the plasmid pEXJT3T7-hSNORF25 (ATCC Accession No. 203495). Examples of methods for isolating and purifying species homologs are described elsewhere (e.g., U.S. Pat. No. 5,602,024, WO94/14957, WO97/26853, WO98/15570).

This invention also provides an isolated nucleic acid encoding species homologs of the SNORF25 receptors encoded by the nucleic acid sequence shown in FIGS. 3A–3B (SEQ ID NO: 3) or encoded by the plasmid pcDNA3.1-rSNORF25 (ATCC Accession No. 203494). In one embodiment, the nucleic acid encodes a mammalian SNORF25 receptor homolog which has substantially the same amino acid sequence as does the SNORF25 receptor encoded by the plasmid pcDNA3.1-rSNORF25 (ATCC Accession No. 203494). In another embodiment, the nucleic acid encodes a mammalian SNORF25 receptor homolog which has above 75% amino acid identity to the SNORF25 receptor encoded by the plasmid pcDNA3.1-rSNORF25 (ATCC Accession No. 203494); preferably above 85% amino acid identity to the SNORF25 receptor encoded by the plasmid pcDNA3.1-rSNORF25 (ATCC Accession No. 203494); most preferably above 95% amino acid identity to the SNORF25 receptor encoded by the plasmid pcDNA3.1-rSNORF25 (ATCC Accession No. 203494). In another embodiment, the mammalian SNORF25 receptor homolog has above 70% nucleic acid identity to the SNORF25 receptor gene contained in plasmid pcDNA3.1-rSNORF25 (ATCC Accession No. 203494); preferably above 80% nucleic acid identity to the SNORF25 receptor gene contained in the plasmid pcDNA3.1-rSNORF25 (ATCC Accession No. 203494); more preferably above 90% nucleic acid identity to the SNORF25 receptor gene contained in the plasmid pcDNA3.1-rSNORF25 (ATCC Accession No. 203494).

This invention also provides an isolated nucleic acid encoding species homologs of the SNORF25 receptors encoded by the nucleic acid sequence shown in FIGS. 13A–13B (SEQ ID NO: 24) or encoded by the plasmid pEXJ-mSNORF25-f (ATCC Patent Depository No. PTA-2263). In one embodiment, the nucleic acid encodes a mammalian SNORF25 receptor homolog which has substantially the same amino acid sequence as does the SNORF25 receptor encoded by the plasmid pEXJ-mSNORF25-f (ATCC Patent Depository No. PTA-2263). In another embodiment, the nucleic acid encodes a mammalian SNORF25 receptor homolog which has above 75% amino acid identity to the SNORF25 receptor encoded by the plasmid pEXI-mSNORF25-f (ATCC Patent Depository No. PTA-2263); preferably above 85% amino acid identity to the SNORF25 receptor encoded by the plasmid pEXJ-mSNORF25-f (ATCC Patent Depository No. PTA-2263); most preferably above 95% amino acid identity to the SNORF25 receptor encoded by the plasmid pEXJ-mSNORF25-f (ATCC Patent Depository No. PTA-2263). In another embodiment, the mammalian SNORF25 receptor homolog has above 70% nucleic acid Identity to the SNORF25 receptor gene contained in plasmid pEXJ-mSNORF25-f (ATCC Patent Depository No. PTA-2263); preferably above 80% nucleic acid identity to the SNORF25 receptor gene contained in the plasmid pEXJ-mSNORF25-f (ATCC Patent Depository No. PTA-2263); more preferably above 90% nucleic acid identity to the SNORF25receptor gene contained in the plasmid pEXJ-mSNORF25-f (ATCC Patent Depository No. PTA-2263).

This invention provides an isolated nucleic acid encoding a modified mammalian SNORF25 receptor, which differs from a mammalian SNORF25 receptor by having an amino acid(s) deletion, replacement, or addition in the third intracellular domain.

This invention provides an isolated nucleic acid encoding a mammalian SNORF25 receptor. In one embodiment, the nucleic acid is DNA. In another embodiment, the DNA is cDNA. In another embodiment, the DNA is genomic DNA. In another embodiment, the nucleic acid is RNA. In another embodiment, the mammalian SNORF25 receptor is a human SNORF25 receptor. In another embodiment, the human SNORF25 receptor has an amino acid sequence identical to that encoded by the plasmid pEXJT3T7-hSNORF25 (ATCC Accession No. 203495). In another embodiment, the human SNORF25 receptor has an amino acid sequence identical to the amino acid sequence shown in FIGS. 2A–2B (SEQ ID NO: 2).

In an embodiment, the mammalian SNORF25 receptor is a rat SNORF25 receptor. In another embodiment, the rat SNORF25 receptor has an amino acid sequence identical to that encoded by the plasmid pcDNA3.1-rSNORF25 (ATCC Accession No. 203494). In another embodiment, the rat SNORF25 receptor has an amino acid sequence identical to the amino acid sequence shown in FIGS. 4A–4B (SEQ ID NO: 4).

In an embodiment, the mammalian SNORF25 receptor is a mouse SNORF25 receptor. In another embodiment, the mouse SNORF25 receptor has an amino acid sequence identical to that encoded by the plasmid pEXJ-mSNORF25-f (ATCC Patent Depository No. PTA-2263). In another embodiment, the mouse SNORF26 receptor has an amino acid sequence identical to the amino acid sequence shown in FIGS. 14A–14B (SEQ ID NO: 25).

This invention provides a purified mammalian SNORF25 receptor protein. In one embodiment, the SNORF25 receptor protein is a human SNORF25 receptor protein. In a further embodiment, the SNORF25 receptor protein is a rat SNORF25 receptor protein. In yet a further embodiment, the SNORF25 receptor protein is a mouse SNORF25 receptor protein.

This invention provides a vector comprising a nucleic acid in accordance with this invention. This invention further provides a vector adapted for expression in a cell which comprises the regulatory elements necessary for expression of the nucleic acid in the cell operatively linked to the nucleic acid encoding the receptor so as to permit expression thereof, wherein the cell is a bacterial, amphibian, yeast, insect or mammalian cell. In one embodiment, the vector is a baculovirus. In another embodiment, the vector is a plasmid.

This invention provides a plasmid designated pEXJT3T7-hSNORF25 (ATCC Accession No. 203495). This invention also provides a plasmid designated pcDNA3.1-rSNORF25 (ATCC Accession No. 203494). This invention also provides a plasmid designated pEXJ-mSNORF25-f (ATCC Patent Depository No. PTA-2263).

This invention further provides any vector or plasmid which comprises modified untranslated sequences, which are beneficial for expression in desired host cells or for use in binding or functional assays. For example, a vector or plasmid with untranslated sequences of varying lengths may express differing amounts of the polypeptide depending upon the host cell used. In an embodiment, the vector or plasmid comprises the coding sequence of the polypeptide and the regulatory elements necessary for expression in the host cell.

This invention provides a cell comprising a vector in accordance with this invention. In one embodiment, the cell is a non-mammalian cell. In one embodiment, the non-mammalian cell is a *Xenopus* oocyte cell or a *Xenopus* melanophore cell. In another embodiment, the cell is a mammalian cell. In another embodiment, the cell is a COS-7 cell, a 293 human embryonic kidney cell, a NIH-3T3 cell, a LM(tk−) cell, a mouse Y1 cell, or a CHO cell. In another embodiment, the cell is an insect cell. In another embodiment, the insect cell is an Sf9 cell, an Sf21 cell or a *Trichoplusia* ni 5B-4 cell.

This invention provides a membrane preparation isolated from a cell in accordance with this invention.

Furthermore, this invention provides a nucleic acid probe comprising at least 15 nucleotides, which probe specifically hybridizes with a nucleic acid encoding a mammalian SNORF25 receptor, wherein the probe has a sequence complementary to a unique sequence present within one of the two strands of the nucleic acid encoding the mammalian SNORF25 receptor contained in plasmid pEXJT3T7-hSNORF25 (ATCC Accession No. 203495), plasmid pcDNA3.1-rSNORF25 (ATCC Accession No.203494) or plasmid pEXJ-mSNORF25-f (ATCC Patent Depository No. PTA-2263).

This invention further provides a nucleic acid probe comprising at least 15 nucleotides, which probe specifically hybridizes with a nucleic acid encoding a mammalian SNORF25 receptor, wherein the probe has a sequence complementary to a unique sequence present within (a) the nucleic acid sequence shown in FIGS. 1A–1B (SEQ ID NO: 1) or (b) the reverse complement thereof. This invention also provides a nucleic acid probe comprising at least 15 nucleotides, which probe specifically hybridizes with a nucleic acid encoding a mammalian SNORF25 receptor, wherein the probe has a sequence complementary to a unique sequence present within (a) the nucleic acid sequence shown in FIGS. 3A–3B (SEQ ID NO: 3) or (b) the reverse complement thereof. This invention also provides a nucleic acid probe comprising at least 15 nucleotides, which probe specifically hybridizes with a nucleic acid encoding a mammalian SNORF25 receptor, wherein the probe has a sequence complementary to a unique sequence present within (a) the nucleic acid sequence shown in FIGS. 13A–13B (SEQ ID NO: 24) or (b) the reverse complement thereof. In one embodiment, the nucleic acid is DNA. In another embodiment, the nucleic acid is RNA.

As used herein, the phrase "specifically hybridizing" means the ability of a nucleic acid molecule to recognize a nucleic acid sequence complementary to its own and to form double-helical segments through hydrogen bonding between complementary base pairs.

The nucleic acids according to this invention may be used as probes to obtain homologous nucleic acids from other species and to detect the existence of nucleic acids having complementary sequences in samples.

The nucleic acids may also be used to express the receptors they encode in transfected cells.

The use of a constitutively active receptor encoded by SNORF25 either occurring naturally without further modification or after appropriate point mutations, deletions or the like, allows screening for antagonists and in vivo use of such antagonists to attribute a role to receptor SNORF25 without prior knowledge of the endogenous ligand.

Use of the nucleic acids further enables elucidation of possible receptor diversity and of the existence of multiple subtypes within a family of receptors of which SNORF25 is a member.

Finally, it is contemplated that this receptor will serve as a valuable tool for designing drugs for treating various pathophysiological conditions such as chronic and acute inflammation, arthritis, autoimmune diseases, transplant rejection, graft vs. host disease, bacterial, fungal, protozoan and viral infections, septicemia, AIDS, pain, psychotic and neurological disorders, including anxiety, depression, schizophrenia, dementia, mental retardation, memory loss, epilepsy, neurological disorders, neuromotor disorders, respiratory disorders, asthma, eating/body weight disorders including obesity, bulimia, diabetes, anorexia, nausea, hypertension, hypotension, vascular and cardiovascular disorders, ischemia, stroke, cancers, ulcers, urinary retention, sexual/reproductive disorders, circadian rhythm disorders, renal disorders, bone diseases including osteoporosis, benign prostatic hypertrophy, gastrointestinal disorders, nasal congestion, dermatological disorders such as psoriasis, allergies, Parkinson's disease, Alzheimer's disease, acute heart failure, angina disorders, delirium, dyskinesias such as Huntington's disease or Gille's de la Tourette's syndrome, among others and diagnostic assays for such conditions. This receptor may also serve as a valuable tool for designing drugs for chemoprevention.

Methods of transfecting cells e.g. mammalian cells, with such nucleic acid to obtain cells in which the receptor is expressed on the surface of the cell are well known in the art. (See, for example, U.S. Pat. Nos. 5,053,337; 5,155,218; 5,360,735; 5,472,866; 5,476,782; 5,516,653; 5,545,549; 5,556,753; 5,595,880; 5,602,024; 5,639,652; 5,652,113; 5,661,024; 5,766,879; 5,786,155; and 5,786,157, the disclosures of which are hereby incorporated by reference in their entireties into this application.)

Such transfected cells may also be used to test compounds and screen compound libraries to obtain compounds which bind to the SNORF25 receptor, as well as compounds which activate or inhibit activation of functional responses in such cells, and therefore are likely to do so in vivo. (See, for example, U.S. Pat. Nos. 5,053,337; 5,155,218; 5,360,735; 5,472,866; 5,476,782; 5,516,653; 5,545,549; 5,556,753; 5,595,880; 5,602,024; 5,639,652; 5,652,113; 5,661,024; 5,766,879; 5,786,155; and 5,786,157, the disclosures of which are hereby incorporated by reference in their entireties into this application.)

This invention further provides an antibody capable of binding to a mammalian receptor encoded by a nucleic acid encoding a mammalian receptor. In one embodiment, the mammalian receptor is a human receptor. In a further embodiment, the mammalian receptor is a rat receptor. In another embodiment, the mammalian receptor is a mouse receptor. This invention also provides an agent capable of competitively inhibiting the binding of an antibody to a mammalian receptor. In one embodiment, the antibody is a monoclonal antibody or antisera.

Methods of preparing and employing antisense oligonucleotides, antibodies, nucleic acid probes and transgenic animals directed to the SNORF25 receptor are well known in the art. (See, for example, U.S. Pat. Nos. 5,053,337; 5,155,218; 5,360,735; 5,472,866; 5,476,782; 5,516,653; 5,545,549; 5,556,753; 5,595,880; 5,602,024; 5,639,652; 5,652,113; 5,661,024; 5,766,879; 5,786,155; and 5,786,157, the disclosures of which are hereby incorporated by reference in their entireties into this application.)

This invention also provides an antisense oligonucleotide having a sequence capable of specifically hybridizing to RNA encoding a mammalian SNORF25 receptor, so as to prevent translation of such RNA. This invention further provides an antisense oligonucleotide having a sequence capable of specifically hybridizing to genomic DNA encoding a mammalian SNORF25 receptor, so as to prevent transcription of such genomic DNA. In one embodiment, the oligonucleotide comprises chemically modified nucleotides or nucleotide analogues.

This invention provides an antibody capable of binding to a mammalian SNORF25 receptor encoded by a nucleic acid in accordance with this invention. In one embodiment, the mammalian SNORF25 receptor is a human SNORF25 receptor. In a further embodiment, the mammalian SNORF25 receptor is a rat SNORF25 receptor. In one embodiment, the mammalian SNORF25 receptor is a mouse SNORF25 receptor.

Moreover, this invention provides an agent capable of competitively inhibiting the binding of an antibody in accordance with this invention to a mammalian SNORF25 receptor. In one embodiment, the antibody is a monoclonal antibody or antisera.

This invention still further provides a pharmaceutical composition comprising (a) an amount of an oligonucleotide in accordance with this invention capable of passing through a cell membrane and effective to reduce expression of a mammalian SNORF25 receptor and (b) a pharmaceutically acceptable carrier capable of passing through the cell membrane.

In one embodiment, the oligonucleotide is coupled to a substance which inactivates mRNA. In another embodiment, the substance which inactivates mRNA is a ribozyme. In another embodiment, the pharmaceutically acceptable carrier comprises a structure which binds to a mammalian SNORF25 receptor on a cell capable of being taken up by the cells after binding to the structure. In another embodiment, the pharmaceutically acceptable carrier is capable of binding to a mammalian SNORF25 receptor which is specific for a selected cell type.

This invention also provides a pharmaceutical composition which comprises an amount of an antibody in accordance with this invention effective to block binding of a ligand to a human SNORF25 receptor and a pharmaceutically acceptable carrier.

This invention further provides a transgenic, nonhuman mammal expressing DNA encoding a mammalian SNORF25 receptor in accordance with this invention. This invention provides a transgenic, nonhuman mammal comprising a homologous recombination knockout of a native mammalian SNORF25 receptor. This invention further provides a transgenic, nonhuman mammal whose genome comprises antisense DNA complementary to DNA encoding a mammalian SNORF25 receptor in accordance with this invention so placed within such genome as to be transcribed into antisense mRNA which is complementary to and hybridizes with mRNA encoding the mammalian SNORF25 receptor so as to reduce translation of such mRNA and expression of such receptor. In one embodiment, the DNA encoding the mammalian SNORF25 receptor additionally comprises an inducible promoter. In another embodiment, the DNA encoding the mammalian SNORF25 receptor additionally comprises tissue specific regulatory elements. In another embodiment, the transgenic, nonhuman mammal is a mouse.

Animal model systems which elucidate the physiological and behavioral roles of the SNORF25 receptor are produced by creating transgenic animals in which the activity of the SNORF25 receptor is either increased or decreased, or the amino acid sequence of the expressed SNORF25 receptor is altered, by a variety of techniques. Examples of these techniques include, but are not limited to: 1) Insertion of normal or mutant versions of DNA encoding a SNORF25 receptor, by microinjection, electroporation, retroviral transfection or other means well known to those skilled in the art, into appropriate fertilized embryos in order to produce a transgenic animal or 2) Homologous recombination of mutant or normal, human or animal versions of these genes with the native gene locus to produce transgenic animals with alterations in the regulation of expression or in the structure of these SNORF25 receptor sequences. The technique of homologous recombination is well known in the art. It replaces the native gene with the inserted gene and so is useful for producing an animal that cannot express native SNORF25 receptors but does express, for example, an inserted mutant SNORF25 receptor, which has replaced the native SNORF25 receptor in the animal's genome by recombination, resulting in underexpression of the receptor. Microinjection adds genes to the genome, but does not remove them, and so is useful for producing an animal which expresses its native SNORF25 receptors, as well as overexpressing exogenously added SNORF25 receptors, perhaps in a tissue-specific manner.

One means available for producing a transgenic animal, with a mouse as an example, is as follows: Female mice are mated, and the resulting fertilized eggs are dissected out of their oviducts. The eggs are stored in an appropriate medium such as M2 medium. DNA or cDNA encoding a SNORF25 receptor is purified from a vector by methods well known in the art. Inducible promoters may be fused with the coding region of the DNA to provide an experimental means to regulate expression of the trans-gene. Alternatively or in addition, tissue specific regulatory elements may be fused with the coding region to permit tissue-specific expression of the trans-gene. The DNA, in an appropriately buffered solution, is put into a microinjection needle (which may be made from capillary tubing using a pipet puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only method for inserting DNA into the egg cell, and is used here only for exemplary purposes.

A second means available for producing a transgenic animal, with a mouse as an example, is as follows: Embryonic stem cells (ES cells) are harvested from the inner cell mass of mouse blastocysts. A DNA construct is generated which contains several kb of the SNORF25 gene and flanking regions, with a selectable marker, such as one conferring neomycin resistance, inserted within the SNORF25 coding region and perhaps a negatively selectable gene inserted outside the homologous region. ES cells are then transformed with this DNA construct, and homologous recombination occurs. Southern blot analysis and/or PCR analysis may be used to screen for cells that have incorporated the SNORF25 construct into the correct genomic locus. Donor females are mated, blastocysts are harvested, and selected ES cells are injected into the blastocysts. These blastocysts are then implanted into the uterus of pseudopregnant mice, as above. The heterozygous offspring from these mice are then mated to produce mice homozygous for the transgene.

This invention provides a process for identifying a chemical compound which specifically binds to a mammalian SNORF25 receptor which comprises contacting cells containing DNA encoding, and expressing on their cell surface, the mammalian SNORF25 receptor, wherein such cells do not normally express the mammalian SNORF25 receptor, with the compound under conditions suitable for binding, and detecting specific binding of the chemical compound to the mammalian SNORF25 receptor. This invention further provides a process for identifying a chemical compound which specifically binds to a mammalian SNORF25 receptor which comprises contacting a membrane preparation from cells containing DNA encoding, and expressing on their cell surface, the mammalian SNORF25 receptor, wherein such cells do not normally express the mammalian SNORF25 receptor, with the compound under conditions suitable for binding, and detecting specific binding of the chemical compound to the mammalian SNORF25 receptor.

In one embodiment, the mammalian SNORF25 receptor is a human SNORF25 receptor. In another embodiment, the mammalian SNORF25 receptor has substantially the same amino acid sequence as the human SNORF25 receptor encoded by plasmid pEXJT3T7-hSNORF25 (ATCC Accession No. 203495). In another embodiment, the mammalian SNORF25 receptor has substantially the same amino acid sequence as that shown in FIGS. 2A–2B (SEQ ID NO: 2). In another embodiment, the mammalian SNORF25 receptor has the amino acid sequence shown in FIGS. 2A–2B (SEQ ID NO: 2).

In another embodiment, the mammalian SNORF25 receptor is a rat SNORF25 receptor. In another embodiment, the mammalian SNORF25 receptor has substantially the same amino acid sequence as the rat SNORF25 receptor encoded by plasmid pcDNA3.1-rSNORF25 (ATCC Accession No. 203494). In another embodiment, the mammalian SNORF25 receptor has substantially the same amino acid sequence as that shown in FIGS. 4A–4B (SEQ ID NO: 4). In another embodiment, the mammalian SNORF25 receptor has the amino acid sequence shown in FIGS. 4A–4B (SEQ ID NO: 4).

In another embodiment, the mammalian SNORF25 receptor is a mouse SNORF25 receptor. In another embodiment, the mammalian SNORF25 receptor has substantially the same amino acid sequence as the mouse SNORF25 receptor encoded by plasmid pEXJ-mSNORF25-f (ATCC Patent Depository No. PTA-2263). In another embodiment, the mammalian SNORF25 receptor has substantially the same amino acid sequence as that shown in FIGS. 14A–14B (SEQ ID NO: 25). In another embodiment, the mammalian SNORF25 receptor has the amino acid sequence shown in FIGS. 14A–14B (SEQ ID NO: 25).

In one embodiment, the compound is not previously known to bind to a mammalian SNORF25 receptor. In one embodiment, the cell is an insect cell. In one embodiment, the cell is a mammalian cell. In another embodiment, the cell is nonneuronal in origin. In another embodiment, the nonneuronal cell is a COS-7 cell, 293 human embryonic kidney cell, a CHO cell, a NIH-3T3 cell, a mouse Y1 cell, or a LM(tk−) cell. In another embodiment, the compound is a compound not previously known to bind to a mammalian SNORF25 receptor. This invention provides a compound identified by the preceding process of this invention.

This invention still further provides a process involving competitive binding for identifying a chemical compound which specifically binds to a mammalian SNORF25 receptor which comprises separately contacting cells expressing on their cell surface the mammalian SNORF25 receptor, wherein such cells do not normally express the mammalian SNORF25 receptor, with both the chemical compound and a second chemical compound known to bind to the receptor, and with only the second chemical compound, under conditions suitable for binding of such compounds to the receptor, and detecting specific binding of the chemical compound to the mammalian SNORF25 receptor, a decrease in the binding of the second chemical compound to the mammalian SNORF25 receptor in the presence of the chemical compound being tested indicating that such chemical compound binds to the mammalian SNORF25 receptor.

This invention provides a process involving competitive binding for identifying a chemical compound which specifically binds to a mammalian SNORF25 receptor which comprises separately contacting a membrane preparation from cells expressing on their cell surface the mammalian SNORF25 receptor, wherein such cells do not normally express the mammalian SNORF25 receptor, with both the chemical compound and a second chemical compound known to bind to the receptor, and with only the second chemical compound, under conditions suitable for binding of such compounds to the receptor, and detecting specific binding of the chemical compound to the mammalian SNORF25 receptor, a decrease in the binding of the second chemical compound to the mammalian SNORF25 receptor in the presence of the chemical compound being tested indicating that such chemical compound binds to the mammalian SNORF25 receptor.

In one embodiment, the mammalian SNORF25 receptor is a human SNORF25 receptor. In another embodiment, the mammalian SNORF25 receptor is a rat SNORF25 receptor. In another embodiment, the mammalian SNORF25 receptor is a mouse SNORF25 receptor. In a further embodiment, the cell is an insect cell. In another embodiment, the cell is a mammalian cell. In another embodiment, the cell is nonneuronal in origin. In another embodiment, the nonneuronal cell is a COS-7 cell, 293 human embryonic kidney cell, a CHO cell, a NIH-3T3 cell, a mouse Y1 cell, or a LM(tk−) cell. In another embodiment, the compound is not previously known to bind to a mammalian SNORF25 receptor. This invention provides a compound identified by the preceding process of this invention.

In an embodiment of the invention, the second compound is a lipid-like molecule including, but not limited to, ATRA and phospholipids. Examples of phospholipids include, but are not limited to, PAF(C18), PAF(C16), lyso-PAF(C18) and lyso-PAF(C16).

This invention provides a method of screening a plurality of chemical compounds not known to bind to a mammalian SNORF25 receptor to identify a compound which specifically binds to the mammalian SNORF25 receptor, which comprises (a) contacting cells transfected with, and expressing, DNA encoding the mammalian SNORF25 receptor with a compound known to bind specifically to the mammalian SNORF25 receptor; (b) contacting the cells of step (a) with the plurality of compounds not known to bind specifically to the mammalian SNORF25 receptor, under conditions permitting binding of compounds known to bind to the mammalian SNORF25 receptor; (c) determining whether the binding of the compound known to bind to the mammalian SNORF25 receptor is reduced in the presence of the plurality of compounds, relative to the binding of the compound in the absence of the plurality of compounds; and if so (d) separately determining the binding to the mammalian SNORF25 receptor of each compound included in the plurality of compounds, so as to thereby identify any compound included therein which specifically binds to the mammalian SNORF25 receptor.

This invention provides a method of screening a plurality of chemical compounds not known to bind to a mammalian SNORF25 receptor to identify a compound which specifically binds to the mammalian SNORF25 receptor, which comprises (a) contacting a membrane preparation from cells transfected with, and expressing, DNA encoding the mammalian SNORF25 receptor with the plurality of compounds not known to bind specifically to the mammalian SNORF25 receptor under conditions permitting binding of compounds known to bind to the mammalian SNORF25 receptor; (b) determining whether the binding of a compound known to bind to the mammalian SNORF25 receptor is reduced in the presence of the plurality of compounds, relative to the binding of the compound in the absence of the plurality of compounds; and if so (c) separately determining the binding to the mammalian SNORF25 receptor of each compound included in the plurality of compounds, so as to thereby identify any compound included therein which specifically binds to the mammalian SNORF25 receptor.

In one embodiment, the mammalian SNORF25 receptor is a human SNORF25 receptor. In a further embodiment, the mammalian SNORF25 receptor is a rat SNORF25 receptor. In another embodiment, the mammalian SNORF25 receptor is a mouse SNORF25 receptor. In another embodiment, the cell is a mammalian cell. In another embodiment, the mammalian cell is non-neuronal in origin. In a further embodiment, the non-neuronal cell is a COS-7 cell, a 293 human embryonic kidney cell, a LM(tk−) cell, a CHO cell, a mouse Y1 cell, or an NIH-3T3 cell.

This invention provides a method of detecting expression of a mammalian SNORF25 receptor by detecting the presence of mRNA coding for the mammalian SNORF25 receptor which comprises obtaining total mRNA from the cell and contacting the mRNA so obtained with a nucleic acid probe according to this invention under hybridizing conditions, detecting the presence of mRNA hybridized to the probe, and thereby detecting the expression of the mammalian SNORF25 receptor by the cell.

This invention provides a method of detecting the presence of a mammalian SNORF25 receptor on the surface of a cell which comprises contacting the cell with an antibody according to this invention under conditions permitting binding of the antibody to the receptor, detecting the presence of the antibody bound to the cell, and thereby detecting the presence of the mammalian SNORF25 receptor on the surface of the cell.

This invention provides a method of determining the physiological effects of varying levels of activity of mammalian SNORF25 receptors which comprises producing a transgenic, nonhuman mammal in accordance with this invention whose levels of mammalian SNORF25 receptor activity are varied by use of an inducible promoter which regulates mammalian SNORF25 receptor expression.

This invention provides a method of determining the physiological effects of varying levels of activity of mammalian SNORF25 receptors which comprises producing a panel of transgenic, nonhuman mammals in accordance with this invention each expressing a different amount of mammalian SNORF25 receptor.

This invention provides a method for identifying an antagonist capable of alleviating an abnormality wherein the abnormality is alleviated by decreasing the activity of a mammalian SNORF25 receptor comprising administering a compound to a transgenic, nonhuman mammal according to this invention, and determining whether the compound alleviates any physiological and/or behavioral abnormality displayed by the transgenic, nonhuman mammal as a result of overactivity of a mammalian SNORF25 receptor, the alleviation of such abnormality identifying the compound as an antagonist. In one embodiment, the mammalian SNORF25 receptor is a human SNORF25 receptor. In a further embodiment, the mammalian SNORF25 receptor is a rat SNORF25 receptor. In another embodiment, the mammalian SNORF25 receptor is a mouse SNORF25 receptor. The invention provides an antagonist identified by the preceding method according to this invention. This invention provides a composition, e.g. a pharmaceutical composition, comprising an antagonist according to this invention and a carrier, e.g. a pharmaceutically acceptable carrier. This invention provides a method of treating an abnormality in a subject wherein the abnormality is alleviated by decreasing the activity of a mammalian SNORF25 receptor which comprises administering to the subject an effective amount of the pharmaceutical composition according to this invention so as to thereby treat the abnormality.

This invention provides a method for identifying an agonist capable of alleviating an abnormality in a subject wherein the abnormality is alleviated by increasing the activity of a mammalian SNORF25 receptor comprising administering a compound to a transgenic, nonhuman mammal according to this invention, and determining whether the compound alleviates any physiological and/or behavioral abnormality displayed by the transgenic, nonhuman mammal, the alleviation of such an abnormality identifying the compound as an agonist. In one embodiment, the mammalian SNORF25 receptor is a human SNORF25 receptor. In a further embodiment, the mammalian SNORF25 receptor is a rat SNORF25 receptor. In another embodiment, the mammalian SNORF25 receptor is a mouse SNORF25 receptor. This invention provides an agonist identified by the preceding method according to this invention. This invention provides a composition, e.g. a pharmaceutical composition, comprising an agonist identified by the method according to this invention and a carrier, e.g. a pharmaceutically acceptable carrier.

This invention provides a method of treating an abnormality in a subject wherein the abnormality is alleviated by increasing the activity of a mammalian SNORF25 receptor which comprises administering to the subject an effective amount of the pharmaceutical composition according to this invention so as to thereby treat the abnormality.

This invention provides a method for diagnosing a predisposition to a disorder associated with the activity of a specific mammalian allele which comprises: (a) obtaining DNA of subjects suffering from the disorder; (b) performing a restriction digest of the DNA with a panel of restriction enzymes; (c) electrophoretically separating the resulting DNA fragments on a sizing gel; (d) contacting the resulting gel with a nucleic acid probe capable of specifically hybridizing with a unique sequence included within the sequence of a nucleic acid molecule encoding a mammalian SNORF25 receptor and labeled with a detectable marker; (e) detecting labeled bands which have hybridized to the DNA encoding a mammalian SNORF25 receptor to create a unique band pattern specific to the DNA of subjects suffering from the disorder; (f) repeating steps (a)–(e) with DNA obtained for diagnosis from subjects not yet suffering from the disorder; and (g) comparing the unique band pattern specific to the DNA of subjects suffering from the disorder from step (e) with the band pattern from step (f) for subjects not yet suffering from the disorder so as to determine whether the patterns are the same or different and thereby diagnose predisposition to the disorder if the patterns are the same.

In one embodiment, the disorder is a disorder associated with the activity of a specific mammalian allele is diagnosed.

This invention provides a method of preparing a purified mammalian SNORF25 receptor according to this invention which comprises: (a) culturing cells which express the mammalian SNORF25 receptor; (b) recovering the mammalian SNORF25 receptor from the cells; and (c) purifying the mammalian SNORF25 receptor so recovered.

This invention provides a method of preparing the purified mammalian SNORF25 receptor according to this invention which comprises: (a) inserting a nucleic acid encoding the mammalian SNORF25 receptor into a suitable expression vector; (b) introducing the resulting vector into a suitable host cell; (c) placing the resulting host cell in suitable conditions permitting the production of the mammalian SNORF25 receptor; (d) recovering the mammalian SNORF25 receptor so produced; and optionally (e) isolating and/or purifying the mammalian SNORF25 receptor so recovered.

This invention provides a process for determining whether a chemical compound is a mammalian SNORF25 receptor agonist which comprises contacting cells transfected with and expressing DNA encoding the mammalian SNORF25 receptor with the compound under conditions permitting the activation of the mammalian SNORF25 receptor, and detecting any increase in mammalian SNORF25 receptor activity, so as to thereby determine whether the compound is a mammalian SNORF25 receptor agonist.

This invention provides a process for determining whether a chemical compound is a mammalian SNORF25 receptor antagonist which comprises contacting cells transfected with and expressing DNA encoding the mammalian SNORF25 receptor with the compound in the presence of a known mammalian SNORF25 receptor agonist, under conditions permitting the activation of the mammalian SNORF25 receptor, and detecting any decrease in mammalian SNORF25 receptor activity, so as to thereby determine whether the compound is a mammalian SNORF25 receptor antagonist.

In one embodiment, the mammalian SNORF25 receptor is a human SNORF25 receptor. In another embodiment, the mammalian SNORF25 receptor is a rat SNORF25 receptor. In another embodiment, the mammalian SNORF25 receptor is a mouse SNORF25 receptor.

This invention provides a composition, for example a pharmaceutical composition, which comprises an amount of a mammalian SNORF25 receptor agonist determined by a process according to this invention effective to increase activity of a mammalian SNORF25 receptor and a carrier, for example, a pharmaceutically acceptable carrier. In one embodiment, the mammalian SNORF25 receptor agonist is not previously known.

This invention provides a composition, for example a pharmaceutical composition, which comprises an amount of a mammalian SNORF25 receptor antagonist determined by a process according to this invention effective to reduce activity of a mammalian SNORF25 receptor and a carrier, for example, a pharmaceutically acceptable carrier. In one embodiment, the mammalian SNORF25 receptor antagonist is not previously known.

This invention provides a process for determining whether a chemical compound specifically binds to and activates a mammalian SNORF25 receptor, which comprises contacting cells producing a second messenger response and expressing on their cell surface the mammalian SNORF25 receptor, wherein such cells do not normally express the mammalian SNORF25 receptor, with the chemical compound under conditions suitable for activation of the mammalian SNORF25 receptor, and measuring the second messenger response in the presence and in the absence of the chemical compound, a change, e.g. an increase, in the second messenger response in the presence of the chemical compound indicating that the compound activates the mammalian SNORF25 receptor.

In one embodiment, the second messenger response comprises chloride channel activation and the change in second messenger is an increase in the level of chloride current. In another embodiment, the second messenger response comprises change in intracellular calcium levels and the change in second messenger is an increase in the measure of intracellular calcium. In another embodiment, the second messenger response comprises release of inositol phosphate and the change in second messenger is an increase in the level of inositol phosphate. In another embodiment, the second messenger response comprises release of arachidonic acid and the change in second messenger is an increase in the level of arachidonic acid. In yet another embodiment, the second messenger response comprises GTPγS ligand binding and the change in second messenger is an increase in GTPγS ligand binding. In another embodiment, the second messenger response comprises activation of MAP kinase and the change in second messenger response is an increase in MAP kinase activation. In a further embodiment, the second messenger response comprises cAMP accumulation and the change in second messenger response is an increase in cAMP accumulation.

This invention provides a process for determining whether a chemical compound specifically binds to and inhibits activation of a mammalian SNORF25 receptor, which comprises separately contacting cells producing a second messenger response and expressing on their cell surface the mammalian SNORF25 receptor, wherein such cells do not normally express the mammalian SNORF25 receptor, with both the chemical compound and a second chemical compound known to activate the mammalian SNORF25 receptor, and with only the second chemical compound, under conditions suitable for activation of the mammalian SNORF25 receptor, and measuring the second messenger response in the presence of only the second chemical compound and in the presence of both the second chemical compound and the chemical compound, a smaller change, e.g. increase, in the second messenger response in the presence of both the chemical compound and the second chemical compound than in the presence of only the second chemical compound indicating that the chemical compound inhibits activation of the mammalian SNORF25 receptor.

In one embodiment, the second messenger response comprises chloride channel activation and the change in second messenger response is a smaller increase in the level of chloride current in the presence of both the chemical compound and the second chemical compound than in the presence of only the second chemical compound. In another embodiment, the second messenger response comprises change in intracellular calcium levels and the change in second messenger response is a smaller increase in the measure of intracellular calcium in the presence of both the chemical compound and the second chemical compound than in the presence of only the second chemical compound. In another embodiment, the second messenger response comprises release of inositol phosphate and the change in second messenger response is a smaller increase in the level of inositol phosphate in the presence of both the chemical compound and the second chemical compound than in the presence of only the second chemical compound.

In one embodiment, the second messenger response comprises activation of MAP kinase and the change in second messenger response is a smaller increase in the level of MAP kinase activation in the presence of both the chemical compound and the second chemical compound than in the presence of only the second chemical compound. In another embodiment, the second messenger response comprises change in cAMP levels and the change in second messenger response is a smaller change in the level of cAMP in the presence of both the chemical compound and the second chemical compound than in the presence of only the second chemical compound. In another embodiment, the second messenger response comprises release of arachidonic acid and the change in second messenger response is an increase in the level of arachidonic acid levels in the presence of both the chemical compound and the second chemical compound than in the presence of only the second chemical compound. In a further embodiment, the second messenger response comprises GTPγS ligand binding and the change in second messenger is a smaller increase in GTPγS ligand binding in the presence of both the chemical compound and the second chemical compound than in the presence of only the second chemical compound.

In one embodiment, the mammalian SNORF25 receptor is a human SNORF25 receptor. In a further embodiment, the mammalian SNORF25 receptor is a rat SNORF25 receptor. In another embodiment, the mammalian SNORF25 receptor is a mouse SNORF25 receptor. In another embodiment, the cell is an insect cell. In another embodiment, the cell is a mammalian cell. In another embodiment, the mammalian cell is nonneuronal in origin. In another embodiment, the nonneuronal cell is a COS-7 cell, CHO cell, 293 human embryonic kidney cell, NIH-3T3 cell or LM(tk–) cell. In another embodiment, the compound is not previously known to bind to a mammalian SNORF25 receptor.

In an embodiment of the invention, the second compound is a lipid-like molecule including, but not limited to, ATRA and phospholipids. Examples of phospholipids include, but are not limited to, PAF(C18), PAF(C16), lyso-PAF(C18) and lyso-PAF(C16).

This invention provides a compound determined by a process according to this invention and a composition, for example, a pharmaceutical composition, which comprises an amount of a mammalian SNORF25 receptor agonist determined to be such by a process according to this invention effective to increase activity of the mammalian SNORF25 receptor and a carrier, for example, a pharmaceutically acceptable carrier. In one embodiment, the mammalian SNORF25 receptor agonist is not previously known.

This invention provides a composition, for example, a pharmaceutical composition, which comprises an amount of a mammalian SNORF25 receptor antagonist determined to be such by a process according to this invention, effective to reduce activity of the mammalian SNORF25 receptor and a carrier, for example, a pharmaceutically acceptable carrier. In one embodiment, the mammalian SNORF25 receptor antagonist is not previously known.

This invention provides a method of screening a plurality of chemical compounds not known to activate a mammalian SNORF25 receptor to identify a compound which activates the mammalian SNORF25 receptor which comprises: (a) contacting cells transfected with and expressing the mammalian SNORF25 receptor with the plurality of compounds not known to activate the mammalian SNORF25 receptor, under conditions permitting activation of the mammalian SNORF25 receptor; (b) determining whether the activity of the mammalian SNORF25 receptor is increased in the presence of one or more of the compounds; and if so (c) separately determining whether the activation of the mammalian SNORF25 receptor is increased by any compound included in the plurality of compounds, so as to thereby identify each compound which activates the mammalian SNORF25 receptor. In one embodiment, the mammalian SNORF25 receptor is a human SNORF25 receptor. In a further embodiment, the mammalian SNORF25 receptor is a rat SNORF25 receptor. In another embodiment, the mammalian SNORF25 receptor is a mouse SNORF25 receptor.

This invention provides a method of screening a plurality of chemical compounds not known to inhibit the activation of a mammalian SNORF25 receptor to identify a compound which inhibits the activation of the mammalian SNORF25 receptor, which comprises: (a) contacting cells transfected with and expressing the mammalian SNORF25 receptor with the plurality of compounds in the presence of a known mammalian SNORF25 receptor agonist, under conditions permitting activation of the mammalian SNORF25 receptor; (b) determining whether the extent or amount of activation of the mammalian SNORF25 receptor is reduced in the presence of one or more of the compounds, relative to the extent or amount of activation of the mammalian SNORF25 receptor in the absence of such one or more compounds; and if so (c) separately determining whether each such compound inhibits activation of the mammalian SNORF25 receptor for each compound included in the plurality of compounds, so as to thereby identify any compound included in such plurality of compounds which inhibits the activation of the mammalian SNORF25 receptor.

In one embodiment, the mammalian SNORF25 receptor is a human SNORF25 receptor. In a further embodiment, the mammalian SNORF25 receptor is a rat SNORF25 receptor. In another embodiment, the mammalian SNORF25 receptor is a mouse SNORF25 receptor. In another embodiment, wherein the cell is a mammalian cell. In another embodiment, the mammalian cell is non-neuronal in origin. In another embodiment, the non-neuronal cell is a COS-7 cell, a 293 human embryonic kidney cell, a LM(tk−) cell or an NIH-3T3 cell.

This invention provides a composition, for example a pharmaceutical composition, comprising a compound identified by a method according to this invention in an amount effective to increase mammalian SNORF25 receptor activity and a carrier, for example, a pharmaceutically acceptable carrier.

This invention provides a composition, for example, a pharmaceutical composition, comprising a compound identified by a method according to this invention in an amount effective to decrease mammalian SNORF25 receptor activity and a carrier, for example, a pharmaceutically acceptable carrier.

This invention provides a method of treating an abnormality in a subject wherein the abnormality is alleviated by increasing the activity of a mammalian SNORF25 receptor which comprises administering to the subject a compound which is a mammalian SNORF25 receptor agonist in an amount effective to treat the abnormality. In one embodiment, the abnormality is a regulation of a steroid hormone disorder, an epinephrine release disorder, a gastrointestinal disorder, a cardiovascular disorder, an electrolyte balance disorder, hypertension, diabetes, a respiratory disorder, asthma, a reproductive function disorder, an immune disorder, an endocrine disorder, a musculoskeletal disorder, a neuroendocrine disorder, a cognitive disorder, a memory disorder, somatosensory and neurotransmission disorders, a motor coordination disorder, a sensory integration disorder, a motor integration disorder, a dopaminergic function disorder, an appetite disorder, such as anorexia or obesity, a sensory transmission disorder, an olfaction disorder, an autonomic nervous system disorder, pain, psychotic behavior, affective disorder, migraine, cancer, proliferative diseases, wound healing, tissue regeneration, blood coagulation-related disorders, developmental disorders, or ischemia-reperfusion injury-related diseases.

This invention provides a method of treating an abnormality in a subject wherein the abnormality is alleviated by decreasing the activity of a mammalian SNORF25 receptor which comprises administering to the subject a compound which is a mammalian SNORF25 receptor antagonist in an amount effective to treat the abnormality. In one embodiment, the abnormality is a regulation of a steroid hormone disorder, an epinephrine release disorder, a gastrointestinal disorder, a cardiovascular disorder, an electrolyte balance disorder, hypertension, diabetes, a respiratory disorder, asthma, a reproductive function disorder, an immune disorder, an endocrine disorder, a musculoskeletal disorder, a neuroendocrine disorder, a cognitive disorder, a memory disorder, somatosensory and neurotransmission disorders, a motor coordination disorder, a sensory integration disorder, a motor integration disorder, a dopaminergic function disorder, an appetite disorder, such as anorexia or obesity, a somatosensory neurotransmission disorder, an olfaction disorder, an autonomic nervous system disorder, pain, psychotic behavior, affective disorder, migraine, cancer, proliferative diseases, wound healing, tissue regeneration, blood coagulation-related disorders, developmental disorders, or ischemia-reperfusion injury-related diseases.

This invention provides a process for making a composition of matter which specifically binds to a mammalian SNORF25 receptor which comprises identifying a chemical compound using a process in accordance with this invention and then synthesizing the chemical compound or a novel structural and functional analog or homolog thereof. In one embodiment, the mammalian SNORF25 receptor is a human SNORF25 receptor.

In another embodiment, the mammalian SNORF25 receptor is a rat SNORF25 receptor. In another embodiment, the mammalian SNORF25 receptor is a mouse SNORF25 receptor.

This invention provides a process for preparing a composition, for example, a pharmaceutical composition which comprises admixing a carrier, for example, a pharmaceutically acceptable carrier, and a pharmaceutically effective amount of a chemical compound identified by a process in accordance with this invention or a novel structural and functional analog or homolog thereof. In one embodiment, the mammalian SNORF25 receptor is a human SNORF25 receptor. In another embodiment, the mammalian SNORF25 receptor is a rat SNORF25 receptor. In another embodiment, the mammalian SNORF25 receptor is a mouse SNORF25 receptor.

Thus, once the gene for a targeted receptor subtype is cloned, it is placed into a recipient cell which then expresses the targeted receptor subtype on its surface. This cell, which expresses a single population of the targeted human receptor subtype, is then propagated resulting in the establishment of a cell line. This cell line, which constitutes a drug discovery system, is used in two different types of assays: binding assays and functional assays. In binding assays, the affinity of a compound for both the receptor subtype that is the target of a particular drug discovery program and other receptor subtypes that could be associated with side effects are measured. These measurements enable one to predict the potency of a compound, as well as the degree of selectivity that the compound has for the targeted receptor subtype over other receptor subtypes. The data obtained from binding assays also enable chemists to design compounds toward or away from one or more of the relevant subtypes, as appropriate, for optimal therapeutic efficacy. In functional assays, the nature of the response of the receptor subtype to the compound is determined. Data from the functional assays show whether the compound is acting to inhibit or enhance the activity of the receptor subtype, thus enabling pharmacologists to evaluate compounds rapidly at their ultimate human receptor subtypes targets permitting chemists to rationally design drugs that will be more effective and have fewer or substantially less severe side effects than existing drugs.

Approaches to designing and synthesizing receptor subtype-selective compounds are well known and include traditional medicinal chemistry and the newer technology of combinatorial chemistry, both of which are supported by computer-assisted molecular modeling. With such approaches, chemists and pharmacologists use their knowledge of the structures of the targeted receptor subtype and compounds determined to bind and/or activate or inhibit activation of the receptor subtype to design and synthesize structures that will have activity at these receptor subtypes.

Combinatorial chemistry involves automated synthesis of a variety of novel compounds by assembling them using different combinations of chemical building blocks. The use of combinatorial chemistry greatly accelerates the process of generating compounds. The resulting arrays of compounds are called libraries and are used to screen for compounds ("lead compounds") that demonstrate a sufficient level of activity at receptors of interest. Using combinatorial chemistry it is possible to synthesize "focused" libraries of compounds anticipated to be highly biased toward the receptor target of interest.

Once lead compounds are identified, whether through the use of combinatorial chemistry or traditional medicinal chemistry or otherwise, a variety of homologs and analogs are prepared to facilitate an understanding of the relationship between chemical structure and biological or functional activity. These studies define structure activity relationships which are then used to design drugs with improved potency, selectivity and pharmacokinetic properties. Combinatorial chemistry is also used to rapidly generate a variety of structures for lead optimization. Traditional medicinal chemistry, which involves the synthesis of compounds one at a time, is also used for further refinement and to generate compounds not accessible by automated techniques. Once such drugs are defined the production is scaled up using standard chemical manufacturing methodologies utilized throughout the pharmaceutical and chemistry industry.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Materials and Methods

Mixed Oligonucleotide Primed Amplification of cDNA (MOPAC)

Mixed Oligonucleotide Primed Amplification of cDNA (MOPAC) was performed on several DNA templates including: rat genomic DNA, cDNA reverse-transcribed from mRNA isolated from the GH1 cell line, and the Rin14b cell line. The MOPAC reaction was performed using Taq DNA polymerase (Boehringer-Mannheim, Indianapolis, Ind.) and the following degenerate oligonucleotides: JAB55, designed based on the third transmembrane domain of the galanin, somatostatin, and opiate receptor families; and TL1020, designed based on the $7^{th}$ transmembrane domain of the galanin receptor family.

The conditions for the MOPAC PCR reaction were as follows: 3 minute hold at 94° C.; 10 cycles of 1 minute at 94° C., 1 minute 45 seconds at 44° C., 2 minutes at 72° C.; 30 cycles of 94° C. for 1 minute, 49° C. for 1 minute 45 seconds, 2 minutes at 72° C.; 4 minute hold at 72° C.; 4° C. hold until ready for agarose gel electrophoresis.

The products were run on a 1% agarose TAE gel and bands of the expected size (~500–600 bp) were cut from the gel, purified using the QIAQUICK gel extraction kit (QIAGEN, Chatsworth, Calif.), and subcloned into the TA cloning vector (Invitrogen, San Diego, Calif.). White (insert-containing) colonies were picked and subjected to PCR using pCR2.1 vector primers JAB1 and JAB2 using the following protocol: 94° C. hold for 3 minutes; 35 cycles of 94° C. for 1 minute, 68° C. for 1 minute 15 seconds; 2 minute hold at 68° C., 4° C. hold until the products were ready for purification. PCR products were purified by isopropanol precipitation (10 µl PCR product, 18 µl low TE, 10.5 µl 2M $NaClO_4$, and 21.5 µl isopropanol) and sequenced using the ABI Big Dye cycle sequencing protocol and ABI 377 sequencers (ABI, Foster City, Calif.). One of these PCR products, later named SNORF25, was determined to be a novel G protein-coupled receptor-like sequence based on database searches and its homology to other known G protein-coupled receptors (~29% identity to the known receptors dopamine D1, beta-adrenergic 2b and 5-HT1f; 34% identity to the 5-HT4l receptor).

5' and 3' RACE

To determine the full-length coding sequence of SNORF25, the Clontech Marathon cDNA Amplification kit (Clontech, Palo Alto, Calif.) for 5'/3' Rapid Amplification of cDNA ends (RACE) was utilized. Total RNA from Rin14b cells was PolyA+—selected using a FastTrack mRNA Isolation Kit (Invitrogen). For 5' RACE, double-stranded cDNA was synthesized from 1 g polyA+ RNA using primer JAB73, a reverse primer from the putative fifth transmembrane domain of the PCR fragment described above (SNORF25). Adaptor ligation and nested PCR were performed according to the Marathon cDNA Amplification protocol using Advantage Klentaq Polymerase (Clontech, Palo Alto, Calif.). The initial PCR was performed on a 50-fold dilution of the ligated cDNA using the supplier's Adaptor Primer 1 and JAB71, a reverse primer from the 5' end of the fifth transmembrane domain of the PCR fragment described above. One µl of this initial PCR reaction was re-amplified using the Adaptor Primer 2 and JAB69, a reverse primer just downstream of the fourth transmembrane domain. The conditions for PCR were 1 minute at 94° C.; 5 cycles of 94° C. for 15 seconds and 72° C. for 1 minute 30 seconds; 5 cycles of 94° C. for 15 seconds and 70° C. for 1 minute 30 seconds; 22 cycles of 94° C. for 15 seconds and 68° C. for 1 minute 30 seconds; 68° C. hold for 5 minutes, and 4° C. hold until the products were ready for analysis. A 600 bp fragment from the nested PCR was isolated from a 1% agarose TAE gel using the QIAQUICK kit and sequenced using ABI 377 sequencers and BigDye termination cycle sequencing as described above. Sequences were analyzed using the Wisconsin Package (GCG, Genetics Computer Group, Madison, Wis.).

For 3' RACE, double stranded cDNA was synthesized from 1 µg polyA$^+$ RNA using the cDNA synthesis primer CDS supplied with the Marathon cDNA Amplification Kit (Clontech). PCR conditions for the 3' RACE reactions were similar to the 5' RACE reactions, except that JAB74 and JAB72, forward primers from the sequence located between the fifth and sixth transmembrane domains of the novel PCR fragment from MOPAC described above, were used in place of JAB 71 and JAB73, respectively. A 1.4 kb fragment from the nested PCR was isolated from a 1% agarose TAE gel using the QIAQUICK gel purification kit (QIAGEN) and sequenced as above.

After determining the full-length coding sequence of this receptor sequence, the entire coding region was amplified from Rin14b cell line cDNA and rat genomic DNA using the Expand Long PCR system (Boehringer-Mannheim). The primers for this reaction were specific to the 5' and 3' untranslated regions of SNORF25 with BamHI and HindIII restriction sites incorporated into the 5' ends of the 5' (JAB86) and 3' (JAB84) primers, respectively. The products from this reaction were then digested with BamHI and HindIII, subcloned into the BamHI/HindIII site of the expression vector pcDNA3.1 (–), and sequenced in both directions using vector- and gene-specific primers. Double-stranded sequence from the Rin14b-cloned SNORF25 product agreed with the sequence of the same gene amplified from rat genomic DNA. This receptor/expression vector construct of rat SNORF25 in pcDNA3.1(–) was named pcDNA3.1-rSNORF25.

Homology Cloning of the Human Homolog of SNORF25

To clone the human homolog of SNORF25, two oligonucleotide probes were designed based on the second (BB426) and fifth (BB427) transmembrane domains (TMs) of the rat SNORF25 sequence, and used to probe a human genomic cosmid library (Clontech). Both primers were end-labeled with α$^{32}$P-DATP and terminal transferase (Promega, Madison, Wis.). Hybridization was performed under medium stringency conditions: 40° C. in a solution containing 37.5% formamide 5×SSC (1×SSC is 0.15M sodium chloride, 0.015M sodium citrate), 1×Denhardt's solution (0.02% polyvinylpyrrolindone, 0.02% Ficoll, 0.02% bovine serum albumin), 7 mM Tris, and 25 µg/ml sonicated salmon sperm DNA. The filters were washed three times for 20 minutes at room temperature in a buffer containing 2×SSC/0.1% sodium dodecyl sulfate; two times for 20 minutes in a buffer containing 0.1×SSC/0.1% sodium dodecyl sulfate, and exposed at –70° C. to Kodak BioMax MS film in the presence of an intensifying screen.

Cosmid clones hybridizing with the probes were picked, streaked on plates, and screened a second time with the same probes to verify and isolate the individual positive colonies under the same conditions. Cosmid DNA from positive colonies was digested with BamHI and HindIII, run on an agarose gel, transferred to nitrocellulose, and probed with $^{32}$P-labelled BB426. A fragment of approximately 1.9 kb from clone #45a (COS4 library) that hybridized to the probe was subcloned into the BamHI/HindIII site of pEXJT3T7, an Okayama and Berg expression vector modified from pcEXV (Miller and Germain, 1986) to contain BstXI and other additional restriction sites as well as T3 and T7 promoters (Stratagene), and sequenced on both strands as described above. The construct of the human SNORF25 receptor in this vector is named pEXJT3T7-hSNORF25. Human SNORF25 was analyzed using the GCG software and was determined to contain the full-length sequence of human SNORF25, having 80% amino acid identity and 83% nucleotide identity to the rat receptor.

Oligonucleotide Primers

The following is a list of primers and their associated sequences which were used in the cloning of these receptors:

```
                                              (SEQ ID NO:5)
JAB55:   5'-TBDSYVYIGAYMGITAYVTKG-3'

(SEQ ID NO:6)
TL1020:  5'-GAIRSIARIGMRTAIAYIAKIGGRTT-3'

(SEQ ID NO:7)
JAB1:    5'-TTATGCTTCCGGCTCGTATGTTGTG-3'

(SEQ ID NO:8)
JAB2:    5'-ATGTGCTGCAAGGCGATTTAAGTTGGG-3'

(SEQ ID NO:9)
JAB69:   5'-TGGTCTGCTGGAATATGGAG-3'

(SEQ ID NO:10)
JAB71:   5'-CTTGGGTGAAACACAGCAAAGAAGG-3'

(SEQ ID NO:11)
JAB72:   5'-ATGGAACATGCAGGAGCCATGGTTGG-3'

(SEQ ID NO:12)
JAB73:   5'-AAGACAAAGAGGAGCACAGCTGGG-3'

(SEQ ID NO:13)
JAB74:   5'-GCTCAAGATTGCCTCTGTGCACAG-3'

(SEQ ID NO:14)
JAB84:   5'-ATCTATAAGCTTAGGCACTTGGAAACATCCATTCC- 3'

(SEQ ID NO:15)
JAB86:   5'-ATCTATGGATCCTGTGAGAATCTGAGCTCAAGACCC-3'

(SEQ ID NO:16)
BB426:   5'-TTCACCTTAAATCTGGCCGTGGCTGATACCTTGAT-
         TGGCGTGGCTATTTCTGGGCTAG-3'

(SEQ ID NO:17)
BB427:   5'-GCTGTGTTTCACCCAAGGTTTGTGCTGACCCTCTC-
         CTGTGCTGGCTTCTTCCCAGCTGTGC-3'
```

Isolation of a Fragment of the Mouse SNORF25

Two primers, JAB680 (forward) and JAB681 (reverse), were designed in the 1st and 7th transmembrane domains (respectively) of SNORF25 to obtain a mouse fragment by PCR. These primers were chosen based on an alignment of the human and rat SNORF25 DNA sequences, in regions that were 100% identical between the two species. Mouse genomic DNA (0.1 ug) was subjected to PCR with JAB680 and JAB681 using Expand Long and an Eppendorf Mastercycler Gradient PCR machine with a block gradient of 40–60° C. A band of approximately 820 bp was obtained by the following PCR protocol (94° C. for 3 minutes; 40 cycles of 94° C. for 45 seconds, 56° C. for 1 minute thirty seconds, 68° C. for 2 minutes; 68° C. for 4 minutes, and 4° C. hold until the products were size-separated on a 1% agarose gel in 1×TAE), and gel purified using the QIAQUICK PCR purification kit (QIAGEN, Valencia, Calif.). Purified DNA was cloned into the TA cloning kit (Invitrogen, Carlsbad, Calif.), and plasmid DNA from insert-containing colonies was purified using the QIAPREP SPIN miniprep kits from QIAGEN. Inserts were sequenced using the ABI Big Dye cycle sequencing protocol and ABI 377 sequencers (ABI, Foster City, Calif.) with T7 and M13 sequencing primers. Sequence analysis using the Wisconsin Package (GCG, Genetics Computer Group, Madison, Wis.) and Sequencher 3.0.1 indicated that this 820 bp band represented a fragment of the mouse homolog of SNORF25.

Isolation of the Full-Length Mouse SNORF25

A mouse genomic phage library (Clontech, Palo Alto, Calif.) was screened under high stringency conditions using a $^{32}$P-labeled oligonucleotide probe, JAB734, designed based on the mouse SNORF25 fragment. JAB734 was end-labeled with a $^{32}$P-DATP and terminal transferase (Promega, Madison, Wis.). Hybridization of nitrocellulose filter overlays of the plates was performed at 40° C. in a solution containing 50% formamide, 5×SSC (1×SSC is 0.15M sodium chloride, 0.015M sodium citrate), 1×Denhardt's solution (0.02% polyvinylpyrrolindone, 0.02% Ficoll, 0.02% bovine serum albumin), 7 mM Tris, and 25 µg/ml sonicated salmon sperm DNA. The filters were washed at 50° C. in 0.1×SSC containing 0.5% sodium dodecyl sulfate and exposed at −90° C. to Kodak BioMax film in the presence of an intensifying screen.

A positive signal was isolated on a secondary plating and labeled clone 1a. A 2.5 kb fragment from a BglII digest was identified by Southern blot analysis, subcloned into the BamHI site of pEXJ, and named B0148. The sequence of this construct was determined as described above. This construct of the mouse SNORF25 was renamed pEXJ-mSNORF25-f.

Oligonucleotide Primers

The following is a list of primers and their associated sequences which were used in the cloning of the SNORF25 mouse receptor:

```
                                                 (SEQ ID NO:26)
JAB680 5'-CTCATTTGGAGTGATCCTTGCTGTCC-3'

(SEQ ID NO:27)
JAB681 5'-ACATGAGTGGGTTGAGCAGGGAGTT-3'

(SEQ ID NO:28)
JAB734 5'-GAAGACCTTGTGTAGCCTTCGGATGGCATTTGTCACTTCTT
       CTGCAGCTGC-3'
```

Isolation of Other Species Homologs of SNORF25 RECEPTOR cDNA

A nucleic acid sequence encoding a SNORF25 receptor cDNA from other species may be isolated using standard molecular biology techniques and approaches such as those described below:

Approach #1: A genomic library (e.g., cosmid, phage, P1, BAC, YAC) generated from the species of interest may be screened with a $^{32}$P-labeled oligonucleotide probe corresponding to a fragment of the human or rat SNORF25 receptors whose sequence is shown in FIGS. 1A–1B and 3A–3B to isolate a genomic clone. The full-length sequence may be obtained by sequencing this genomic clone. If one or more introns are present in the gene, the full-length intronless gene may be obtained from cDNA using standard molecular biology techniques. For example, a forward PCR primer designed in the 5'UT and a reverse PCR primer designed in the 3'UT may be used to amplify a full-length, intronless receptor from cDNA. Standard molecular biology techniques could be used to subclone this gene into a mammalian expression vector.

Approach #2: Standard molecular biology techniques may be used to screen commercial cDNA phage libraries of the species of interest by hybridization under reduced stringency with a $^{32}$P-labeled oligonucleotide probe corresponding to a fragment of the sequences shown in FIGS. 1A–1B or 3A–3B. One may isolate a full-length SNORF25 receptor by obtaining a plaque purified clone from the lambda libraries and then subjecting the clone to direct DNA sequencing. Alternatively, standard molecular biology techniques could be used to screen cDNA plasmid libraries by PCR amplification of library pools using primers designed against a partial species homolog sequence. A full-length clone may be isolated by Southern hybridization of colony lifts of positive pools with a $^{32}$P-oligonucleotide probe.

Approach #3: 3' and 5' RACE may be utilized to generate PCR products from cDNA derived from the species of interest expressing SNORF25 which contain the additional sequence of SNORF25. These RACE PCR products may then be sequenced to determine the additional sequence. This new sequence is then used to design a forward PCR primer in the 5'UT and a reverse primer in the 3'UT. These primers are then used to amplify a full-length SNORF25 clone from cDNA.

Examples of other species include, but are not limited to, dog, monkey, hamster and guinea pig.

Host Cells

A broad variety of host cells can be used to study heterologously expressed proteins. These cells include but are not limited to mammalian cell lines such as; Cos-7, CHO, LM(tk⁻), HEK293, etc.; insect cell lines such as; Sf9, Sf21, etc.; amphibian cells such as *Xenopus* oocytes; assorted yeast strains; assorted bacterial cell strains; and others. Culture conditions for each of these cell types is specific and is known to those familiar with the art. The cells used to express SNORF25 receptor were Cos-7 and Chinese hamster ovary (CHO) cells.

COS-7 cells are grown on 150 mm plates in DMEM with supplements (Dulbecco's Modified Eagle Medium with 10% bovine calf serum, 4 mM glutamine, 100 units/ml penicillin/100 µg/ml streptomycin) at 37° C., 5% $CO_2$. Stock plates of COS-7 cells are trypsinized and split 1:6 every 3–4 days.

CHO cells are grown on 150 mm plates in HAM's F-12 medium with supplements (10% bovine calf serum, 4 mM L-glutamine and 100 units/ml penicillin/100 µg/ml streptomycin) at 37° C., 5% $CO_2$. Stock plates of CHO cells are trypsinized and split 1:8 every 3–4 days.

Transient Expression

DNA encoding proteins to be studied can be transiently expressed in a variety of mammalian, insect, amphibian, yeast, bacterial and other cell lines by several methods, such as, calcium phosphate-mediated, DEAE-dextran mediated, liposomal-mediated, viral-mediated, electroporation-mediated and microinjection delivery. Each of these methods may require optimization of assorted experimental parameters depending on the DNA, cell line, and the type of assay to be subsequently employed. The electroporation method was used to transiently transfect various cell lines with SNORF25 cDNA.

A typical protocol for the electroporation method as applied to Cos-7 cells is described as follows. Cells to be used for transfection are split 24 hours prior to the transfection to provide flasks which are subconfluent at the time of transfection. The cells are harvested by trypsinization resuspended in their growth media and counted. $5 \times 10^6$ cells are suspended in 300 µl of DMEM and placed into an electroporation cuvette. 8 µg of receptor DNA plus 8 µg of any additional DNA needed (e.g. G protein expression vector, reporter construct, antibiotic resistance marker, mock vector, etc.) is added to the cell suspension, the cuvette is placed into a BioRad Gene Pulser and subjected to an electrical pulse (Gene Pulser settings: 0.25 kV voltage, 950 µF capacitance). Following the pulse, 800 µl of complete DMEM is added to each cuvette and the suspension transferred to a sterile tube. Complete medium is added to each tube to bring the final cell concentration to $1 \times 10^5$ cells/100 µl. The cells are then plated as needed depending upon the type of assay to be performed.

Stable Expression

Heterologous DNA can be stably incorporated into host cells, causing the cell to perpetually express a foreign protein. Methods for the delivery of the DNA into the cell are similar to those described above for transient expression but require the co-transfection of an ancillary gene to confer drug resistance on the targeted host cell. The ensuing drug resistance can be exploited to select and maintain cells that have taken up the DNA. An assortment of resistance genes are available including but not restricted to neomycin, kanamycin, and hygromycin. For the purposes of studies concerning the receptor of this invention, stable expression of a heterologous receptor protein is typically carried out in, mammalian cells including but not necessarily restricted to, CHO, HEK293, LM(tk−), etc.

In addition native cell lines that naturally carry and express the nucleic acid sequences for the receptor may be used without the need to engineer the receptor complement.

Membrane Preparations

Cell membranes expressing the receptor protein according to this invention are useful for certain types of assays including but not restricted to ligand binding assays, GTP-γ-S binding assays, and others. The specifics of preparing such cell membranes may in some cases be determined by the nature of the ensuing assay but typically involve harvesting whole cells and disrupting the cell pellet by sonication in ice cold buffer (e.g. 20 mM Tris-HCl, 5 mM EDTA, pH 7.4). The resulting crude cell lysate is cleared of cell debris by low speed centrifugation at 200×g for 5 min at 4° C. The cleared supernatant is then centrifuged at 40,000×g for 20 min at 4° C., and the resulting membrane pellet is washed by suspending in ice cold buffer and repeating the high speed centrifugation step. The final washed membrane pellet is resuspended in assay buffer. Protein concentrations are determined by the method of Bradford (1976) using bovine serum albumin as a standard. The membranes may be used immediately or frozen for later use.

Generation of Baculovirus

The coding region of DNA encoding the human receptor disclosed herein may be subcloned into pBlueBacIII into existing restriction sites or sites engineered into sequences 5' and 3' to the coding region of the polypeptides. To generate baculovirus, 0.5 µg of viral DNA (BaculoGold) and 3 µg of DNA construct encoding a polypeptide may be co-transfected into $2 \times 10^6$ *Spodoptera frugiperda* insect Sf9 cells by the calcium phosphate co-precipitation method, as outlined by Pharmingen (in "Baculovirus Expression Vector System: Procedures and Methods Manual"). The cells then are incubated for 5 days at 27° C.

The supernatant of the co-transfection plate may be collected by centrifugation and the recombinant virus plaque purified. The procedure to infect cells with virus, to prepare stocks of virus and to titer the virus stocks are as described in Pharmingen's manual.

Labeled Ligand Binding Assays

Cells expressing the receptor according to this invention may be used to screen for ligands for said receptors, for example, by labeled ligand binding assays. Once a ligand is identified the same assays may be used to identify agonists or antagonists of the receptor that may be employed for a variety of therapeutic purposes.

In an embodiment, labeled ligands are placed in contact with either membrane preparations or intact cells expressing the receptor in multi-well microtiter plates, together with unlabeled compounds, and binding buffer. Binding reaction mixtures are incubated for times and temperatures determined to be optimal in separate-equilibrium binding assays. The reaction is stopped by filtration through GF/B filters, using a cell harvester, or by directly measuring the bound ligand. If the ligand was labeled with a radioactive isotope such as $^3H$, $^{14}C$, $^{125}I$, $^{35}S$, $^{32}P$, $^{33}P$, etc., the bound ligand may be detected by using liquid scintillation counting, scintillation proximity, or any other method of detection for radioactive isotopes. If the ligand was labeled with a fluorescent compound, the bound labeled ligand may be measured by methods such as, but not restricted to, fluorescence intensity, time resolved fluorescence, fluorescence polarization, fluorescence transfer, or fluorescence correlation spectroscopy. In this manner agonist or antagonist compounds that bind to the receptor may be identified as they inhibit the binding of the labeled ligand to the membrane protein or intact cells expressing the receptor. Non-specific binding is defined as the amount of labeled ligand remaining after incubation of membrane protein in the presence of a high concentration (e.g., $100-1000 \times K_D$) of unlabeled ligand. In equilibrium saturation binding assays membrane preparations or intact cells transfected with the receptor are incubated in the presence of increasing concentrations of the labeled compound to determine the binding affinity of the labeled ligand. The binding affinities of unlabeled compounds may be determined in equilibrium competition binding assays, using a fixed concentration of labeled compound in the presence of varying concentrations of the displacing ligands.

Functional Assays

Cells expressing the SNORF25 receptor DNA may be used to screen for ligands to SNORF25 receptor using functional assays. Once a ligand is identified the same assays may be used to identify agonists or antagonists of the SNORF25 receptor that may be employed for a variety of therapeutic purposes. It is well known to those in the art that the overexpression of a GPCR can result in the constitutive activation of intracellular signaling pathways. In the same manner, overexpression of the SNORF25 receptor in any cell line as described above, can result in the activation of the functional responses described below, and any of the assays herein described can be used to screen for both agonist and antagonist ligands of the SNORF25 receptor.

A wide spectrum of assays can be employed to screen for the presence of SNORF25 receptor ligands. These assays range from traditional measurements of total inositol phosphate accumulation, cAMP levels, intracellular calcium mobilization, and potassium currents, for example; to systems measuring these same second messengers but which have been modified or adapted to be of higher throughput, more generic and more sensitive; to cell based assays reporting more general cellular events resulting from receptor activation such as metabolic changes, differentiation, cell division/proliferation. Description of several such assays follow.

Cyclic AMP (cAMP) Assay

The receptor-mediated stimulation or inhibition of cyclic AMP (cAMP) formation may be assayed in cells expressing the receptors. According to one method, cells are plated in 96-well plates or other vessels and preincubated in a buffer such as HEPES buffered saline (NaCl (150 mM), $CaCl_2$ (1mM), KCl (5 mM), glucose (10 mM)) supplemented with a phosphodiesterase inhibitor such as 5 mM theophylline, with or without protease inhibitor cocktail (For example, a typical inhibitor cocktail contains 2 µg/ml aprotinin, 0.5 mg/ml leupeptin, and 10 µg/ml phosphoramidon.) for 20 min at 37° C., in 5% $CO_2$. Test compounds are added with or without 10 mM forskolin and incubated for an additional 10 min at 37° C. The medium is then aspirated and the reaction stopped by the addition of 100 mM HCl or other methods. The plates are stored at 4° C. for 15 min, and the cAMP content in the stopping solution is measured by radioimmunoassay. Radioactivity may be quantified using a gamma counter equipped with data reduction software. Specific modifications may be performed to optimize the assay for the receptor or to alter the detection method of cAMP.

According to a second method, cells are washed 2 times with HEPES buffered saline, as described above, and incubated overnight. On the day of the experiment, cells are washed 2 times with HEPES supplemented with a phosphodiesterase inhibitor such as 5 mM theophylline, with or without protease inhibitor cocktail (For example, a typical inhibitor cocktail contains 2 µg/ml aprotinin, 0.5 mg/ml leupeptin, and 10 µg/ml phosphoramidon.) for 20 min at 37° C., in 5% $CO_2$. Test compounds are added with or without 10 mM forskolin and incubated for an additional 10 min at 37° C. The medium is then aspirated and the reaction stopped by the addition of 100 mM HCl or other methods. The plates are stored at 4° C. for 15 min, and the cAMP content in the stopping solution is measured by radioimmunoassay. Radioactivity may be quantified using a gamma counter equipped with data reduction software. Specific modifications may be performed to optimize the assay for the receptor or to alter the detection method of cAMP.

Arachidonic Acid Release Assay

Cells expressing the receptor are seeded into 96 well plates or other vessels and grown for 3 days in medium with supplements. $^3$H-arachidonic acid (specific activity=0.75 µCi/ml) is delivered as a 100 µL aliquot to each well and samples are incubated at 37° C., 5% $CO_2$ for 18 hours. The labeled cells are washed three times with medium. The wells are then filled with medium and the assay is initiated with the addition of test compounds or buffer in a total volume of 250 µL. Cells are incubated for 30 min at 37° C., 5% $CO_2$. Supernatants are transferred to a microtiter plate and evaporated to dryness at 75° C. in a vacuum oven. Samples are then dissolved and resuspended in 25 µL distilled water. Scintillant (300 µL) is added to each well and samples are counted for $^3$H in a Trilux plate reader. Data are analyzed using nonlinear regression and statistical techniques available in the GraphPAD Prism package (San Diego, Calif.).

Inositol Phosphate Assay

SNORF25 receptor-mediated activation of the inositol phosphate (IP) second messenger pathways can be assessed by radiometric measurement of IP products.

In a 96 well microplate format assay, cells are plated at a density of 70,000 cells per well and allowed to incubate for 24 hours. The cells are then labeled with 0.5 µCi [$^3$H]-myo-inositol overnight at 37° C., 5% $CO_2$. Immediately before the assay, the medium is removed and replaced with 90 µL of PBS containing 10 mM LiCl. The plates are then incubated for 15 min at 37° C., 5% $CO_2$. Following the incubation, the cells are challenged with agonist (10 µl/well; 10× concentration) for 30 min at 37° C., 5% $CO_2$. The challenge is terminated by the addition of 100 µL of 50% v/v trichloroacetic acid, followed by incubation at 4° C. for greater than 30 minutes. Total IPs are isolated from the lysate by ion exchange chromatography. Briefly, the lysed contents of the wells are transferred to a Multiscreen HV filter plate (Millipore) containing Dowex AG1-X8 (200–400 mesh, formate form). The filter plates are prepared adding 100 µL of Dowex AG1-X8 suspension (50% v/v, water: resin) to each well. The filter plates are placed on a vacuum manifold to wash or elute the resin bed. Each well is first washed 2 times with 200 µl of 5 mM myo-inositol. Total [$^3$H]inositol phosphates are eluted with 75 µl of 1.2M ammonium formate/0.1M formic acid solution into 96-well plates. 200 µL of scintillation cocktail is added to each well, and the radioactivity is determined by liquid scintillation counting.

Intracellular Calcium Mobilization Assays

The intracellular free calcium concentration may be measured by microspectrofluorimetry using the fluorescent indicator dye Fura-2/AM (Bush et al, 1991). Cells expressing the receptor are seeded onto a 35 mm culture dish containing a glass coverslip insert and allowed to adhere overnight. Cells are then washed with HBS and loaded with 100 µL of Fura-2/AM (10 µM) for 20 to 40 min. After washing with HBS to remove the Fura-2/AM solution, cells are equilibrated in HBS for 10 to 20 min. Cells are then visualized under the 40× objective of a Leitz Fluovert FS microscope and fluorescence emission is determined at 510 nM with excitation wavelengths alternating between 340 nM and 380 nM. Raw fluorescence data are converted to calcium concentrations using standard calcium concentration curves and software analysis techniques.

In another method, the measurement of intracellular calcium can also be performed on a 96-well (or higher) format and with alternative calcium-sensitive indicators, preferred examples of these are: aequorin, Fluo-3, Fluo-4, Fluo-5, Calcium Green-1, Oregon Green, and 488 BAPTA. After activation of the receptors with agonist ligands the emission elicited by the change of intracellular calcium concentration can be measured by a luminometer, or a fluorescence imager; a preferred example of this is the fluorescence imager plate reader (FLIPR).

Cells expressing the receptor of interest are plated into clear, flat-bottom, black-wall 96-well plates (Costar) at a density of 80,000–150,000 cells per well and allowed to incubate for 48 hr at 5% $CO_2$, 37° C. The growth medium is aspirated and 100 µl of loading medium containing fluo-3 dye is added to each well. The loading medium contains: Hank's BSS (without phenol red) (Gibco), 20 mM HEPES (Sigma), 0.1 or 1% BSA (Sigma), dye/pluronic acid mixture (e.g. 1 mM Flou-3, AM (Molecular Probes) and 10% pluronic acid (Molecular Probes) mixed immediately before use), and 2.5 mM probenecid (Sigma) (prepared fresh). The cells are allowed to incubate for about 1 hour at 5% $CO_2$, 37° C.

During the dye loading incubation the compound plate is prepared. The compounds are diluted in wash buffer (Hank's BSS (without phenol red), 20 mM HEPES, 2.5 mM probenecid) to a 4× final concentration and aliquoted into a clear v-bottom plate (Nunc). Following the incubation the cells are washed to remove the excess dye. A Denley plate washer is used to gently wash the cells 4 times and leave a 100

µl final volume of wash buffer in each well. The cell plate is placed in the center tray and the compound plate is placed in the right tray of the FLIPR. The FLIPR software is setup for the experiment, the experiment is run and the data are collected. The data are then analyzed using an excel spreadsheet program.

Antagonist ligands are identified by the inhibition of the signal elicited by agonist ligands.

GTPγS Functional Assay

Membranes from cells expressing the receptor are suspended in assay buffer (e.g., 50 mM Tris, 100 mM NaCl, 5 mM $MgCl_2$, 10 µM GDP, pH 7.4) with or without protease inhibitors (e.g., 0.1% bacitracin). Membranes are incubated on ice for 20 minutes, transferred to a 96-well Millipore microtiter GF/C filter plate and mixed with GTPγ$^{35}$S (e.g., 250,000 cpm/sample, specific activity ~1000 Ci/mmol) plus or minus unlabeled GTPγS (final concentration=100 µM). Final membrane protein concentration=90 µg/ml. Samples are incubated in the presence or absence of test compounds for 30 min. at room temperature, then filtered on a Millipore vacuum manifold and washed three times with cold (4° C.) assay buffer. Samples collected in the filter plate are treated with scintillant and counted for $^{35}$S in a Trilux (Wallac) liquid scintillation counter. It is expected that optimal results are obtained when the receptor membrane preparation is derived from an appropriately engineered heterologous expression system, i.e., an expression system resulting in high levels of expression of the receptor and/or expressing G-proteins having high turnover rates (for the exchange of GDP for GTP). GTPγS assays are well-known to those skilled in the art, and it is contemplated that variations on the method described above, such as are described by Tian et al. (1994) or Lazareno and Birdsall (1993), may be used.

Microphysiometric Assay

Because cellular metabolism is intricately involved in a broad range of cellular events (including receptor activation of multiple messenger pathways), the use of microphysiometric measurements of cell metabolism can in principle provide a generic assay of cellular activity arising from the activation of any receptor regardless of the specifics of the receptor's signaling pathway.

General guidelines for transient receptor expression, cell preparation and microphysiometric recording are described elsewhere (Salon, J. A. and Owicki, J. A., 1996). Typically cells expressing receptors are harvested and seeded at 3×10$^5$ cells per microphysiometer capsule in complete media 24 hours prior to an experiment. The media is replaced with serum free media 16 hours prior to recording to minimize non-specific metabolic stimulation by assorted and ill-defined serum factors. On the day of the experiment the cell capsules are transferred to the microphysiometer and allowed to equilibrate in recording media (low buffer RPMI 1640, no bicarbonate, no serum (Molecular Devices Corporation, Sunnyvale, Calif.) containing 0.1% fatty acid free BSA), during which a baseline measurement of basal metabolic activity is established.

A standard recording protocol specifies a 100 µl/min flow rate, with a 2 min total pump cycle which includes a 30 sec flow interruption during which the acidification rate measurement is taken. Ligand challenges involve a 1 min 20 sec exposure to the sample just prior to the first post challenge rate measurement being taken, followed by two additional pump cycles for a total of 5 min 20 sec sample exposure. Typically, drugs in a primary screen are presented to the cells at 10 µM final concentration. Follow up experiments to examine dose-dependency of active compounds are then done by sequentially challenging the cells with a drug concentration range that exceeds the amount needed to generate responses ranging from threshold to maximal levels. Ligand samples are then washed out and the acidification rates reported are expressed as a percentage increase of the peak response over the baseline rate observed just prior to challenge.

MAP Kinase Assay

MAP kinase (mitogen activated kinase) may be monitored to evaluate receptor activation. MAP kinase is activated by multiple pathways in the cell. A primary mode of activation involves the ras/raf/MEK/MAP kinase pathway. Growth factor (tyrosine kinase) receptors feed into this pathway via SHC/Grb-2/SOS/ras. Gi coupled receptors are also known to activate ras and subsequently produce an activation of MAP kinase. Receptors that activate phospholipase C (such as Gq/G11-coupled) produce diacylglycerol (DAG) as a consequence of phosphatidyl inositol hydrolysis. DAG activates protein kinase C which in turn phosphorylates MAP kinase.

MAP kinase activation can be detected by several approaches. One approach is based on an evaluation of the phosphorylation state, either unphosphorylated (inactive) or phosphorylated (active). The phosphorylated protein has a slower mobility in SDS-PAGE and can therefore be compared with the unstimulated protein using Western blotting. Alternatively, antibodies specific for the phosphorylated protein are available (New England Biolabs) which can be used to detect an increase in the phosphorylated kinase. In either method, cells are stimulated with the test compound and then extracted with Laemmli buffer. The soluble fraction is applied to an SDS-PAGE gel and proteins are transferred electrophoretically to nitrocellulose or Immobilon. Immunoreactive bands are detected by standard Western blotting technique. Visible or chemiluminescent signals are recorded on film and may be quantified by densitometry.

Another approach is based on evaluation of the MAP kinase activity via a phosphorylation assay. Cells are stimulated with the test compound and a soluble extract is prepared. The extract is incubated at 30° C. for 10 min with gamma-$^{32}$P-ATP, an ATP regenerating system, and a specific substrate for MAP kinase such as phosphorylated heat and acid stable protein regulated by insulin, or PHAS-I. The reaction is terminated by the addition of $H_3PO_4$ and samples are transferred to ice. An aliquot is spotted onto Whatman P81 chromatography paper, which retains the phosphorylated protein. The chromatography paper is washed and counted for $^{32}$P in a liquid scintillation counter. Alternatively, the cell extract is incubated with gamma-$^{32}$P-ATP, an ATP regenerating system, and biotinylated myelin basic protein bound by streptavidin to a filter support. The myelin basic protein is a substrate for activated MAP kinase. The phosphorylation reaction is carried out for 10 min at 30° C. The extract can then by aspirated through the filter, which retains the phosphorylated myelin basic protein. The filter is washed and counted for $^{32}$P by liquid scintillation counting.

Cell Proliferation Assay

Receptor activation of the receptor may lead to a mitogenic or proliferative response which can be monitored via $^3$H-thymidine uptake. When cultured cells are incubated with $^3$H-thymidine, the thymidine translocates into the nuclei where it is phosphorylated to thymidine triphosphate. The nucleotide triphosphate is then incorporated into the cellular DNA at a rate that is proportional to the rate of cell growth. Typically, cells are grown in culture for 1–3 days. Cells are forced into quiescence by the removal of serum for 24 hrs. A mitogenic agent is then added to the media. Twenty-four hours later, the cells are incubated with $^3$H-thymidine at specific activities ranging from 1 to 10 μCi/ml for 2–6 hrs. Harvesting procedures may involve trypsinization and trapping of cells by filtration over GF/C filters with or without a prior incubation in TCA to extract soluble thymidine. The filters are processed with scintillant and counted for $^3$H by liquid scintillation counting. Alternatively, adherent cells are fixed in MeOH or TCA, washed in water, and solubilized in 0.05% deoxycholate/0.1 N NaOH. The soluble extract is transferred to scintillation vials and counted for $^3$H by liquid scintillation counting.

Alternatively, cell proliferation can be assayed by measuring the expression of an endogenous or heterologous gene product, expressed by the cell line used to transfect the receptor, which can be detected by methods such as, but not limited to, florescence intensity, enzymatic activity, immunoreactivity, DNA hybridization, polymerase chain reaction, etc.

Promiscuous Second Messenger Assays

It is not possible to predict, a priori and based solely upon the GPCR sequence, which of the cell's many different signaling pathways any given receptor will naturally use. It is possible, however, to coax receptors of different functional classes to signal through a pre-selected pathway through the use of promiscuous $G_\alpha$ subunits. For example, by providing a cell based receptor assay system with an endogenously supplied promiscuous $G_l$ subunit such as $G_{\alpha15}$ or $G_{\alpha16}$ or a chimeric $G_\alpha$ subunit such as $G_{\alpha qz}$, a GPCR, which might normally prefer to couple through a specific signaling pathway (e.g., $G_s$, $G_l$, $G_q$, $G_0$, etc.), can be made to couple through the pathway defined by the promiscuous $G_\alpha$ subunit and upon agonist activation produce the second messenger associated with that subunit's pathway. In the case of $G_{\alpha15}$, $G_{\alpha16}$ and/or $G_{\alpha qz}$ this would involve activation of the $G_q$ pathway and production of the second messenger $IP_3$. Through the use of similar strategies and tools, it is possible to bias receptor signaling through pathways producing other second messengers such as $Ca^{++}$, cAMP, and $K^+$ currents, for example (Milligan, 1999).

It follows that the promiscuous interaction of the exogenously supplied $G_\alpha$ subunit with the receptor alleviates the need to carry out a different assay for each possible signaling pathway and increases the chances of detecting a functional signal upon receptor activation.

Methods for Recording Currents in *Xenopus* Oocytes

Oocytes are harvested from *Xenopus laevis* and injected with mRNA transcripts as previously described (Quick and Lester, 1994; Smith et al., 1997). The test receptor of this invention and Gα subunit RNA transcripts are synthesized using the T7 polymerase ("Message Machine," Ambion) from linearized plasmids or PCR products containing the complete coding region of the genes. Oocytes are injected with 10 ng synthetic receptor RNA and incubated for 3–8 days at 17 degrees. Three to eight hours prior to recording, oocytes are injected with 500 pg promiscuous Gα subunits mRNA in order to observe coupling to $Ca^{++}$ activated $Cl^-$ currents. Dual electrode voltage clamp (Axon Instruments Inc.) is performed using 3 M KCl-filled glass microelectrodes having resistances of 1–2 MOhm. Unless otherwise specified, oocytes are voltage clamped at a holding potential of –80 mV. During recordings, oocytes are bathed in continuously flowing (1–3 ml/min) medium containing 96 mM NaCl, 2 mM KCl, 1.8 mM $CaCl_2$, 1 mM $MgCl_2$, and 5 mM HEPES, pH 7.5 (ND96). Drugs are applied either by local perfusion from a 10 μl glass capillary tube fixed at a distance of 0.5 mm from the oocyte, or by switching from a series of gravity fed perfusion lines.

Other oocytes may be injected with a mixture of receptor mRNAs and synthetic mRNA encoding the genes for G-protein-activated inward rectifier channels (GIRK1 and GIRK4, U.S. Pat. Nos. 5,734,021 and 5,728,535 or GIRK1 and GIRK2) or any other appropriate combinations (see, e.g., Inanobe et al., 1999). Genes encoding G-protein inwardly rectifying $K^+$ (GIRK) channels 1, 2 and 4 (GIRK1, GIRK2, and GIRK4) may be obtained by PCR using the published sequences (Kubo et al., 1993; Dascal et al., 1993; Krapivinsky et al., 1995 and 1995b) to derive appropriate 5' and 3' primers. Human heart or brain cDNA may be used as template together with appropriate primers.

Heterologous expression of GPCRs in *Xenopus* oocytes has been widely used to determine the identity of signaling pathways activated by agonist stimulation (Gundersen et al., 1983; Takahashi et al., 1987). Activation of the phospholipase C (PLC) pathway is assayed by applying a test compound in ND96 solution to oocytes previously injected with mRNA for the SNORF25 receptor and observing inward currents at a holding potential of approximately –80 mV. The appearance of currents that reverse at –25 mV and display other properties of the $Ca^{++}$-activated $Cl^-$ channel is indicative of receptor-activation of PLC and release of $IP_3$ and intracellular $Ca^{++}$. Such activity is exhibited by GPCRs that couple to $G_q$ or $G_{11}$.

Involvement of the $G_{1/o}$ class of G-proteins in GPCR-stimulated $Ca^{++}$-activated $Cl^-$ currents is evaluated using PTX, a toxin which inactivates $G_{1/o}$ G-proteins. Oocytes are injected with 25 ng PTX/oocyte and modulation of $Ca^{++}$-activated $Cl^-$ currents by SNORF25 receptor is evaluated 2–5 h subsequently.

Elevation of intracellular cAMP can be monitored in oocytes by expression of the cystic fibrosis transmembrane conductance regulator (CFTR) whose $Cl^-$-selective pore opens in response to phosphorylation by protein kinase A (Riordan, 1993). In order to prepare RNA transcripts for expression in oocytes, a template was created by PCR using 5' and 3' primers derived from the published sequence of the CFTR gene (Riordan, 1993). The 5' primer included the sequence coding for T7 polymerase so that transcripts could be generated directly from the PCR products without cloning. Oocytes were injected with 10 ng of CFTR mRNA in addition to 10–15 ng mRNA for SNORF25. Electrophysiological recordings were made in ND96 solution after a 2–3 day incubation at 18° C. Currents are recorded under dual electrode voltage clamp (Axon Instruments Inc.) with 3 M KCl-filled glass microelectrodes having resistances of 1–2 Mohm. Unless otherwise specified, oocytes are voltage clamped at a holding potential of –80 mV. During recordings, oocytes are bathed in continuously flowing (1–3 ml/min) medium containing 96 mM NaCl, 2 mM KCl, 1.8 mM $CaCl_2$, 1 mM $MgCl_2$, and 5 mM HEPES, pH 7.5 (ND96). Drugs are applied either by local perfusion from a 10 μl glass capillary tube fixed at a distance of 0.5 mm from the oocyte, or by switching from a series of gravity fed perfusion lines.

Activation of G-protein $G_i$ and $G_o$ can be monitored by measuring the activity of inwardly rectifying $K^+$ (potassium) channels (GIRKs). Activity may be monitored in oocytes that have been co-injected with mRNAs encoding the mammalian receptor plus GIRK subunits. GIRK gene products co-assemble to form a G-protein activated potassium channel known to be activated (i.e., stimulated) by a number of GPCRs that couple to $G_i$ or $G_o$ (Kubo et al., 1993; Dascal et al., 1993). Oocytes expressing the mammalian receptor plus the GIRK subunits are tested for test compound responsivity by measuring $K^+$ currents in elevated $K^+$ solution containing 49 mM $K^+$.

Localization of mRNA Coding for Human and Rat SNORF25.

Methods: Quantitative RT-PCR Using a Fluorogenic Probe with Real Time Detection.

Quantitative RT-PCR using fluorogenic probes and a panel of mRNA extracted from human and rat tissue was used to characterize the localization of SNORF25 rat and human RNA.

This assay utilizes two oligonucleotides for conventional PCR amplification and a third specific oligonucleotide probe that is labeled with a reporter at the 5' end and a quencher at the 3' end of the oligonucleotide. In the instant invention, FAM (6-carboxyfluorescein) and JOE (6 carboxy-4,5-dichloro-2,7-dimethoxyfluorescein) were the two reporters that were utilized and TAMRA (6-carboxy-4,7,2,7'-tetramethylrhodamine) was the quencher. As amplification progresses, the labeled oligonucleotide probe hybridizes to the gene sequence between the two oligonucleotides used for amplification. The nuclease activity of Taq, or rTth thermostable DNA polymerases is utilized to cleave the labeled probe. This separates the quencher from the reporter and generates a fluorescent signal that is directly proportional to the amount of amplicon generated. This labeled probe confers a high degree of specificity. Non-specific amplification is not detected as the labeled probe does not hybridize. All experiments were conducted in a PE7700 Sequence Detection System (Perkin Elmer, Foster City, Calif.).

Quantitative RT-PCR

For the detection of RNA encoding SNORF25, quantitative RT-PCR was performed on mRNA extracted from tissue. Reverse transcription and PCR reactions were carried out in 50 µl volumes using rTth thermostable DNA polymerase (Perkin Elmer). Primers with the following sequences were used:

SNORF25 Human:

Forward Primer:
SNORF25H-765F
5'-CCTCTACCTAGTGCTGGAACGG-3' (SEQ ID NO: 18)

Reverse Primer
SNORF25H-868R
5'-GCTGCAGTCGCACCTCCT-3' (SEQ ID NO: 19)

Fluorogenic Oligonucleotide Probe:
SNORF25H-814T

```
                                            (SEQ ID NO: 20)
5' (6-FAM)-
   TCCCTGCTCAACCCACTCATCTATGCCTATT-(TAMRA) 3'
```

SNORF25 Rat

Forward Primer
SNORF25R-231F
5'-GTGTAGCCTTCGGATGGCA-3' (SEQ ID NO: 21)

Reverse Primer
SNORF25R-329R
5'-GGCTGCTTAATGGCCAGGTAC-3' (SEQ ID NO: 22)

Fluorogenic Oligonucleotide Probe:
SNORF25R-278T

```
                                            (SEQ ID NO:23)
5' (6-FAM)-TCCTCACGGTCATGCTGATTGCCTTT-(TAMRA) 3'
```

SNORF25 Mouse

Forward Primer:
snorf25M-307F
5'-CCTCACCGTCATGCTGATTG-3' (SEQ ID NO: 29)

Reverse Primer
snorf25M-407R
5'-CAATGCATGCTCCAGCCAC-3' (SEQ ID NO: 30)

Fluorogenic Oligonucleotide Probe
snorf25M-342T

```
                                            (SEQ ID NO:31)
5' (6-FAM)-TTGCCATTAAGCAGCCCCTCCGTTA-(TAMRA) 3'
```

Using these primer pairs, amplicon length is 104 bp for human SNORF25, 99 bp for rat and 100 bp for mouse SNORF25. Each RT-PCR reaction contained 50–100 ng mRNA. Oligonucleotide concentrations were: 500 nM of forward and reverse primers, and 200 nM of fluorogenic probe. Concentrations of reagents in each reaction were: 300 µM each of dGTP; dATP; dCTP; 600 µM UTP; 3.0 mM $Mn(OAc)_2$; 50 mM Bicine; 115 mM potassium acetate, 8% glycerol, 5 units rtth thermostable DNA polymerase, and 0.5 units of uracil N-glycosylase. Buffer for RT-PCR reactions also contained a fluor used as a passive reference (ROX: Perkin Elmer proprietary passive reference I). All reagents for RT-PCR (except mRNA and oligonucleotide primers) were obtained from Perkin Elmer (Foster City, Calif.). Reactions were carried using the following thermal cycler profile: 50° C. 2 min., 60° C. 30 min., 95° C. 5 min., followed by 40 cycles of: 94° C., 20 sec., 62° C. 1 min.

Positive controls for PCR reactions consisted of amplification of the target sequence from a plasmid construct. Standard curves for quantitation were constructed using the human SNORF25 gene in a plasmid vector or RNA extracted from pancreas as a template for amplification. Negative controls consisted of mRNA blanks, as well as primer and mRNA blanks. To confirm that the mRNA was not contaminated with genomic DNA, PCR reactions were carried out without reverse transcription using Taq DNA polymerase. Integrity of RNA was assessed by amplification of mRNA coding for cyclophilin or glyceraldehyde 3-phosphate dehydrogenase (GAPDH). Following reverse transcription and PCR amplification, data was analyzed using Perkin Elmer sequence detection software. The fluorescent signal from each well was normalized using an internal passive reference, and data was fitted to a standard curve to obtain relative quantities of SNORF25 mRNA expression.

Generation of mSNORF25 Riboprobes cDNA encoding mSNORF25 was obtained by PCR from mouse genomic DNA (Clonetech, Palo Alto, Calif.). The first primer pair was directed to the 5' untranslated region approximately 30 base pairs (bp) upstream from the initiating methionine (forward primer) to the third transmembrane domain (reverse primer). The second primer pair was directed towards the carboxy terminus (forward primer) and to the 3' untranslated region approximately 300 bp downstream from the stop codon (reverse primer). The PCR primers synthesized have the following sequences:

mSNORF25 Amino Terminus Region

Forward Primer:
5'-CATCCAGCATGCCTTTGTAAGTGGA-3' (SEQ ID NO: 32)

Reverse Primer:
5'-AATCAGCATGACGGTGAGGACAGAG-3' (SEQ ID NO: 33)

mSNORF25 Carboxy Terminus Region

Forward Primer:
5'-CGGCAGCAGCTCTACCACATGGC-3' (SEQ ID NO: 34)

Reverse Primer:
5'-CAAACACCCTTTCAGCAGTATACTCC-3' (SEQ ID NO: 35)

A PCR program was designed with initial melting set at 94° C. followed by 40 alternating cycles of 94° C. for 30 seconds and 62° C. for 1 minute, and a final extension at 62° C. for 4 minutes. PCR reactions were carried out in 50 µl microamp tubes using Expand Long Template System (Roche Molecular Biochemicals, Indianapolis, Ind.). The PCR reaction contained 10 µM of both forward and reverse primers, 2.5 mM each of CTP, ATP, GTP, and TTP (Roche Molecular Biochemicals, Indianapolis, Ind.), 100 ng mouse genomic DNA (Clonetech, Palo Alto, Calif.), 10×Buffer #3 (22.5 mM $MgCl_2$) (Roche Molecular Biochemicals, Indianapolis, Ind.), Expand Long Enzyme (Roche Molecular Biochemicals, Indianapolis, Ind.) and molecular grade water (Research Products International Corp., Mt. Prospect, Ill.). PCR products were ethanol precipitated, lyophilized, reconstituted in molecular grade water, and aliquots were run on a 1.5% agarose/TBE gel (GibcoBRL/Life Technologies, Grand Island, N.Y.). A single band was detected at the expected size of 340 bp and 438 bp for N- and C-terminus products, respectively. Each band was excised from the gel, purified with QIAquick gel extraction kit (Qiagen, Valencia, Calif.), ethanol precipitated.

Transcription and Digoxigenin Labeling of Antisense and Sense Riboprobes

Transcription reactions were performed using the DIG RNA Labeling Kit (Roche Molecular Biochemicals, Indianapolis, Ind.). Transcription reactions consisted of 300 ng of purified PCR product, 10×Transcription Buffer (400 mM Tris-HCl pH 8.0; 60 mM $MgCl_2$, 100 mM dithioerythritol, 20 mM spermidine, 100 mM NaCl, 1 unit/ml RNase inhibitor), DIG Labeling mix (10 mM each of ATP, CTP, GTP, and 6.5 mM UTP, 3.5 mM UTP-DIG; in Tris-HCl pH 7.5), T7 or T3 polymerase (20 units/µl) (Promega, Madison, Wis.), and molecular grade water. Reactions were carried out at 37° C. for 2 hours, stopped with 0.2 M EDTA, pH 8.0, ethanol precipitated, and resuspended in molecular grade water to a final concentration of approximately 1 µg/µl and stored at −20° C. until use.

To verify probe labeling, the riboprobes were serially diluted, spotted on a positively charged nylon membrane (Roche Molecular Biochemicals, Indianapolis, Ind.), and crosslinked with a UV Stratalinker (Stratagene, La Jolla, Calif.). The membrane was washed briefly in Washing Buffer (100 mM Tris-HCl, pH 7.5, 150 mM NaCl, 0.3% Tween 20), incubated for 30 min in Blocking Buffer (100 mM Maleic acid, 100 mM Tris-HCl, pH 7.5, 150 mM NaCl, 0.1% Triton X-100 and 2% normal sheep serum), and incubated in sheep anti-DIG-alkaline phosphatase (Fab Fragments) (1:5000) for 30 min. The membrane was washed twice for 5 min in Washing Buffer, 2 min in Detection Buffer (100 mM Tris-HCl, pH 9.5, 100 mM NaCl, 50 mM $MgCl_2$) then incubated in the dark for 1 hour in Detection Buffer containing BCIP/NBT substrate (9.4 mg/ml 5-bromo-4-chloro-3-indolyl-phosphate and 18.75 mg/ml nitroblue tetrazolium chloride in 67% dimethyl formamide). The reaction was stopped with molecular grade water. The labeling efficiency and concentrations of the riboprobes were determined by comparing the color intensity of a control labeled riboprobe (known concentration) and experimental spots. Roche Molecular Biochemicals, Indianapolis, Ind., supplied all reagents.

Controls

To determine the specificity of hybridization of the DIG-labeled riboprobes to mSNORF25 mRNA, in situ hybridization was performed on COS-7 cells transiently transfected with the mSNORF25 gene or mock-transfected (vector only). COS-7 cells were, grown on poly-L-lysine-coated plastic chamber slides (Nalge Nunc International, Naperville, Ill.) and transiently transfected as previously described (Borowsky et al., 1999). The cells were washed with phosphate buffered saline (PBS) (Sigma, St. Louis, Mo.) to remove the medium, fixed for 5 min in 4% paraformaldehyde (PFA), permeabilized 0.3% Triton X-100, washed with PBS and incubated in hybridization buffer containing the DIG-labeled mSNORF25 riboprobes (7 ng/30 ul) overnight at 45° C. Post hybridization washes and immunological detection were carried out as described above for the tissues.

Controls used to verify the specificity of hybridization signals in tissue sections included (1) the use of multiple probes made to disparate regions of the mSNORF25 gene, (2) the use of heterologous probes, and (3) hybridization using sense riboprobes.

Nonradioactive in situ Hybridization Histochemistry

A total of five male 129S6/SVEV mice, (25 g) (Taconic Farms, Germantown, N.Y.) were deeply anesthetized by intraperitoneal injection of ketamine (10 mg/kg) (RBI, Natick, Mass.) and xylazine (0.1 mg/kg) (Bayer, Shawnee Mission, Kans.). The mice were transcardially perfused with approximately 75 ml of diethyl pyrocarbonate (DEPC) (Sigma, St. Louis, Mo.) treated PBS, pH 7.4, followed by approximately 75 ml 4% PFA (Sigma, St. Louis, Mo.) in DEPC-treated PBS. Tissue were removed and postfixed for 2 hours in 4% PFA at 4° C. and cryoprotected in 30% sucrose at 4° C. for 48 hours before freezing on dry ice. Tissues were cut at 30 µm using a freezing microtome, immediately submerged in DEPC-treated PBS and stored at 4° C. until use.

In situ hybridization experiments were performed on free floating tissue sections and processed according to the protocol outlined in Roche Molecular Biochemicals *Nonradioactive In situ hybridization Application Manual*. Briefly, tissue sections were washed twice for 5 min each in DEPC-treated PBS, two times 5 min each in 100 mM glycine (Sigma, St. Louis, Mo.)/DEPC-treated PBS, permeabilized for 15 min in 0.3% Triton X-100 (Sigma, St. Louis, Mo.)/DEPC treated-PBS, washed twice for 5 min in DEPC-treated PBS, then incubated overnight at 45° C. in hybridization buffer containing 40% formamide (GibcoBRL/Life Technologies, Grand Island, N.Y.), 10% dextran sulfate (Sigma, St. Louis, Mo.), 4×SSC (GibcoBRL/Life Technologies, Grand Island, N.Y.), 10 mM DTT (Sigma, St. Louis, Mo.), 1 mg/ml yeast tRNA (GibcoBRL/Life Technologies, Grand Island, N.Y.), 1 mg/ml salmon sperm DNA (Sigma, St. Louis, Mo.) and molecular grade water containing 7 ng/30 µl probe.

The following day post hybridization washes were performed at 37° C. Tissue sections were washed twice for 15 min each in 2×SSC and 1×SSC, 30 min in NTE (500 mM NaCl, 10 mM Tris-HCl, pH 8.0, 1 mM EDTA) containing 20 µg/µl RNase A (Sigma, St. Louis, Mo.) followed by two 15 min washes in 0.1×SSC.

Immunological detection of the mouse SNORF25 hybridization signal in the tissues was performed as outlined in the Roche Molecular Biochemicals *Nonradioactive In situ*

Hybridization Application Manual. All solutions were made with reagents from Roche Molecular Biochemicals Indianapolis, Ind. Sections were processed in the following manner: two 10 min washes in Washing Buffer, a 30 min incubation in Blocking Buffer, a 2 hour incubation in sheep anti-DIG-alkaline phosphatase (Fab fragments) (1:500) in Blocking Buffer, two 10 min washes in Washing Buffer, and a 10 min incubation in Detection Buffer. The tissues were incubated overnight and protected from light in a color solution containing NBT/BCIP and 2.4 mg/10 ml levamisole. The reaction was stopped after 17 hours in TE (10 mM Tris-HCl, pH 8.1, 1 mM EDTA) and washed three times in molecular grade water. Sections were mounted onto slides using mounting media (40% ethanol: 0.01% gelatin), allowed to air dry for 1 hour, counterstained in 0.02% Fast Green FCF (Sigma, St. Louis, Mo.), rinsed three times in molecular grade water, then coverslipped using Aquamount (Lerner Laboratories, Pittsburgh, Pa.).

Quantification

The strength of the hybridization signal obtained in various region of the mouse brain was graded as weak (+), moderate (++), heavy (+++) or intense (++++). These were qualitative evaluations of two independent observers for the distribution of SNORF25 mRNA based on the relative intensity of the chromogen (NBT/BCIP) staining (blue color) A total of 5 mouse brains were analyzed.

RESULTS AND DISCUSSION

Cloning of the Full-length Sequence of SNORF25

Genomic DNA and cDNA prepared from several tissues (including GH1 cells and Rin14b cells) was subjected to MOPAC PCR with two degenerate primers designed based on the third transmembrane domain of the members of the galanin, somatostatin, and opioid receptor families and the seventh transmembrane domain of members of the galanin receptor family. Three products from this reaction were found to be the same clone in either orientation (forward or reverse), which was a novel sequence not found in the Genbank, SwissProtPlus, GSS, EST, or STS databases. It contained significant homology to other known G protein-coupled receptors (~29% identity to the known receptors dopamine D1, beta-adrenergic 2b and 5-$HT_{1F}$; 34% identity to 5-$HT_{4L}$ receptor). This receptor sequence was later named SNORF25, and was used to design primers for 5' and 3' Rapid Amplification of cDNA Ends (RACE), as described in the Methods section above. The 5' RACE reaction yielded sequence information through the first transmembrane domain and a putative in-frame initiating methionine-coding sequence surrounded by a kozak consensus sequence (ACCATGG).

The 3' RACE reaction yielded a 600 bp band by agarose gel electrophoresis. This band was subcloned into the TA cloning kit, and isolated colonies were sequenced. The sequence of these products revealed the presence of an in-frame stop codon downstream from the region coding for the seventh transmembrane domain. The entire size of the coding sequence of SNORF25 was determined to be 1005 bp, coding for a protein of 335 amino acids. Two primers, JAB86 and JAB84, were used to amplify the entire coding sequence from Rin14b cell line cDNA and rat genomic DNA using the Expand Long PCR system. The primers for this reaction were specific to the 5' and 3' untranslated regions of SNORF25 with BamHI and HindIII restriction sites incorporated into the 5' ends of the 5' and 3' primers, respectively. When the products of these reactions were subcloned into pcDNA3.1 (−) and sequenced, the sequence of the Rin14b clone and the genomic clone were found to be identical, and the vector construct containing rat SNORF25 was named pcDNA3.1-rSNORF25.

Hydrophobicity (Kyte-Doolittle) analysis of the amino acid sequence of the full-length clone indicates the presence of seven hydrophobic regions, which is consistent with the seven transmembrane domains of a G protein-coupled receptor. The seven expected transmembrane domains are indicated in FIG. 4. A comparison of nucleotide and peptide sequences of rat SNORF25 with sequences contained in the Genbank, EMBL, and SwissProtPlus databases reveals that the amino acid sequence of this receptor is most related to histamine, adenosine, serotonin, beta adrenergic, and dopamine receptor families, displaying between 25–30% overall amino acid identity with these receptors. The N- and C-termini are relatively short, much like the adenosine receptor family. However, transmembrane domain analysis indicates that this receptor shares a significant degree of identity to other GPCRs in its transmembrane domains. A comparison of all of the transmembrane domains of SNORF25 simultaneously with a comprehensive list of GPCR transmembrane domains would suggest that the transmembrane domains of SNORF25 have the highest degree of identity with the beta adrenergic receptors 1 and 2 of 31% and 32%, respectively, as well as 5-$HT_7$ and 5-$hT_{5B}$ receptors of 32% and 36.6%, respectively. When transmembrane domains are analyzed individually by a FASTA search, SNORF25 exhibits considerable similarity to the transmembrane domains of a variety of known G protein-coupled receptors.

Figure 2B:
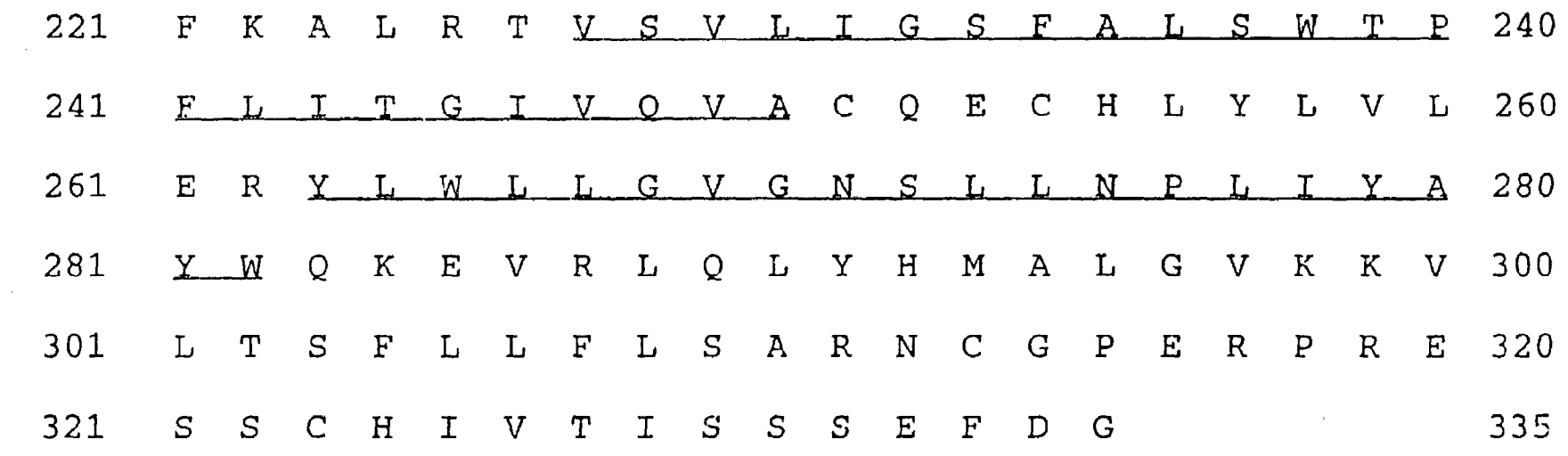

In order to clone the human homolog of SNORF25, a human genomic cosmid library was screened at medium stringency with labeled oligonucleotide probes designed based on the second and fifth transmembrane domains of rat SNORF25. Out of roughly 225,000 colonies screened, two colonies hybridized to the probes. After isolation and analysis of each colony, these two clones were determined to be identical cosmid clones containing the human homolog of SNORF25. Southern blot analysis of several restriction digests of this cosmid and subsequent sequencing of positive bands indicated that a BamHI/HindIII digest of this cosmid yielded a 1.9 kb fragment containing the full-length coding sequence of this human clone. The construct of the human receptor subcloned into the BamHI/HindIII site of the pEXJT3T7 vector is named pEXJT3T7-hSNORF25. Human SNORF25 exhibits an 80% DNA identity and 83% amino acid identity to rat SNORF25. Like the rat receptor, the protein-coding region of human SNORF25 is 1005 nucleotides (FIGS. 1A–1B), coding for a protein of 335 amino acids (FIGS. 2A–2B). The DNA and amino acid sequences of rat SNORF25 are shown in FIGS. 3A–3B and 4A–4B, respectively.

A search of the GenEMBL, SwissProtplus, EST, STS and GSS databases confirmed that human SNORF25 is also a unique novel sequence. Other than its identity with rat SNORF25, it shares 28–30% overall identity with adenosine 2a, 5-$HT_{4L}$, 5-$HT_{4S}$, 5-$H_{T6}$, and 5-$HT_7$, dopamine $D_1$ and $D_5$, and somatostatin 5 receptors. It also shares 25–26% identity with adenosine A1, histamine H1 and 2, beta adrenergic 1, and somatostatin 2 and 3 receptors. A comparison of all of the transmembrane domains of human SNORF25 simultaneously with a comprehensive list of GPCR transmembrane domains would suggest that the transmembrane domains of human SNORF25 have the highest degree of identity with the beta 1 and 2 adrenergic receptors (29% and 32%, respectively) and 5-$HT_4$. Individual transmembrane domains of human SNORF25 share significant identity with transmembrane domains from several other G protein-coupled receptors.

Both rat and human SNORF25 have several potential protein kinase C (PKC) phosphorylation motifs throughout their amino acid sequences. For both receptors, threonine 73, serine 79, and serine 309 are potential PKC phosphorylation sites. The human receptor has an additional putative PKC phosphorylation site at serine 214, which is a proline in rat SNORF25. Both receptors share a potential casein kinase II (CKII) phosphorylation site at serine 329. The human SNORF25 also contains two more potential CKII phosphorylation sites, threonine 217 and serine 331, that are not present in the rat receptor. Conversely, rat SNORF25 contains a potential tyrosine phosphorylation site at tyrosine 323, which is not present in the human receptor.

Isolation of a Fragment of the Mouse SNORF25

PCR primers designed against the first and seventh transmembrane domains of the rat and human SNORF25 were used to amplify a fragment from mouse genomic DNA. Sequencing of this band revealed a 820 base pair product with high homology to the rat and human SNORF25.

Isolation of the Full-length Mouse SNORF25

To obtain a full-length mouse SNORF25, a mouse genomic library was screened under high stringency conditions using a $^{32}$P-labeled oligonucleotide probe designed based on the mouse fragment described above. A positive signal was isolated and a hybridyzing fragment subcloned in the pEXJ vector. This construct, B0148, was renamed pEXJ-mS-NORF25-f. The largest open reading frame in mouse SNORF25 is 1005 nucleotides, predicting a protein of 335 amino acids. The nucleotide and amino acid sequences of mouse SNORF25 are shown in FIGS. 13A–13B and 14A–14B, respectively. Mouse SNORF25 shares 95% nucleotide and 96% amino acid identities with rat SNORF25. Mouse SNORF25 shares 85% nucleotide and 82% amino acid identities with human SNORF25. No sequences identical to mouse SNORF25 were found in the Genembl databases.

cAMP Response of SNORF25-Transfected Cells

The expression vector (pcDNA) containing the SNORF25 cDNA was transfected by electroporation method into CHO cells. After plating, the transfectants were challenged with a ligand library that included, among other things, several of the traditional neurotransmitters such as histamine, adenosine, serotonin, norepinephrine, and dopamine, based on homology of SNORF25 to the receptors of these ligands (see above), and tested for their ability to stimulate cAMP or IP release above mock-transfected cells. Interestingly, the basal cAMP levels of SNORF25-transfected cells were significantly higher (>10-fold) than mock-transfected cells (FIG. 5). This observation suggested that SNORF25 receptor may functionally be coupled to a cAMP stimulatory pathway. Among the ligands tested, only all-trans retinoic acid (ATRA) produced a significant increase in cAMP but not IP release in SNORF25-transfected cells, without affecting these parameters in mock-transfected CHO cells. The response produced at 10 μM concentration of ATRA (2- to 5-fold above basal) was comparable to that produced by forskolin, a potent direct stimulator of adenylyl cyclase (FIG. 6) (n=3).

Figure 6:
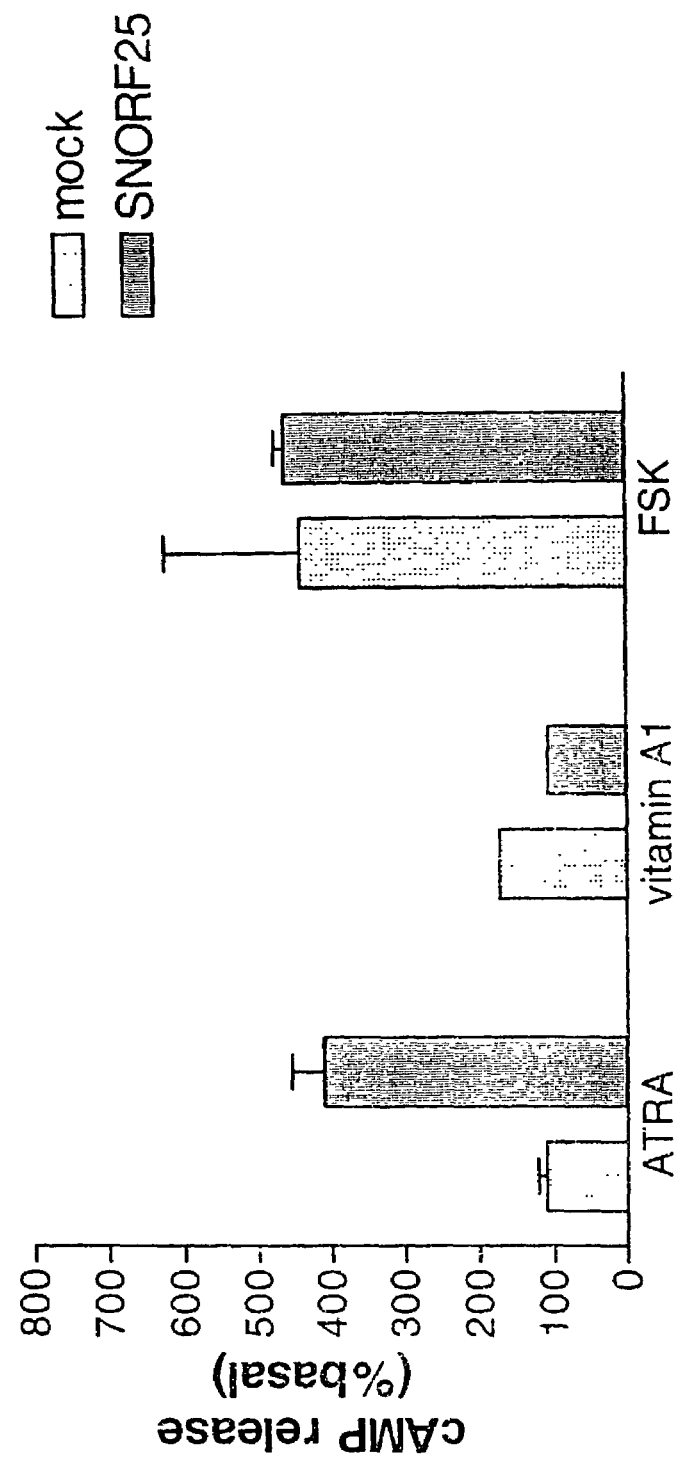
FIG. 6 Modulation of cAMP release by ATRA, vitamin $A_1$ and forskolin in SNORF25-expressing mock-transfected CHO cells. The transfectants were plated into 96-well plates, challenged with 10 μM concentrations of drugs and assayed for cAMP release as described. The results of a representative experiment involving known cyclase stimulatory receptors are shown. Results are means±S.E.M of triplicate determinations with the exception of vitamin $A_1$ which is a single point. Results are normalized to % basal cAMP release.

Responses to forskolin in both mock- and SNORF25-transfected Cos-7 cells were almost identical (FIG. 6), suggesting that the enhanced maximal response to ATRA observed in SNORF25-expressing cells, as compared to mock DNA-transfected cells, was not due to a change in cell density or in the intrinsic properties of the cells. All-trans retinol (vitamin $A_1$), a close analogue of ATRA failed to produce an increase in cAMP at 10 μM (FIG. 6).

Figure 7:
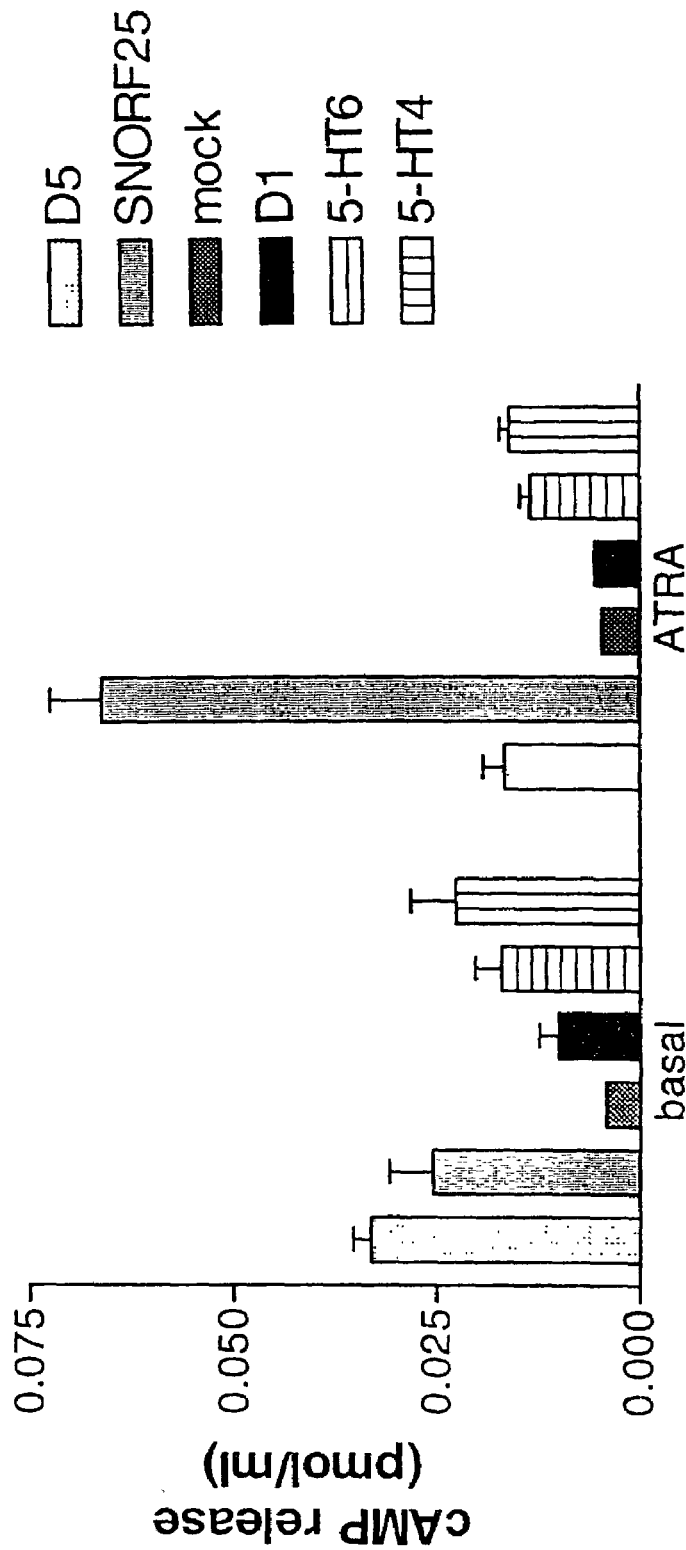
FIG. 7 Specificity of ATRA cAMP response in Cos-7 cells. The transfectants were plated into 96-well plates, challenged with 10 μM concentrations of ATRA and assayed for cAMP release as described. The results of a representative experiment are shown. Results are means±S.E.M of triplicate determinations.

Subsequent experiments demonstrated that the ATRA-induced increase in cAMP formation was independent of host cell as it was observed also in Cos-7 cells (n=3) (FIG. 7). All-trans-retinoic acid produced no response in Cos-7 cells transfected with other known cyclase-stimulatory receptors including dopamine D1, D5, serotonin 5-HT4 and 5-HT6 receptors, indicating that the response observed to ATRA is specific to SNORF25-transfected cells (FIG. 7).

Figure 8:
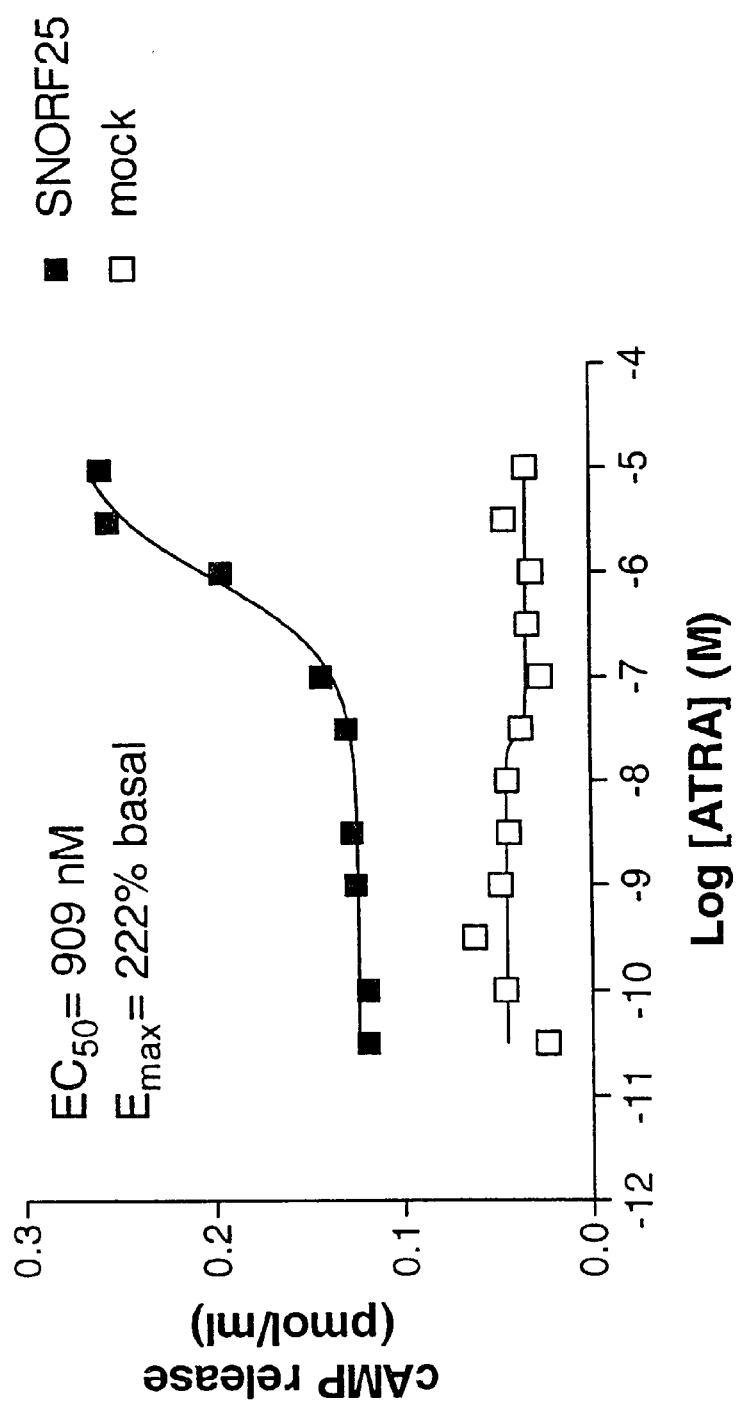
FIG. 8 ATRA Dose-response curve in transiently-transfected Cos-7 cells. A representative example of dose-response effect of ATRA to increase cAMP release in SNORF25-(■) and mock-(□) transfected cells.

The cAMP response to ATRA in Cos-7 cells was concentration-dependent with $EC_{50}$ values ranging from approximately 0.2 to 1 μM and $E_{max}$ of approximately 200–300% (FIG. 8).

cAMP Response of SNORF25-Stable Transfected CHO Cells

Figure 11A:
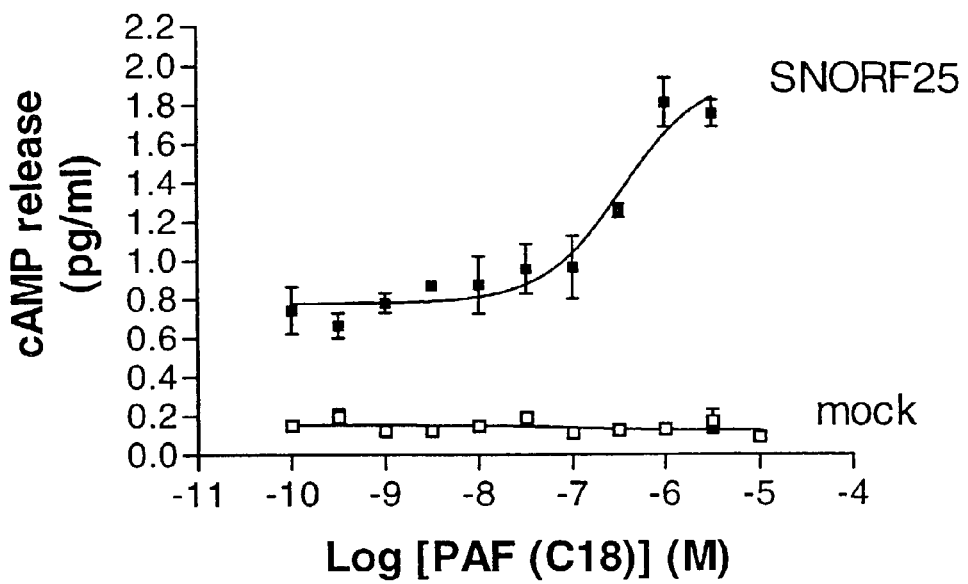
FIGS. 11A–11B PAF and ATRA dose-response curve in stably transfected and native untransfected CHO cells. A representative example of dose-response effect of PAF (C18) (FIG. 11A) and ATRA (FIG. 11B) to increase cAMP release in SNORF25-(■) and native untransfected (□) CHO cells. Results are means±S.D.M. of duplicate determinations from one experiment, typical of at least 3 experiments.
Figure 11B:
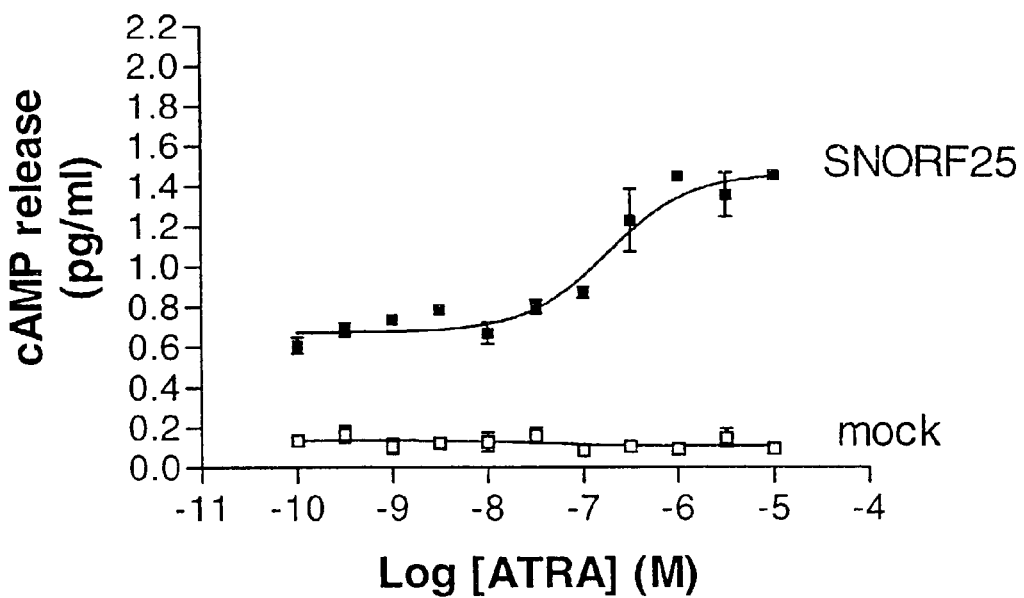

Preliminary results in Cos-7 cells transiently transfected with SNORF25 indicated that PAF could stimulate cAMP levels by 4–5-fold in SNORF25 but not mock-transfected cells (data not shown). This data indicated that PAF in addition to ATRA could be a ligand for this receptor. This possibility was further explored in CHO cells stably transfected with SNORF25 and compared to native untransfected mock CHO cells. Interestingly, the basal cAMP levels of SNORF25-transfected cells were significantly higher (2–4-fold) than mock-native CHO cells as previously observed in Cos-7 cells (FIGS. 11A–11B).

The cAMP response to PAF in CHO cells expressing SNORF25 was concentration-dependent with $EC_{50}$ values ranging from approximately 0.3 to 1:M and $E_{max}$ of approximately 200–400% basal. No response was observed to PAF in untransfected CHO cells (FIG. 11A). Several other closely related analogues of PAF namely Lyso-PAF with different carbon chains also stimulated cAMP. As shown in FIG. 11B, ATRA stimulated cAMP release in SNORF25 stable CHO cells with about a 3-fold lower potency than PAF(C18). The rank order of potency of the compounds stimulating SNORF25 was as follows: PAF(C18)>PAF(C16)>ATRA>Lyso-PAF(C16)>Lyso-PAF(C18) (See Table 4). Several other lipid like compounds were also evaluated but showed no stimulation of cAMP at 10 μM, including LPA, AA, vitamin D3, vitamin E, licopene and Atb carotene (data not shown).

Figure 12A:
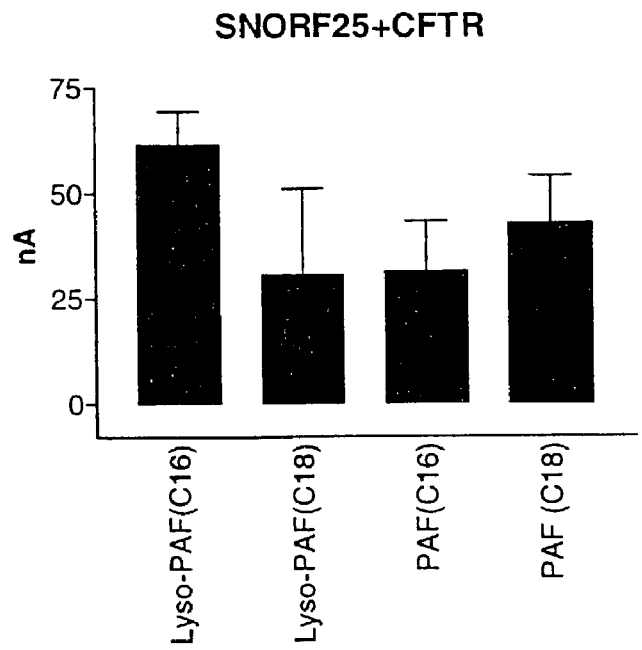
FIGS. 12A–12B Mean maximal current amplitudes stimulated by PAF(C16), PAF(C18), lyso-PAF(C16), and lyso-PAF (C18) (10 µM each) in oocytes injected with SNORF25 and CFTR mRNAs (n=7–13 oocytes) (FIG. 12A), and in oocytes injected with only CFTR mRNA (n=8–10 oocytes) (FIG. 12B).
Figure 12B:
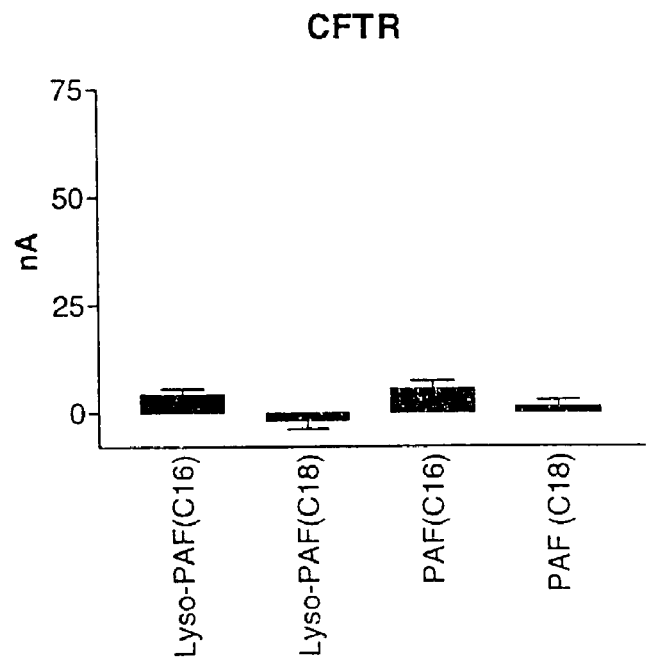

The sensitivity of SNORF25 to PAF compounds and analogues was also assessed in oocytes co-injected with mRNA encoding SNORF25 and mRNA encoding CFTR. Each of the compounds was tested at 10 μM. Oocytes expressing SNORF25 generated inward Cl⁻ currents, consistent with CFTR activation, in response to all four of the ligands. In agreement with the cAMP data above, robust responses were elicited by PAF(C18 and C16) and lysoPAF(C16 and C18) (e.g. LysoPAF (C16) 61.7±7.8 nA; n=13 oocytes; FIG. 12A). Control oocytes, injected with only CFTR did not respond to any of the PAF compounds (FIG. 12B).

The pharmacological profile of SNORF25 and the localization of its mRNA in the pancreas suggests that this receptor could play a role in insulin secretion. Interestingly, in isolated rat pancreatic islets, lyso-PAF has been shown to initiate insulin release at both basal (1.7 mM) and stimulatory (16.7 mM) glucose concentrations in a dose-dependent manner. The potency of this response is low (EC50~100 μM). Furthermore, PAF is nearly equipotent to lyso-PAF (Metz, 1986) in inducing insulin secretion. The pharmacological profile mediating insulin release by PAF and lyso-PAF is very different from that expected of typical cloned or native PAF receptors, which have nanomolar potencies for PAF and are not activated by lyso-PAF. Finally, the data shown here suggests that SNORF25 mediates the stimulatory effects of lyso-PAF and PAF on insulin release.

TABLE 4

Stimulation of cAMP release by CHO cells stably expressing hSNORF25 receptors.
Potencies are given as means of EC50 values ± S.E.M. obtained from at least 3 experiments. Maximum responses produced by compounds are expressed as the % maximum response produced by PAF(C18) (taken as 100%).

| Compound | EC50 (nM) | % of PAF(C18) Response |
|---|---|---|
| PAF(C18) | 537 ± 107 | 100 |
| PAF(C16) | 982 ± 233 | 110 |
| ATRA | 1445 ± 652 | 105 |
| Lyso-PAF(C16) | 3475 ± 1131 | 120 |
| Lyso-PAF(C18) | 5452 ± 2631 | 70 |

Activation of Calcium-activated Cl⁻ Currents in SNORF25 Expressing *Xenopus* Oocytes Elevation of intracellular cAMP can be monitored in oocytes by expression of the cystic fibrosis transmembrane conductance regulator (CFTR) whose Cl⁻-selective pore opens in response to phosphorylation by protein kinase A (Riordan, 1993). The activity of SNORF25 was therefore tested in oocytes co-injected with mRNA encoding SNORF25 and mRNA encoding CFTR. In 17 out of 39 of these oocytes an inward Cl⁻ current (105±20 nA) was measured in response to the application of 10 µM all-trans-retinoic acid (See FIGS. 9A–9C and 10).

This response was specific to the expression of SNORF25 since no such current was observed in other oocytes injected with only mRNA encoding the CFTR channel. Similar currents were observed in oocytes injected with the β2-adrenergic receptor (B2AR) (See FIG. 9C), although the currents generated by SNORF25-expressing oocytes were generally 2–3 fold slower and smaller. All-trans-retinoic acid did not stimulate Cl⁻ currents in oocytes lacking CFTR, indicating that the Gq-mediated phospholipase C pathway was not activated. Responses also were not evoked in oocytes expressing chimeric G-proteins which are able to couple Gi and Go coupled GPCRs to the phospholipase C pathway. Taken together, these observations support the hypothesis that SNORF25 encodes a GPCR which binds all-trans-retinoic acid and stimulates the production of cAMP, presumably via activation of Gs.

Figure 9A:
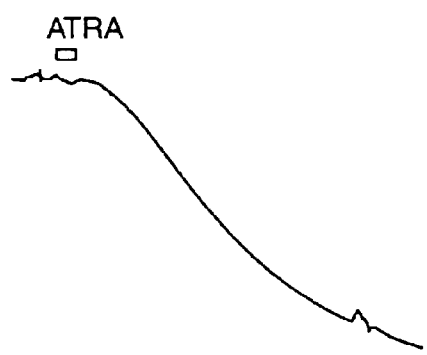
FIGS. 9A–9C Stimulation of CFTR by ATRA in ooctyes expressing SNORF25. Voltage clamp recording from oocyte previously injected with SNORF25 receptor mRNA and CFTR (FIG. 9A), and from control (CFTR alone) oocyte (FIG. 9B). Application of epinephrine (1 µM) evokes a similar current in other oocytes expressing the B2 adrenergic receptor (B2AR) and CFTR (FIG. 9C). Holding potential was −70 mV for all recordings.
Figure 9B:
Figure 9C:
Figure 10:
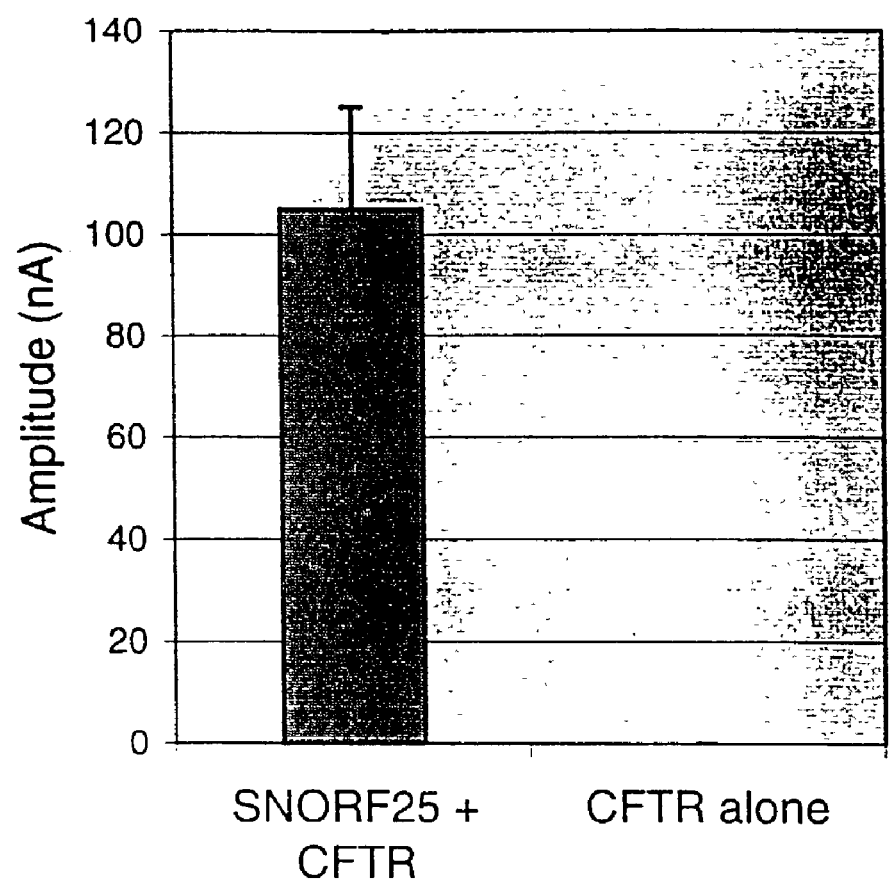
FIG. 10 Mean current amplitudes stimulated by ATRA (10 µM) in control (CFTR alone) ooctyes (n=16) and oocytes injected with mRNA encoding SNORF25 and CFTR (n=17).

In other systems, all-trans-retinoic acid stimulates one of several nuclear receptors (see background). This results in the enhancement of transcription of one or more genes. SNORF25 expression in oocytes could result in the expression of a nuclear receptor for all-trans-retinoic acid, not normally present in uninjected oocytes, that when stimulated produces an elevation of cAMP. If this were the case, then retinoic acid would not necessarily bind the SNORF25 receptor, but would act on a previously know or novel nuclear receptor for retinoic acid. This indirect mechanism of action of retinoic acid may explain why the ligand failed to elicit a CFTR response in 3 out of 6 batches of oocytes (17 of 39 oocytes), and why the kinetics of CFTR activation were 2–3 times slower than those observed under conditions where responses were evoked by activation of well-characterized GPCRs such as the B2 adrenergic receptor (FIG. 9C). Nevertheless, the delay for activation of CFTR by retinoic acid was on the order of 10 seconds, and the activation of nuclear receptors is typically in the range of several minutes to hours. Thus, while we cannot rule out an indirect mechanism of action of retinoic acid, the relatively rapid onset of the response in SNORF25-expressing oocytes suggests that such a mechanism is unlikely.

Detection of mRNA Coding for Human SNORF25 mRNA was isolated from multiple tissues (listed in Table 1) and assayed as described.

Quantitative RT-PCR using a fluorgenic probe demonstrated expression of mRNA encoding human SNORF25 in most tissues assayed (Table 1). Highest levels of human SNORF25 mRNA are found in the pancreas, stomach, small intestine and fetal liver, with lower levels detected elsewhere. Most nervous system structures showed little expression of SNORF25 mRNA as compared to peripheral organs.

The highest levels of SNORF25 expression are found in the pancreas. The pancreas secretes a variety of broadly active substances (including insulin), indicating that SNORF25 may play a role in regulating multiple metabolic functions, potentially via endocrine mechanisms. SNORF25 expression in the pancreas is not surprising as SNORF25 is also expressed in a rat insulinoma cell line. This finding as well as the detection of SNORF25 mRNA in liver indicate a possible role in the regulation of glucose levels and possibly diabetes.

Other organs with high levels of SNORF25 mRNA are stomach and small intestine. The distribution to these structures is consistent with functions relating to gastrointestinal motility or absorption. It is not known at this time if SNORF25 mRNA is localized to smooth muscle or to mucosal/submucosal layers.

Although detected in very low levels, the presence of SNORF25 mRNA in multiple regions of the CNS including the thalamus and hippocampal formation (where levels are highest in the CNS) and other functionally diverse areas, indicate a diffuse regulatory function or regional functionality for this receptor.

Human SNORF25 mRNA appears to be developmentally regulated. In fetal liver, levels of mRNA approach those measured in adult pancreas (83%). However in adult tissue, this drops to less than 1% of the amount found in the pancreas. The profound change of SNORF25 mRNA during development implies a role in the maturation of the liver, or a role in the regulation of glucose demands/levels during development. The time course of this increase has not been examined and would be important in understanding the function of this receptor.

In summary, the distribution of SNORF25 receptor mRNA implies broad regulatory functions that involves multiple organ systems, endocrine mechanisms, as well as the central nervous system.

Detection of mRNA Coding for Rat SNORF25

Unlike the restricted distribution of human SNORF25 mRNA, the distribution of SNORF25 mRNA in the rat is widespread. One striking difference in the distribution between rat and human is the high levels of SNORF25 mRNA detected in the rat central nervous system. In the human, the highest concentrations of SNORF25 mRNA are found in the pancreas, with very low levels found in CNS structures. In the rat the highest levels of SNORF25 mRNA are found in the hippocampal formation, closely followed by levels detected in the cerebral cortex, cerebellum, hypothalamus, choroid plexus and medulla. SNORF25 mRNA is also detected in both dorsal root and trigeminal ganglia. Although SNORF25 mRNA is detected in rat pancreas and other peripheral organs, it is present there in much lower levels than in the CNS.

Rat SNORF25 was detected in most tissues assayed. In addition to the pancreas it is expressed in appreciable amounts in lung, colon, duodenum, ovary, kidney and the adrenal glands. It was detected in other tissues in decreasing amounts as shown in Table 2.

In summary, the broad distribution of rat SNORF25 receptor mRNA implies broad regulatory functions that involve multiple organ systems, endocrine mechanisms as well as the central nervous system. The difference in the distribution pattern seen between human and rat suggests a broader, and potentially different role for this receptor in the rat as compared to human.

Detection of Mouse SNORF25 RNA

RNA was isolated from multiple tissues (listed in Table 3) and assayed as described previously. All mouse tissues assayed contain SNORF25 RNA. Highest levels of mouse SNORF25 RNA are found in central nervous system structures with the highest levels found in the amygdala. Similar expression levels are found in all other CNS regions assayed. In peripheral tissues, highest levels of SNORF25 RNA are found in the duodenum and lung, followed by pancreas, kidney and spleen. This pattern is similar to that found in rat, with the exception of the spleen, where rat SNORF25 RNA was not detected.

The overall expression pattern of SNORF25 in the mouse is similar to that found in rat however, it is profoundly different from the expression pattern in human. In both mouse and rat, the highest levels of expression are in CNS regions. In the human the primary organ expressing SNORF25 RNA is the pancreas. Little human SNORF25 RNA is found expressed in CNS regions or other peripheral organs. These different expression patterns strongly suggest a CNS role for this receptor in rodents, and a peripheral role, perhaps relating to endocrine regulation in humans.

TABLE 1

Distribution of mRNA coding for human SNORF25 receptors using qRT-PCR
mRNA encoding SNORF25h is expressed as % of highest expressing tissue.

| Region | qRT-PCR % of max | Potential applications |
|---|---|---|
| heart | 0.31 | cardiovascular indications |
| kidney | 0.62 | hypertension, electrolyte balance |
| liver | 0.18 | diabetes |
| lung | 0.32 | respiratory disorders, asthma |
| pancreas | 100 | diabetes, endocrine disorders |
| pituitary | 0.03 | endocrine/neuroendocrine regulation |
| placenta | 0.42 | gestational abnormalities |
| small intestine | 4.63 | gastrointestinal disorders |
| spleen | 1.50 | immune disorders |
| stomach | 12.60 | gastrointestinal disorders |
| striated muscle | 0.32 | musculoskeletal disorders |
| amygdala | 0.18 | depression, phobias, anxiety, mood disorders |
| caudate-putamen | 0.17 | modulation of dopaminergic function |
| cerebellum | 0.06 | motor coordination |
| cerebral cortex | 0.01 | sensory and motor integration, cognition |
| hippocampus | 0.27 | cognition/memory |
| spinal cord | 0.00 | analgesia, sensory modulation and transmission |
| substantia nigra | 0.05 | modulation of dopaminergic function. modulation of motor coordination. |
| thalamus | 0.60 | sensory integration |
| fetal brain | 0.14 | developmental disorders |
| fetal lung | 0.04 | developmental disorders |
| fetal kidney | 0.90 | developmental disorders |
| fetal liver | 82.63 | developmental disorders |

TABLE 2

Distribution of mRNA coding for rat SNORF25 receptors using qRT-PCR
mRNA encoding SNORF25r is expressed as % of highest expressing tissue.

| Tissue | qRT-PCR % of max | Potential applications |
|---|---|---|
| adipose tissue | 9.08 | metabolic disorders |
| adrenal cortex | 8.78 | regulation of steroid hormones |
| adrenal medulla | 16.34 | regulation of epinephrine release |
| colon | 24.15 | gastrointestinal disorders |
| duodenum | 18.89 | gastrointestinal disorders |
| heart | 11.98 | cardiovascular indications |
| kidney | 15.86 | electrolyte balance, hypertension |
| liver | trace | diabetes |
| lung | 32.57 | respiratory disorders, asthma |
| ovary | 17.74 | reproductive function |
| pancreas | 30.45 | diabetes, endocrine disorders |
| spleen | not detected | immune disorders |
| stomach | 3.44 | gastrointestinal disorders |
| striated muscle | 1.04 | musculoskeletal disorders |
| testes | 5.10 | reproductive function |
| urinary bladder | 7.87 | urinary incontinence |
| vas deferens | 7.16 | reproductive function |
| celiac plexus | 17.82 | modulation of autonomic innervation |
| cerebellum | 84.14 | motor coordination |
| cerebral cortex | 83.54 | Sensory and motor integration, cognition |
| choroid plexus | 66.59 | regulation of cerebrospinal fluid |
| dorsal root ganglia | 38.14 | sensory transmission |
| hippocampus | 100 | cognition/memory |
| hypothalamus | 67.19 | appetite/obesity, neuroendocrine regulation |
| medulla | 52.66 | analgesia, motor coordination |
| olfactory bulb | 6.66 | olfaction |
| pineal gland | 41.16 | regulation of melatonin release |
| spinal cord | 31.72 | analgesia, sensory modulation and transmission |
| trigeminal ganglia | 42.98 | sensory transmission |

TABLE 3

Distribution of mRNA coding for mouse SNORF25 receptors using qRT-PCR
mRNA encoding SNORF25m is expressed as % of highest expressing tissue.

| Region | qRT-PCR % of max | Potential applications |
|---|---|---|
| amygdala | 100.00 | Depression, |
| hypothalamus | 88.43 | Appetite/obesity, neuroendocrine regulation, |

TABLE 3-continued

Distribution of mRNA coding for mouse SNORF25 receptors using qRT-PCR
mRNA encoding SNORF25m is expressed as % of highest expressing tissue.

| Region | qRT-PCR % of max | Potential applications |
|---|---|---|
| whole brain | 84.46 | |
| medulla oblongata | 84.30 | analgesia, modulation of autonomic function, sensory transmission and modulation |
| spinal cord | 82.31 | analgesia, sensory modulation and transmission |
| cerebral cortex | 79.83 | Sensory and motor integration, cognition |
| cerebellum | 61.49 | motor coordination |
| duodenum | 50.41 | gastrointestinal disorders |
| lung | 46.94 | respiratory disorders, asthma |
| pancreas | 29.42 | diabetes, endocrine disorders |
| kidney | 23.06 | electrolyte balance, hypertension |
| spleen | 21.32 | immune disorders |
| liver | 14.21 | diabetes |
| stomach | 8.26 | gastrointestinal disorders |
| testes | 7.97 | reproductive function |
| adipose | 5.17 | metabolic disorders |
| heart | 3.91 | cardiovascular indications |

Controls

The selectivity of the DIG-labeled riboprobes to hybridize only to the mouse SNORF25 mRNA was verified by performing in situ hybridization on transiently transfected COS-7 cells as described in Methods. The results indicate that the hybridization of the disparate mouse SNORF25 antisense riboprobes selectively recognized mouse SNORF25 mRNA. Specifically, hybridization signal resulted only in the COS-7 cells transfected with SNORF25 gene. No hybridization signal was observed in cells transfected with mouse SNORF25 using the sense riboprobes or in the mock-transfected cells with either antisense or sense riboprobes.

The specificity of hybridization signals in the tissues was confirmed by a series of controls outlined in the Methods. First, riboprobes made to disparate regions of the mouse SNORF25 gene resulted in identical pattern of hybridization throughout all regions of the mouse CNS. In addition, the use of heterologous riboprobes verified that the hybridization signal was a result of specific base pairing of the SNORF25 probe and the SNORF25 mRNA. The hybridization signal obtained using the heterologous probe did not resemble that obtained using the SNORF25 riboprobes. Thirdly, the sense riboprobes did not result in a specific hybridization signal in the tissues but rather a generalized bluish-pink background.

Distribution of SNORF25 mRNA in the Mouse CNS

In general mouse SNORF25 mRNA is widely distributed and highly expressed throughout the mouse CNS. The expression levels and tissue localization appear to be concordant with the expression levels and regional localization determined by qRT-PCR (Table 3).

Olfactory System

A heavy hybridization signal for mSNORF25 mRNA was found in several regions of the olfactory bulb: the internal granule, and the internal and external plexiform layers. An intense signal was found in the mitral cells. The cells of the anterior olfactory nucleus were heavily labeled while the small round cells of the islands of Calleja showed an intense labeling. A moderate labeling was detected in cells of the olfactory tubercle.

Telencephalon

Moderate to heavy hybridization signal was found in many cells in lamina II, III, and V of the cerebral cortex. Scarce moderately labeled cells were observed in lamina VI and scattered weakly labeled cells were seen in lamina IV. This expression pattern extended rostrocaudally throughout the cortex. The cingulate and retrosplenial cortices displayed moderate to weak cell labeling, respectively. Heavy labeling was present in the dorsal endopiriform cortex and an intense labeling was seen in cells in the piriform cortex.

The highest labeling in the basal ganglia was found in the globus pallidus. Heavily labeled medium sized cells were scattered throughout the globus pallidus. the caudate-putamen and medial globus pallidus (entopeduncular nucleus) contained weak labeling and there was a moderate labeling of cells in the nucleus accumbens.

Several nuclei of the basal forebrain were found to contain heavy hybridization signal: the medial septal and the horizontal and vertical diagonal band nuclei. The lateral septal nuclei, substantia innominata and the ventral pallidum contained moderate hybridization signals.

Hybridization was not uniform throughout the various nuclei of the amygdala. Heavy hybridization was seen in the nucleus of the lateral olfactory tract with moderate signal in the nuclei of the basolateral amygdaloid group, medial amygdaloid and the cortical-like nuclei (anterior and posteromedial cortical amygdaloid nuclei), and the amygdalopiriform transition area. A weak signal was detected in the lateral and central nuclei. In the medial division of the extended amygdala, a moderate hybridization signal was observed in the various divisions of the bed nucleus of the stria terminalis.

In general, cell labeling in the dorsal and ventral regions of the hippocampus was heavy. Hybridization signal was observed in the pyramidal-shaped cells in fields CA1, CA2, CA3 of the hippocampus and polymorph layer dentate gyrus, and in the small round cells of the dentate gyrus. Weak hybridization signal was seen in the subiculum with moderate labeling in the induseum griseum.

Diencephalon

Several hypothalamic nuclei were heavily labeled: the median preoptic area, the paraventricular, ventromedial, arcuate and supraoptic nuclei. Moderate labeling was observed in the anterior and lateral hypothalamic areas and in the dorsomedial hypothalamic nucleus. Lighter labeling was detected in the lateral preoptic and retrochiasmatic areas and in the median preoptic nucleus.

Labeling intensity varied among the thalamic nuclei. The highest labeling was observed in the paraventricular, submedius (gelatinosus), and the medial geniculate nuclei. Moderate hybridization signal was evident in cells in the anterodorsal, mediodorsal, medial habenular, paracentral, centromedial and parafascicular nuclei. Weak hybridization signal was present in the lateral habenular, laterodorsal, reuniens, ventroposterior, ventromedial and ventrolateral nuclei.

Mesencephalon

The interpeduncular and red nuclei contained the highest hybridization signal in the midbrain. Heavy labeling was detected in the large cells of the red nucleus and in all division of the interpeduncular nucleus. Moderate labeling was observed in varios nuclei in this region: the dorsal and median raphe nuclei, nucleus of Darkschewitsch, Edinger-Westphal nucleus, the pontine reticular nucleus, oral part, reticular periolivary region, ventral tegmental area, and substantia nigra, reticular part. Weak hybridization signal was found in the cells of the superior colliculus, periaqueductal gray, and compact part of the substantia nigra.

Rhombencephalon (Cerebellum/Pons/Medulla Oblongata)

The highest labeling in the pons/medulla occurred in the raphe magnus and spinal trigeminal nuclei. SNORF25 hybridization signal was moderate to heavy throughout the nuclei of the tegmentum and reticular formation. A moderate hybridization signal was seen in the nucleus of the solitary tract, raphe obscurus, raphe pallidus, and the facial nucleus while a weaker signal was observed in the lateral parabrachial, mesencephalic and motor trigeminal, and gracile nuclei.

The Purkinje cells of the cerebellum exhibited an intense staining while the small round granule cells displayed a variety of expression levels. Moderately labeled cells were seen scattered throughout the molecular layer. Cells in the interposed and lateral (dentate) cerebellar nuclei contained a moderate hybridization signal.

Spinal Cord

SNORF25 hybridization signal was moderately intense throughout all the lamina of the dorsal and ventral horns of the spinal cord except for cells in lamina IX of the ventral horn that exhibited weak labeling.

Circumventricular Organs

The cells of the area postrema contained a heavy hybridization signal.

TABLE 5

Distribution of SNORF25 mRNA in the mouse CNS using in situ hybridization histochemistry and digoxigenin labeled riboprobes. The intensity of hybridization signal in various region of the mouse brain, as defined by Paxinos and Watson (1998), were qualitative evaluations based on the relative staining intensity (blue color) observed in individual cells at the microscopic level. The strength of the mSNORF25 hybridization signal was graded as weak (+), or moderate (++) or heavy (+++) or intense (++++).

| Region | Mouse SNORF25 mRNA | Potential Application |
| --- | --- | --- |
| Olfactory bulb: | | Modulation of olfactory sensation |
| internal granule layer | +++ | |
| glomerular layer | ND | |
| external plexiform layer | ++ | |
| mitral cell layer | ++++ | |
| anterior olfactory nu | +++ | |
| olfactory tubercle | ++ | |
| islands of Calleja | +++ | |
| Telencephalon: Cerebral cortex | | Sensory integration |
| taenia tecta | ++++ | |
| frontal cortex | +++ | Emotions |
| insular cortex | +++ | Visceral sensory cortex. Sensation of hunger pangs, abdominal fullness and breath-holding sensation |
| cingulate cortex | ++ | Visceral motor region. Stimulation causes changes in gastric contractions and changes in blood pressure. Also involved in emotions. |
| retrosplenial cortex | + | |
| parietal cortex | +++ | Processing of visual stimuli |
| occipital cortex | +++ | |
| temporal cortex | +++ | Processing of auditory stimuli |
| entorhinal cortex | +++ | Processing of visceral information |
| dorsal endopiriform nu | +++ | |
| piriform cortex | ++++ | Integration/transmission of incoming olfactory information |
| Basal Ganglia | | Control of normal voluntary movement. The treatment of Parkinson's disease, Huntington disease, and hemiballismus. |
| accumbens nu | ++ | Modulation of dopaminergic transmission. Treatment of drug addiction. This region is particularly sensitive to psychoactive drugs. |
| caudate-putamen | + | Treatment of motor disorders; sensory/motor integration |
| globus pallidus | +++ | Treatment of movement disorders. |
| Medial globus pallidus (entopeduncular nu) | + | |
| Septum and Basal forebrain | | The control of physiological and behavioral processes related to higher function (learning and memory), emotions, fear, aggression, stress, and autonomic regulation (water/food intake). |
| medial septal nu | +++ | Treatment of Alzheimer Disease. Cognitive enhancement via cholinergic system |
| lateral septal nu, dorsal part | + | Modulation of integration of stimuli associated with adaptation |
| lateral septal nu, intermediate | ++ | |
| ventral pallidum | ++ | Treatment of Alzheimer Disease—cholinergic system |
| nu of horizontal limb diagonal band | +++ | Treatment of Alzheimer Disease—cholinergic system |

TABLE 5-continued

Distribution of SNORF25 mRNA in the mouse CNS using in situ hybridization histochemistry and digoxigenin labeled riboprobes. The intensity of hybridization signal in various region of the mouse brain, as defined by Paxinos and Watson (1998), were qualitative evaluations based on the relative staining intensity (blue color) observed in individual cells at the microscopic level. The strength of the mSNORF25 hybridization signal was graded as weak (+), or moderate (++) or heavy (+++) or intense (++++).

| Region | Mouse SNORF25 mRNA | Potential Application |
|---|---|---|
| nu of vertical diagonal band | +++ | Treatment of Alzheimer Disease—cholinergic system |
| substantia innominata | ++ | Treatment of Alzheimer Disease—cholinergic system |
| Amygdala | | The treatment of anxiety and fear (Anxiolytic). Activation of this region results in the reduction in panic attacks. Modulation of endocrine functions and integrated behaviors such as defense, ingestion, reproduction and learning. |
| lateral nu | + | |
| basomedial nu | ++ | Olfactory sensation |
| basolateral nu | ++ | Sensory inflow for fear and anxiety |
| medial amygdaloid nu | ++ | Olfactory amygdala |
| central nu | + | Treatment of anxiety and fear. Arousal and conscious perception of emotion. |
| anterior cortical nu | ++ | Olfaction |
| posteromedial cortical nu | ++ | Vomeronasal amygdala; olfaction |
| amygdalopiriform transition area | ++ | Olfaction |
| nu of the lateral olfactory tract | +++ | Olfaction |
| bed nu stria terminalis | ++ | Modulation of the limbic system |
| Hippocampus | | Memory consolidation and retention. Treatment of cognitive and memory disorders. Treatment of Alzheimer Disease. |
| field CA1 of hippocampus | +++ | |
| field CA2 of hippocampus | +++ | |
| field CA3 of hippocampus | +++ | Facilitation of LTP |
| subiculum | + | |
| dentate gyrus | +++ | |
| polymorph layer dentate gyrus | +++ | |
| induseum griseum | ++ | |
| Diencephalon: | | |
| Hypothalamus | | Treatment of disorders in the regulation of endocrine function, reproductive behaviors, blood pressure, electrolyte composition, and regulation of body temperature. Treatment of eating disorders (energy metabolism, feeding, digestion and metabolic rate). Treatment of stress. |
| median preoptic nu | + | |
| median preoptic area | +++ | Regulation of gonadotropin secretion and reproductive behaviors |
| lateral preoptic area | + | |
| suprachiasmatic nu | ND | Treatment of sleep disorders. |
| paraventricular nu | +++ | Treatment of appetite disorders (obesity) |
| arcuate nu | +++ | Appetite control/obesity |
| anterior hypothalamic area | ++ | Treatment of disorders of sensing body temperature. Lesion causes hyperthermia. |
| retrochiasmatic area | + | |
| lateral hypothalamus | ++ | Treatment of eating disorders |
| dorsomedial nu | ++ | Treatment of eating disorders |
| ventromedial nu | +++ | Control of food intake. Lesion produces hyperphagia; stimulation suppresses feeding |
| supraoptic nu | +++ | Treatment of disorders in the synthesis of oxytocin and arginine vasopressin |
| Thalamus | | Analgesia/Modulation of sensory information |
| paraventricular nu | +++ | Modulation of motor and behavioral responses to pain |
| centromedial nu | ++ | Modulation of motor and behavioral responses to pain |
| paracentral nu | ++ | |
| parafascicular nu | ++ | Modulation of motor and behavioral responses to pain |
| anterodorsal nu | ++ | Modulation of eye movement |
| mediodorsal nu | ++ | Modulation of information between limbic structures of the ventral forebrain and prefrontal cortex |
| laterodorsal nu | + | |
| reuniens nu | + | Modulation of thalamic input to ventral hippocampus and entorhinal cortex |
| submedius (gelatinosus) thalamic nu | +++ | Olfaction, analgesia |
| medial habenular nu | ++ | Anxiety/sleep disorders/analgesia in chronic pain |
| lateral habenular nu | + | |
| ventrolateral nu | + | Treatment of motor disorders |
| ventromedial nu | + | Treatment of motor disorders |
| ventral posterolateral nu | + | Analgesia |
| reticular nu | − | Alertness/sedation |
| zona incerta | + | |

TABLE 5-continued

Distribution of SNORF25 mRNA in the mouse CNS using in situ hybridization histochemistry and digoxigenin labeled riboprobes. The intensity of hybridization signal in various region of the mouse brain, as defined by Paxinos and Watson (1998), were qualitative evaluations based on the relative staining intensity (blue color) observed in individual cells at the microscopic level. The strength of the mSNORF25 hybridization signal was graded as weak (+), or moderate (++) or heavy (+++) or intense (++++).

| Region | Mouse SNORF25 mRNA | Potential Application |
|---|---|---|
| medial geniculate nu | +++ | Modulation of auditory system |
| dorsal lateral geniculate nu | ++ | Modulation of visual perception |
| Mesencephalon: | | |
| superior colliculus | + | Modulation of vision |
| periaqueductal gray | + | Analgesia |
| nu of Darkschewitsch | ++ | |
| Edinger-Westphal nu | ++ | Controls pupillary constriction and lens accomodation |
| dorsal raphe nu | ++ | Analgesia |
| median raphe nu | ++ | |
| pontine reticular nu, oral part | ++ | |
| reticular periolivary region | | Treatment of sleep disorders. Lesion causes disruption of REM sleep. |
| red nu | +++ | Involved in the execution of motor behavior |
| Lateral reticular nu | ++ | Motor control |
| ventral tegmental area | ++ | Modulation of the integration of motor behavior and adaptive responses |
| substantia nigra, reticular part | ++ | Treatment of motor control dysfunction |
| substantia nigra, compact part | + | Treatment of motor control dysfunction (Parkinson Disease) |
| paranigral nu | ++ | |
| interpeduncular nu | +++ | Analgesia |
| Rhombencephalon: Medulla oblongata/Pons | | Analgesia |
| raphe magnus nu | +++ | Analgesia; modulation of the perception of pain |
| raphe pallidus nu | ++ | Regulation of tone in motor systems and pain perception. Regulation of ANS. |
| raphe obscurus nu | ++ | Regulation of tone in motor systems and pain perception. Regulation of ANS. |
| spinal trigeminal nu | +++ | Analgesia and temperature sensation in the face |
| medullary reticular nu | +++ | Involved in movement, posture, pain, autonomic functions and arousal |
| ventral tegmental tegmental nu | ++ | Ascending arousal system |
| reticular tegmental nu | ++ | |
| pontine reticular nu, oral part | +++ | |
| lateral reticular nu | ++ | |
| parvicellular reticular nu | ++ | |
| lateral parabrachial nu | + | Modulation of visceral sensory information |
| motor trigeminal nu | + | Innervation of muscles used in chewing |
| mesencephalic trigeminal nu | + | |
| medial vestibular nu | ++ | Maintenance of balance and equilibrium |
| spinal vestibular nu | ++ | |
| trapezoid nu | ++ | Audition |
| cuneate nu | +++ | Analgesia |
| gigantocellular reticular nu | ++ | Analgesia; inhibition and disinhibition of brainstem |
| dorsal paragigantocellular nu | +++ | |
| gigantocellular reticular nu, alpha | ++ | Analgesia |
| lateral paragiganto-cellular reticular nu | ++ | |
| prepositus hypoglossal nu | + | Position and movement of the eyes/Modulation of arterial pressure and heart rate |
| nu soltary tract | ++ | Hypertension |
| gracile nu | + | |
| facial nu(7) | ++ | Oromotor nucleus |
| inferior olivary nu | +/− | |
| Cerebellum | | Treatment of dysfunction of motor coordination |
| granule cells | + | |
| Purkinje cells | +++ | |
| molecular layer | + | |
| Deep cerebellar nuclei | ++ | Involved in the execution of motor behavior; analgesia |
| Spinal cord: | | Analgesia |
| dorsal horn | +++ | |
| ventral horn | +++ | |
| Circumventricular organs: | | |
| area postrema | +++ | Emesis; food intake, conditioned taste aversions, body weight and homeostasis, baroreflex and cardiovascular control |

ND = not determined

Discussion

The anatomical distribution of SNORF25 mRNA in the mouse CNS was determined using in situ hybridization histochemistry and digoxigenin-labeled riboprobes made to disparate regions of the SNORF25 gene. The specificity of the riboprobes for mouse SNORF25 mRNA was verified by hybridization using COS-7 cells transiently transfected with the mSNORF25 gene and by hybridizing the tissue sections with (1) heterologous riboprobes, (2) multiple probes made to disparate regions of the gene, and (3) sense riboprobes. The expression levels of mSNORF25 mRNA in the mouse brain did not require amplification procedures; thus direct immunodetection of the DIG-labeled riboprobes was performed. By light microscopy the chromogen precipitate (NBT/BCIP (blue color)) was found to be distributed in the cytoplasm of neuronal profiles. No hybridization was observed in fiber tracts. The results demonstrate that the mRNA for mouse SNORF25 is widely distributed throughout the mouse CNS, and predominantly moderately expressed (Table 5). Several regions exhibited intense expression of mSNORF25 mRNA: the mitral cells of the olfactory bulb, piriform cortex and the cerebellar Purkinje cells. Heavy mSNORF25 expression was observed in the cerebral cortex and various nuclei of the hypothalamus, hippocampus, and brain stem. A heavy hybridization signal was also detected in almost all lamina of the dorsal and ventral spinal cord. Moderate hybridization occurred in the several mesencephalic structures and in the reticular and tegmental areas of the brain. Light hybridization was seen in a variety of diencephalic and mesencephalic nuclei, and in lamina IX of the spinal cord.

The distribution and expression levels of mouse SNORF25 mRNA in selected regions of the mouse CNS by in situ hybridization histochemistry is in concordance with the reported qRT-PCR data (Table 3).

Potential Therapeutic Application

The wide distribution of the SNORF25 receptor in the mouse CNS suggests that this receptor could potentially play a role in a variety of physiological processes. SNORF25 mRNA is expressed in several brain regions that are involved in the relaying and processing of a variety of sensory information. mSNORF25 mRNA has been identified throughout the olfactory system: the olfactory bulb, anterior olfactory nucleus, piriform cortex, nucleus of the lateral olfactory tract, medial amygdaloid nucleus and the entorhinal cortex. This localization suggests a possible role for SNORF25 in olfactory discrimination and cognition, feeding (food selection), reproduction, aggressiveness and emotional responses.

SNORF25 mRNA has been found in nuclei of the visual and auditory systems and thus may be a modulator of these senses. SNORF25 has also been localized in several nuclei of the visual system: the dorsal lateral geniculate nucleus and superior colliculus, as well as in the occipital cortex. Its localization in the Edinger-Westphal nucleus suggests that SNORF25 may be involved in pupillary constriction and lens accomodation.

The expression of SNORF25 mRNA throughout the cerebral cortex suggests a potential role in the processing of a variety of somatosensory and limbic system (cingulate and entorhinal cortices) information. Furthermore, the localization in the cortex implies a role in cognition for this receptor and a potential therapeutic target in the treatment of Alzheimer Disease. Further support for possible cognitive involvement of this receptor comes from its localization in several regions of the cholinergic basal forebrain and the hippocampus, regions known to show neurodegenerative changes in Alzheimer Disease.

SNORF25 may be involved in the modulation of integrated behavior such as defense, ingestion, aggression, reproduction and learning as suggested by its localization in the amygdala and extended amygdala (bed nucleus of the stria terminalis). Activation of this brain region results in the reduction in panic attacks; thus this receptor may be a potential therapeutic target for the development of anxiolytics in the treatment of anxiety and fear or in the treatment of mood disorders.

Another potential role for SNORF25 may be in modulating the integration of motor behavior and adaptive responses. SNORF25 mRNA was present throughout basal ganglia structures (caudate-putamen, globus pallidus, entopeduncular nucleus) and the ventral tegmental area, regions involved in the control of normal voluntary movement. SNORF25 may therefore be a potential target in the treatment of Parkinson's disease, Huntington disease, and hemiballismus. The localization of SNORF25 mRNA in the accumbens nucleus suggests that this receptor may be a potential therapeutic target in the treatment of drug addiction. This region is part of the brain reward circuit and is sensitive to addictive drugs.

The extensive localization in the hypothalamus implies a potential role for SNORF25 in not only the regulation of food intake (paraventricular, ventromedial and arcuate nuclei), but also the regulation of endocrine functions (preoptic area), and homeostasis. This receptor provides a prospective therapeutic target in the treatment of eating (obesity) and endocrine disorders.

The expression in the thalamus supports a possible modulatory role in the transmission of somtosensory (nociceptive) information to the cortex and the exchange of information between the forebrain and midbrain limbic system (habenula). SNORF25 mRNA was localized in several medullary relay nuclei, the cuneate and gracile nuclei that receive somatosensory information and project to the ventrobasal thalamus (ventroposteriomedial and ventroposteriorlateral nuclei) that also express SNORF25 mRNA.

SNORF25 may play a role in the regulation of somatic sensorimotor activity in the control of movement. SNORF25 mRNA has been observed in several pontine precerebellar nuclei, the red nucleus, the cerebellar cortex, and the deep cerebellar nuclei.

SNORF25 may be a potential therapeutic target in the treatment Of pain. SNORF25 has been localized in brain regions that are involved in the perception of pain or part of the endogenous analgesia system (raphe nuclei). SNORF25 mRNA was observed in the periaqueductal gray, raphe nuclei, and the trigeminal sensory nuclei. Additional support for an analgesic role for SNORF25 is the localization of mRNA in the dorsal and ventral horns of the spinal cord, thereby implying that this receptor may possibly modulate incoming as well as descending sensory information in addition to spinal motor reflexes.

REFERENCES

Austin, C. E. and Foreman, J. C., "The effect of platelet-activating factor on the responsiveness of the human nasal airway", Br. J. Pharmacol. 110: 113–118 (1993).

Bartemes, K. R., et al., "Endogenous platelet-activating factor is critically involved in effector functions of eosinophils stimulated with IL-5 or IgG", J. Immunol. 162: 2982–2989 (1999).

Bazan, N. G., "The neuromessenger platelet-activating factor in plasticity and neurodegeneration", Prog. Brain Res. 118: 281–291 (1998).

Bito, H., et al., "Cloning, expression and tissue distribution of rat platelet-activating-factor-receptor cDNA", Eur. J. Biochem. 221: 211–218 (1994).

Borowsky, B., et al. (1999) Cloning and characterization of the human galanin GALR2 receptor Peptides 19: 1771–1781.

Bowman, W. C. and Rand, M. J., eds., "The eye and drugs affecting ocular function", In: Textbook of Pharmacology. Second Edition, London: Blackwell Scientific Publications. p. 29.22–29.27 (1980).

Bradford, M. M., "A rapid and sensitive method for the quantitation of microgram quantities of protein utilizing the principle of protein-dye binding", Anal. Biochem. 72: 248–254 (1976).

Breitman, T., et al., "Induction of differentiation of human promyelocytic leukemia cell line (HL-60) by retinoic acid", Proc. Natl. Ada. Sci. 77: 2936–2940 (1980).

Burns, C. C., et al., "Indentification and deletion of sequences required for feline leukemia virus RNA packaging and construction of a high-titer feline leukemia virus packaging cell line", Virology 222 (1): 14–20 (1996).

Bush, et al., "Nerve growth factor potentiates bradykinin-induced calcium influx and release in PC12 cells", *J. Neurochem.* 57: 562–574 (1991).

Chao, W. and Olson, M. S., "Platelet activating factor: receptors and signal transduction", *Biochem. J.* 292: 617–629 (1993).

Chao, W., et al., "Identification of receptors for platelet-activating factor in rat Kupffer cells", *J. Biol. Chem.* 264: 13591–13598 (1989).

Chau, L. Y., et al., "Possible existence of two subsets of platelet-activating factor receptor to mediate polyphosphoinositide breakdown and calcium influx in neuroblastome glioma hybrid NG108–15 cells", *J. Neurochem.* 59: 1090–1098 (1992).

Chertow, B. S., et al., "Cellular mechanisms of insulin release: effects of retinoids on rat islet cell-to-cell adhesion, reaggregation, and insulin release", *Diabetes* 32: 568–574 (1983).

Chertow, B. S., et al, "Effects of vitamin A deficiency and repletion on rat insulin secretion in vivo and in vitro from isolated islets", *J. Clin. Invest.* 79: 163–169(1987).

Chertow, B. S., et al., "Cytoplasmic retinoid-binding proteins and retinoid effects on insulin release in RINm5F-cells", *Diabetes* 38: 1544–1548 (1989).

Chu, Y. Y., et al., "Characterization of the rat A2a adenosine receptor gene", *DNA Cell Biol.* 15(4): 329–337 (1996).

Chytil, F., "Retinoids in lung development", *FASEB J.* 10(9): 986–992 (1996).

Connor, M. J. and Sidell, N., "Retinoic acid synthesis in normal and Alzheimer diseased brain and human neural cells", *Mol. Chem. Neurophathol.* 30(3): 239–252 (1997).

Dascal, N., et al., "A trial G protein-activated $K^+$ channel: expression cloning and molecular properties", *Proc. Natl. Acad. Sci. USA* 90:10235–10239 (1993).

Del Cerro, S., et al., "Inhibition of long-term potentiation by an antagonist of platelet-activating factor receptors", *Behav. Neural. Biol.* 54: 213–217 (1990).

Del Sorbo, L., et al., "The synthesis of platelet-activating factor modulates chemotaxis of monocytes induced by HIV-1 Tat", *Eur. J. Immunol.* 29: 1513–1521 (1999).

Demopoulos, C. A., et al., "Intravascular pathobiology of acetyl glyceryl ether phosphocholine (AGEPC), a synthetic platelet-activating factor (PAF). I. Intravenous infusion in guinea pigs", *Immunol. Lett.* 3: 133–135 (1981).

Demopoulos, C. A., et al., "Platelet activating factor. Evidence for 1-O-alkyl-2-acetyl-sn-glyceryl-3-phosphorylcholine as the active component (a new class of lipid chemical mediators)", *J. Biol. Chem.* 254: 9355–9358 (1979).

El-Matwally, T. H. and T. E. Adrian (1999) Optimization of treatment conditions for studying the anticancer effects of retinoids using pancreatic adenocarcinoma as a model. Biochem. Biophy. Res. Commun. 257(2): 596–603.

Faden, A. I. and Halt, P., "Platelet-activating factor reduces spinal cord blood flow and causes behavioural deficits after intrathecal administration in rats through a specific receptor mechanism", *J. Pharmacol. Exp. Ther.* 261: 1064–1070 (1992).

Fink, M. P., "Theraprutic options directed against platelet activating factor, eicosanoids and bradykinin in sepsis", *J. Antimicrob. Chemother.* 41(*SupplA*): 81–94 (1998).

Fong, T. M., et al., "Mutational analysis of neurokinin receptor function" *Can. J. Physio. Pharmacol.* 73(7): 860–865 (1995).

Ford-Hutchinson, A. W., "Neutrophil aggregating properties of PAF-acether and leukotriene B4", *Int. J. Immunopharmacol.* 5: 17–21 (1983).

Gardner, C. R., et al., "Distinct biochemical responses of hepatic macrophages and endothelial cells to platelet-activating factor during endotoxemia", *J. Leukoc. Biol.* 57: 269–274 (1995).

Goldstein, R. E., et al., "Coronary and pulmonary vascular effects of leukotrienes and PAF-acether", *Pharmacol. Res. Commun.* 18(Suppl): 151–162 (1986).

Goodman, A. B., "Three independent lines of evidence suggest retinoids as causal to schizophrenia", *PNAS* 95(13): 7240–7244 (1998).

Gorman, R. R., et al., "Acetyl glyceryl ether phosphorylcholine stimulates leukotriene B4 synthesis and cyclic AMP accumulation in human polymorphonuclear leukocytes", *Adv. Prostaglandin Thromboxane Leukot. Res.* 12: 57–63 (1983).

Gottardis, M. M., et al., "The efficacy of 9-cis retinoic acid in experimental models of cancer", *Breast Cancer Res. and Treat.* 38: 85–96 (1996).

Graziano, M. P. et al., "The amino terminal domain of the glucagon-like peptide-1 receptor is a critical determinant of subtype specificity" Receptors Channels 4(1): 9–17 (1996).

Guan, X. M., et al., "Determination of Structural Domains for G Protein Coupling and Ligand Binding in (3-Adrenergic Receptor" *Mol. Pharmacol.* 48(3): 492–498 (1995).

Gudas, L. J., et al. "Cellular biology and biochemistry of the retinoids" In: Sporn, M. B., Roberts, A. B., Goodman, D. S. eds. *The retinoids: Biology, chemistry, and medicine.* $2^{nd}$ ed. New York: Raven Press. p. 443–520 (1994).

Gundersen, C. B., et al., "Serotonin receptors induced by exogenous messenger RNA in *Xenopus* oocytes" *Proc. R. Soc. Lond. B. Biol. Sci.* 219(1214): 103–109 (1983).

Handa, R. K., et al., "Platelet-activating factor is a renal vasodilator in the anesthetized rat", *Am. J. Physiol.* 258: F1504–1509 (1990).

Heller, A., et al., "Lipid mediators in inflammatory disorders", Drugs 55: 487–496 (1998).

Henson, P. M., "Release of vasoactive amines from rabbit platelets induced by sensitized mononuclear leucocytes and antigen", *J. Exp. Med.* 131: 287–304 (1970).

Hofman, C. and Eichele, G., "Retinoids in development" In: Sporn, M. B., Roberts, A. B., Goodman, D. S. eds. *The retinoids: Biology. chemistry, and medicine.* $2^{nd}$ ed. New York: Raven Press. p. 387–441 (1994).

Honda, Z., et al., "Cloning by functional expression of platelet-activating factor receptor from guinea-pig lung", *Nature* 349: 342–346 (1991).

Honda, Z., et al., "Transfected platelet-activating factor receptor activates mitogen-activated protein (MAP) kinase and MAP kinase kinase in Chinese hamster ovary cells", *J. Biol. Chem.* 269: 2307–2315 (1994).

Hosford, D. J., et al., "Ginkgolides and platelet-activating factor binding sites", *Meth. Enzymol.* 187: 433–446 (1990).

Hwang, S. B., et al., "Specific receptor sites for 1-O-alkyl-2-O-acetyl-sn-glycero-3-phosphocholine (platelet activating factor) on rabbit platelet and guinea pig smooth muscle membranes", *Biochem.* 22: 4756–4763 (1983).

Inanobe, A., et al., "Characterization of G-protein-gated K+channels composed of Kir3.2 subunits in dopaminergic neurons of the substantia nigra" *J. of Neurosci.* 19(3): 1006–1017 (1999).

Johnson, C. D., "Platelet-activating factor and platelet-activating factor antagonists in acute pancreatitis", *Dig. Surg.* 16: 93–101 (1999).

Junier, M. P., et al., "Inhibitory effect of platelet-activating factor (PAF) on luteinizing hormone-releasing hormone and somatostatin release from rat median eminence in vitro correlated with the characterization of specific PAF receptor sites in rat hypothalamus", *Endocrinol.* 123: 72–80 (1988).

Kato, K., et al., "Platelet-activating factor as a potential retrograde messenger in CA1 hippocampal long-term potentiation, *Nature* 367: 175–179 (1994).

Kochanek, P. M., et al., "Cerebrovascular and cerebrometabolic effects of intracarotid infused platelet-activating factor in rats", *J. Cereb. Blood Flow Metab.* 8: 546–551 (1988).

Konturek, S. J., et al., "Role of platelet activating factor in pathogenesis of acute pancreatitis in rats", *Gut* 33: 1268–1274 (1992).

Kornecki, E. and Ehrlich, Y. H., "Neuroregulatory and neuropathological actions of the ether-phospholipid platelet-activating factor", *Science* 240: 1792–1794 (1988).

Krapivinsky, G., et al., "The G-protein-gated atrial $K^+$ channel IKACh is a heteromultimer of two inwardly rectifying K(+)-channel proteins" *Nature* 374:135–141 (1995).

Krapivinsky, G., et al., "The cardiac inward rectifier $K^+$ channel subunit, CIR, does not comprise the ATP-sensitive $K^+$ channel, IKATP", *J. Biol. Chem.* 270:28777–28779 (1995b).

Kubo, Y., et al., "Primary structure and functional expression of a rat G-protein-coupled muscarinic potassium channel" *Nature* 364:802–806 (1993).

Kumar, R., et al., "Production and effects of platelet-activating factor in the rat brain", *Biochim. Biophys. Acta* 963: 375–383 (1988).

Lazareno, S. and Birdsall, N. J. M., "Pharmacological characterization of acetylcholine stimulated [$^{35}$S]-GTPγS binding mediated by human muscarinic m1–m4 receptors: antagonist studies", *Br. J. Pharmacol.* 109: 1120–1127 (1993).

Lee, T. C., et al., "1-alkyl-2-acetyl-sn-glycero-3-phosphocholine (platelet-activating factor) stimulates calcium influx in rabbit platelets", *Biochem. Biophys. Res. Commun.* 102: 1262–1268 (1981).

Lee, T. C., et al., "Stimulation of calcium uptake by 1-alkyl-2-acetyl-sn-glycero-3-phosphocholine (platelet-activating factor) in rabbit platelets: possible involvement of the lipoxygenase pathway", *Arch. Biochem. Biophys.* 223: 33–39 (1983).

Lefort, J., et al., "Is platelet-activating factor involved in bronchopulmonary hyperresponsiveness?", *J. Lipid Mediat.* 5: 163–167 (1992).

Liu, L., et al., "Triple role of platelet-activating factor in eosinophil migration across monolayers of lung epithelial cells: eosinophil chemoattractant and priming agent and epithelial cell activator", *J. Immunol.* 161: 3064–3070 (1998).

Lopez-Novoa, J. M., "Potential role of platelet activating factor in acute renal failure", *Kidney Int.* 55: 1672–1682 (1999).

Loucks, E. B., et al., "Platelet-activating factor antagonism: a new concept in the management of regional myocardial iscemia-reperfusion injury", *J. Invest. Surg.* 10: 312–338 (1997).

Maclennan, K. M., et al., "Platelet-activating factor in the CNS", *Prog. Neurobiol.* 50: 585–596 (1996).

Manglesdorf, D. J., et al. "The retinoid receptors", In: Sporn, M. B., Roberts, A. B., Goodman, D. S. eds. *The retinoids: Biology, chemistry, and medicine.* $2^{nd}$ ed. New York: Raven Press. p. 319–349 (1994).

Marcheselli, V. L., et al., "Distinct platelet-activating factor binding sites in synaptic endings and in intracellular membranes of rat cerebral cortex", *J. Biol. Chem.* 265: 9140–9145 (1990).

Martin, S., et al., "HL-60 cells induced to differentiate towards neutrophils subsequently die via apoptosis" *Clin. Exp. Immunol.* 79: 448–453 (1990).

Martinez-Cuesta, M. A., et al., "Involvement of prostaglandins and 5-hydroxytryptamine in the contractile effect of platelet-activating factor in rat isolated gastric corpus", *J. Pharm. Pharmacol.* 48: 955–958 (1996).

Metz, S. A., "Ether-linked Lysophospholipids Initiate Insulin Secretin. Lysophospholipids May Mediate Effects of Phospholipase A2 Activation on Hormone Release" *Diabetes* 35(7): 808–817 (1986).

Miller, J., and Germain, R. N. "Efficient cell surface expression of class II MHC molecules in the absence of associated invariant chain", *J. Exp. Med.* 164(5): 1478–1489 (1986).

Milligan, G., et al., "Use of chimeric G(proteins in drug discovery" *TIPS (In press).*

Nagase, T., et al., "Airway responsiveness in transgenic mice overexpressing paltelet-activating factor receptor. Roles of thromboxanes and leukotrienes", *Am. J. Respir. Crti. Care Med.* 156: 1621–1627 (1997).

Nakamura, M., et al., "Molecular cloning and expression of platelet-activating factor receptor from human leucocytes", *J. Biol. Chem.* 266: 20400–20405 (1991).

Nakashima, S., et al., "Mechanism of arachidonic acid liberation in platelet-activating factor-stimulated human polymorphonuclear neutrophils", *J. Immunol.* 143: 1295–1302 (1989).

Ng, D. S. and Wong, K., "Specific binding of platelet-activating factor (PAF) by human peripheral blood mononuclear leucocytes", *Biochem. Biophys. Res. Commun.* 155: 311–316 (1988).

Ohmura, T., et al., "Induction of cellular DNA synthesis in the pancreas and kidneys of rats by peroxisome proliferators, 9-cis retinoic acid, and 3,3',5-triiodo-L-thyronine", *Cancer Res.* 57: 795–798 (1997).

Orfanos, C. E., et al., "Current use and future potential role of retinoids in dermatology", *Drugs* 53(3): 358–388(1997).

Page, C. P., "Mechanisms of hyperresponsiveness: Platelet activating factor" *Am. Rev. Respir. Dis.* 145: S31–S33 (1992).

Paxinos, G. and Watson, C., (1998) The Rat Brain in Stereotaxic Coordinates. San Diego: Academic Press, Inc.

Piper, P. J. and Stewart, A. G., "coronary vasoconstriction in the rat isolated perfused heart induced by platelet-activating factor is mediated by leukotriene C4", *Br. J. Pharmacol.* 88: 595–605 (1986).

Pritze, S., et al., "Effect of platelet-activating factor on porcine pulmonary blood vessels in vitro", *Naunyn Schmiedebergs Arch. Pharmacol.* 344: 495–499 (1991).

Prpic, V., et al., "Biochemical and functional responses stimulated by platelet-activating factor in murine peritoneal macrophages", *J. Cell Biol.* 107: 363–372 (1988).

Quick, M. W. and Lester, H. A., "Methods for expression of excitability proteins in *Xenopus* oocytes", *Meth. Neurosci.* 19: 261–279 (1994).

Redfern, C. P., et al., "Gene expression and neuroblastoma cell differentiation in response to retinoic acid: differential effects of 9-cis and all-trans retinoic acid" *Eur. J. Cancer* 31A(4): 486–494 (1995).

Riordan, J. R., "The cystic fibrosis transmembrane conductance regulator", *Ann. Rev. Physiol.* 55: 609–630 (1993).

Rosenwicz, S., Wollbergs, K., Von Lampe, B., Matthes, H., Kaiser, A., and E. O. Riecken (1997) Retinoids inhibit adhesion to laminin in human pancreatic carcinoma cells via the alpha 106 beta 1-integrin receptor. Gastroenterology 112(2): 532–542.

Rosenwicz, S., Stier, U., Brembeck, F., Kaiser, A., Papadimitriou, C. A., Berdel, W. E., Wiedenmann, B., and E. O. Riecken (1995) Retinoids: effects on growth, differentiation, and nuclear receptor expression in human pancreatic carcinoma cell lines. Gastroenterology 109(5): 1646–1660.

Sabichi, A. L., et al., "Retinoids in the chemoprevention of bladder cancer", Curr. Opin. Oncol. 10(5): 479–484 (1998).

Salon, J. A. and Owicki, J. A., "Real-time measurements of receptor activity: Application of microphysiometric techniques to receptor biology" Meth. Neurosci. 25: 201–224 (1996).

Sanchez-Crespo, M., et al., "Non-platelet-mediated vascular actions of 1-O-alkyl-2-acetyl-sn-3-glyceryl phosphorylcholine (a synthetic PAF)", Agents Actions 11: 565–566 (1981).

Shimizu, T., et al., "Platelet-activating factor receptor and signal transduction", Biochem. Pharmacol. 44: 1001–1008 (1992).

Shukla, S. D., "Platelet-activating factor receptor and signal transduction mechanisms", FASEB J. 6: 2296–2301 (1992).

Smith, K. E., et al., "Expression cloning of a rat hypothalamic galanin receptor coupled to phosphoinositide turnover", J. Biol. Chem. 272: 24612–24616 (1997).

Sporn, M., and Roberts, A., "Role of retinoids in differentiation and carcinogenesis" J. Natl. Cancer Inst. 73: 1381–1387(1984).

Spurney, R. F., et al., "The C-terminus of the thromboxane receptor contributes to coupling and desensitization in a mouse mesangial cell line", J. Pharmacol. Exp. Ther. 283(1): 207–215 (1997).

Stack, W. A. and Hawkey, C. J., "Specific mediator-directed therapy for gastrointestinal diseases", Eur. J. Gastroenterol. Hepatol. 9: 1056–1061 (1997).

Takahashi, T., et al., ARat brain serotonin receptors in Xenopus oocytes are coupled by intracellular calcium to endogenous channels@ Proc. Natl. Acad. Sci. USA 84(14): 5063–5067 (1987).

Tian, W., et al., "Determinants of alpha-Adrenergic Receptor Activation of G protein: Evidence for a Precoupled Receptor/G protein State" Molecular Pharm. 45: 524–553 (1994).

Underwood, D. J. et al., "Structural model of antagonist and agonist binding to the angiotensin 11, AT1 subtype, G protein coupled receptor", Chem. Biol. 1(4): 211–221 (1994).

Valone, F. H., "Identification of platelet-activating factor receptors in P388D1 murine macrophages", J. Immunol. 140: 2389–2394 (1988).

Ved, H. S., et al., "Regulation of neuronal differentiation in neuron-enriched primary cultures from embryonic rat cerebra by platelet-activating factor and the structurally related glycerol ether lipid, dodecylglycerol", J. Neurosci. Res. 30: 353–358 (1991).

Voelkel, N. F., et al., "Nonimmunological production of leukotrienes induced by platelet-activating factor", Science 218: 286–289 (1982).

Wieraszko, A., et al., "Long-term potentiation in the hippocampus induced by platelet-activating factor", Neuron 10: 553–557 (1993).

Yamanaka, S., et al., "Putative mechanism of hypotensive action of platelet-activating factor in dogs", Circ. Res. 70: 893–901 (1992).

Yasaka, T., et al., "Monocyte aggregation and superoxide anion release in response to formyl-methionyl-leucyl-phenylalanine (FMLP) and platelet-activating factor (PAF)", J. Immunol. 128: 1939–1944 (1982).

Zhou, W. G., et al., "Evidence for platelet-activating factor as a late-phase mediator of chronic pancreatitis in the rat", Am. J. Pathol. 137: 1501–1508 (1990).

Zhu, Y. P., et al., "The presence of platelet-activating factor binding sites in human myometrium and their role in uterine contraction", Am. J. Obstet. Gynecol. 166: 1222–1227 (1992).

What is claimed is:

1. A process for determining whether a chemical compound specifically binds to and activates a mammalian SNORF25 receptor, which comprises contacting cells producing a second messenger response and expressing on their cell surface the mammalian SNORF25 receptor, wherein such cells do not normally express the mammalian SNORF25 receptor, with the chemical compound under conditions suitable for activation of the mammalian SNORF25 receptor, and measuring the second messenger response in the presence and in the absence of the chemical compound, a change in the second messenger response in the presence of the chemical compound indicating that the compound activates the mammalian SNORF25 receptor; wherein (1) the mammalian SNORF25 receptor has an amino acid sequence greater than 95% identical to the amino acid sequence shown in SEQ ID NO: 2 or that encoded by the plasmid pEXJT3T7-hSNORF25 (ATCC Accession No. 203495); or (2) the mammalian SNORF25 receptor has an amino acid sequence greater than 95% identical to the amino acid sequence shown in SEQ ID NO: 4 or that encoded by the plasmid pcDNA3.1-rSNORF25 (ATCC Accession No. 203494); or 3) the mammalian SNORF25 receptor has an amino acid sequence greater than 95% identical to the amino acid sequence shown in SEQ ID NO: 25 or that encoded by the plasmid pEXJ-mSNORF25-f (ATCC Patent Depository No. 2263).

2. The process of claim 1, wherein the second messenger response comprises chloride channel activation and the change in second messenger is an increase in the level of chloride current.

3. The process of claim 1, wherein, the second messenger response comprises change in intracellular calcium levels and the change in second messenger is an increase in the measure of intracellular calcium.

4. The process of claim 1, wherein the second messenger response comprises release of inositol phosphate and the change in second messenger is an increase in the level of inositol phosphate.

5. A process for determining whether a chemical compound specifically binds to and inhibits activation of a mammalian SNORF25 receptor, which comprises separately contacting cells producing a second messenger response and expressing on their cell surface the mammalian SNORF25 receptor, wherein such cells do not normally express the mammalian SNORF25 receptor, with both the chemical compound and a second chemical compound known to activate the mammalian SNORF25 receptor, and with only the second chemical compound, under conditions suitable for activation of the mammalian SNORF25 receptor, and measuring the second messenger response in the presence of only the second chemical compound and in the presence of both the second chemical compound and the chemical compound, a smaller change in the second messenger response in the presence of both the chemical compound and the second chemical compound than in the presence of only the second chemical compound indicating that the chemical compound inhibits activation of the mammalian SNORF25 receptor; wherein (1) the mammalian SNORF25 receptor has an amino acid sequence greater than 95% identical to the amino acid sequence shown in SEQ ID NO: 2 or that encoded by the plasmid pEXJT3T7-hSNORF25 (ATCC Accession No. 203495); or 2) the mammalian SNORF25 receptor has an amino acid sequence greater than 95% identical to the amino acid sequence shown in SEQ ID NO: 4 or that encoded by the plasmid pcDNA3.1-rSNORF25 (ATCC Accession No. 203494); or 3) the mammalian SNORF25 receptor has an amino acid sequence greater than 95% identical to the amino acid sequence shown in SEQ ID NO: 25 or that encoded by the plasmid pEXJ-mSNORF25-f (ATCC Patent Depository No. 2263).

6. The process of claim 5, wherein the second messenger response comprises chloride channel activation and the change in second messenger response is a smaller increase in the level of chloride current in the presence of both the chemical compound and the second chemical compound than in the presence of only the second chemical compound.

7. The process of claim 5, wherein the second messenger response comprises change in intracellular calcium levels and the change in second messenger response is a smaller increase in the measure of intracellular calcium in the presence of both the chemical compound and the second chemical compound than in the presence of only the second chemical compound.

8. The process of claim 5, wherein the second messenger response comprises release of inositol phosphate and the change in second messenger response is a smaller increase in the level of inositol phosphate in the presence of both the chemical compound and the second chemical compound than in the presence of only the second chemical compound.

9. The process of any of claims 1, 2, 3, 4, 5, 6, 7, or 8, wherein the mammalian SNORF25 receptor is a human SNORF25 receptor, a rat SNORF25 receptor, or a mouse SNORF25 receptor.

10. The process of any of claims 1, 2, 3, 4, 5, 6, 7, or 8, wherein the cell is an insect cell.

11. The process of any of claims 1, 2, 3, 4, 5, 6, 7, or 8, wherein the cell is a mammalian cell.

12. The process of claim 11, wherein the mammalian cell is nonneuronal in origin.

13. The process of claim 12, wherein the nonneuronal cell is a COS-7 cell, CHO cell, 293 human embryonic kidney cell, NIH-3T3 cell or LM(tk−) cell.

14. The process of claim 1 or 5, wherein the mammalian SNORF25 receptor is a constitutively active receptor.

* * * * *

(12) INTER PARTES REEXAMINATION CERTIFICATE (922nd)
United States Patent
Bonini et al.

(10) Number: US 7,416,848 C1
(45) Certificate Issued: *Jul. 31, 2014

(54) DNA ENCODING SNORF25 RECEPTOR

(75) Inventors: James A. Bonini, Oakland, NJ (US);
Beth E. Borowsky, Montclair, NJ (US);
Nika Adham, Ridgewood, NJ (US);
Noel Boyle, Cliffside Park, NJ (US);
Thelma O. Thompson, Passaic Park, NJ (US)

(73) Assignee: H. Lundbeck A/S, Copenhagen-Valby (DK)

Reexamination Request:
No. 95/001,246, Oct. 13, 2009

Reexamination Certificate for:
Patent No.: 7,416,848
Issued: Aug. 26, 2008
Appl. No.: 10/278,437
Filed: Oct. 22, 2002

(*) Notice: This patent is subject to a terminal disclaimer.

Related U.S. Application Data

(63) Continuation of application No. 09/641,259, filed on Aug. 17, 2000, now Pat. No. 6,468,756, which is a continuation-in-part of application No. PCT/US00/04413, filed on Feb. 22, 2000, which is a continuation of application No. 09/387,699, filed on Aug. 13, 1999, now Pat. No. 6,221,660, which is a continuation-in-part of application No. 09/255,376, filed on Feb. 22, 1999, now abandoned.

(51) Int. Cl.
*G01N 33/53* (2006.01)
*C07H 21/04* (2006.01)
*C07K 14/705* (2006.01)

(52) U.S. Cl.
USPC ............ 435/7.1; 435/325; 435/354; 435/357; 435/365; 435/7.2; 435/369; 435/361; 435/356; 435/348; 530/350; 536/23.5

(58) Field of Classification Search
None
See application file for complete search history.

(56) References Cited

To view the complete listing of prior art documents cited during the proceeding for Reexamination Control Number 95/001,246, please refer to the USPTO's public Patent Application Information Retrieval (PAIR) system under the Display References tab.

*Primary Examiner* — Bruce Campell

(57) ABSTRACT

This invention provides isolated nucleic acids encoding mammalian SNORF25 receptors, purified mammalian SNORF25 receptors, vectors comprising nucleic acid encoding mammalian SNORF25 receptors, cells comprising such vectors, antibodies directed to mammalian SNORF25 receptors, nucleic acid probes useful for detecting nucleic acid encoding mammalian SNORF25 receptors, antisense oligonucleotides complementary to unique sequences of nucleic acid encoding mammalian SNORF25 receptors, transgenic, nonhuman animals which express DNA encoding normal or mutant mammalian SNORF25 receptors, methods of isolating mammalian SNORF25 receptors, methods of treating an abnormality that is linked to the activity of the mammalian SNORF25 receptors, as well as methods of determining binding of compounds to mammalian SNORF25 receptors, methods of identifying agonists and antagonists of SNORF25 receptors, and agonists and antagonists so identified.

INTER PARTES REEXAMINATION CERTIFICATE ISSUED UNDER 35 U.S.C. 316

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 1, line 3:

This application is a [continuation-in-part] *continuation* of U.S. Ser. No. 09/641,259, filed Aug. 17, 2000, now U.S. Pat. No. 6,458,756, which [claims priority of] *is a continuation-in-part* of PCT International Application Ser. No. PCT/US00/04413, filed Feb. 22, 2000, which [claims priority of] *is a continuation* of U.S. Ser. No. 09/387,699, filed Aug. 13, 1999, now U.S. Pat. No. 6,221,660, issued on Apr. 24, 2001, which is a continuation-in-part of U.S. Ser. No. 09/255,376, filed Feb. 22, 1999, now abandoned, the contents of which are hereby incorporated by reference.

AS A RESULT OF REEXAMINATION, IT HAS BEEN DETERMINED THAT:

Claims 1-20 are cancelled.

\* \* \* \* \*

SEQUENCE LISTING

<160> NUMBER OF SEQ ID NOS: 35

<210> SEQ ID NO 1
<211> LENGTH: 1129
<212> TYPE: DNA
<213> ORGANISM: Homo sapiens

<400> SEQUENCE: 1

```
tgagaatttc agctggagag atagcatgcc ctggtaagtg aagtcctgcc acttcgagac      60
atggaatcat ctttctcatt tggagtgatc cttgctgtcc tggcctccct catcattgct     120
actaacacac tagtggctgt ggctgtgctg ctgttgatcc acaagaatga tggtgtcagt     180
ctctgcttca ccttgaatct ggctgtggct gacaccttga ttggtgtggc catctctggc     240
ctactcacag accagctctc cagcccttct cggcccacac agaagaccct gtgcagcctg     300
cggatggcat ttgtcacttc ctccgcagct gcctctgtcc tcacggtcat gctgatcacc     360
tttgacaggt accttgccat caagcagccc ttccgctact tgaagatcat gagtgggttc     420
gtggccgggg cctgcattgc cgggctgtgg ttagtgtctt acctcattgg cttcctccca     480
ctcggaatcc ccatgttcca gcagactgcc tacaaagggc agtgcagctt ctttgctgta     540
```

-continued

```
tttcaccctc acttcgtgct gaccctctcc tgcgttggct tcttcccagc catgctcctc    600
tttgtcttct tctactgcga catgctcaag attgcctcca tgcacagcca gcagattcga    660
aagatggaac atgcaggagc catggctgga ggttatcgat ccccacggac tcccagcgac    720
ttcaaagctc tccgtactgt gtctgttctc attgggagct tgctctatc ctggaccccc     780 ttccttatca ctggcattgt gcaggtggcc tgccaggagt gtcacctcta cctagtgctg    840
gaacggtacc tgtggctgct cggcgtgggc aactccctgc tcaacccact catctatgcc    900
tattggcaga aggaggtgcg actgcagctc taccacatgg ccctaggagt gaagaaggtg    960
ctcacctcat tcctcctctt tctctcggcc aggaattgtg gcccagagag gcccagggaa    1020
agttcctgtc acatcgtcac tatctccagc tcagagtttg atggctaaga cggtaagggc    1080
agagaagttt caaagtgcct ttctcctccc actctggagc cccaactag               1129
```

<210> SEQ ID NO 2
<211> LENGTH: 335
<212> TYPE: PRT
<213> ORGANISM: Homo sapiens

<400> SEQUENCE: 2

```
Met Glu Ser Ser Phe Ser Phe Gly Val Ile Leu Ala Val Leu Ala Ser
1               5                   10                  15

Leu Ile Ile Ala Thr Asn Thr Leu Val Ala Val Ala Val Leu Leu Leu
            20                  25                  30

Ile His Lys Asn Asp Gly Val Ser Leu Cys Phe Thr Leu Asn Leu Ala
        35                  40                  45

Val Ala Asp Thr Leu Ile Gly Val Ala Ile Ser Gly Leu Leu Thr Asp
    50                  55                  60

Gln Leu Ser Ser Pro Ser Arg Pro Thr Gln Lys Thr Leu Cys Ser Leu
65                  70                  75                  80

Arg Met Ala Phe Val Thr Ser Ser Ala Ala Ala Ser Val Leu Thr Val
                85                  90                  95

Met Leu Ile Thr Phe Asp Arg Tyr Leu Ala Ile Lys Gln Pro Phe Arg
            100                 105                 110

Tyr Leu Lys Ile Met Ser Gly Phe Val Ala Gly Ala Cys Ile Ala Gly
        115                 120                 125

Leu Trp Leu Val Ser Tyr Leu Ile Gly Phe Leu Pro Leu Gly Ile Pro
    130                 135                 140

Met Phe Gln Gln Thr Ala Tyr Lys Gly Gln Cys Ser Phe Phe Ala Val
145                 150                 155                 160

Phe His Pro His Phe Val Leu Thr Leu Ser Cys Val Gly Phe Phe Pro
                165                 170                 175

Ala Met Leu Leu Phe Val Phe Phe Tyr Cys Asp Met Leu Lys Ile Ala
            180                 185                 190

Ser Met His Ser Gln Gln Ile Arg Lys Met Glu His Ala Gly Ala Met
        195                 200                 205

Ala Gly Gly Tyr Arg Ser Pro Arg Thr Pro Ser Asp Phe Lys Ala Leu
    210                 215                 220

Arg Thr Val Ser Val Leu Ile Gly Ser Phe Ala Leu Ser Trp Thr Pro
225                 230                 235                 240

Phe Leu Ile Thr Gly Ile Val Gln Val Ala Cys Gln Glu Cys His Leu
                245                 250                 255

Tyr Leu Val Leu Glu Arg Tyr Leu Trp Leu Leu Gly Val Gly Asn Ser
            260                 265                 270
```

```
Leu Leu Asn Pro Leu Ile Tyr Ala Tyr Trp Gln Lys Glu Val Arg Leu
        275                 280                 285

Gln Leu Tyr His Met Ala Leu Gly Val Lys Lys Val Leu Thr Ser Phe
    290                 295                 300

Leu Leu Phe Leu Ser Ala Arg Asn Cys Gly Pro Glu Arg Pro Arg Glu
305                 310                 315                 320

Ser Ser Cys His Ile Val Thr Ile Ser Ser Glu Phe Asp Gly
            325                 330                 335

<210> SEQ ID NO 3
<211> LENGTH: 1082
<212> TYPE: DNA
<213> ORGANISM: Rattus norvegicus

<400> SEQUENCE: 3
tcaagaccca gcatgccctt ataagtggga gtcctgctac ctcgaaccat ggagtcatct      60
ttctcatttg gagtgatcct tgctgtcctg accatcctta tcattgctgt taatgcgctg    120
gtggttgtgg ctatgctgct atcaatctac aagaatgatg gtgttggcct ttgcttcacc    180
ttaaatctgg ccgtggctga taccttgatt ggcgtggcta tttctgggct agttacagac    240
cagctctcca gctctgctca gcacacacag aagaccttgt gtagccttcg gatggcattc    300
gtcacttctt ctgcagccgc ctctgtcctc acgtcatgc tgattgcctt tgacaggtac    360
ctggccatta gcagcccct ccgttacttc agatcatga atgggcttgt agccggagga    420
tgcattgcag gctgtggtt gatatcttac cttatcggct cctcccact ggagtctcc     480
atattccagc agaccaccta ccatgggccc tgcaccttct tgctgtgtt tcacccaagg    540
tttgtgctga ccctctcctg tgctggcttc ttcccagctg tgctcctctt tgtcttcttc    600
tactgtgaca tgctcaagat tgcctctgtg cacagccagc acatccggaa gatggaacat    660
gcaggagcca tggttggagc ttgccggccc ccacggcctg tcaatgactt caaggctgtc    720
cggactgtat ctgtccttat gggagcttcc accctgtcct ggtctccgtt ctctcatcact    780
agcattgtgc aggtggcctg ccacaaatgc tgcctctacc aagtgctgga aaaatacctc    840
tggctccttg gagttggcaa ctccctgctc aacccactca tctatgccta ttggcagagg    900
gaggttcggc agcagctctg ccacatggcc ctggggtga agaagttctt tacttcaatc    960
ttcctccttc tctcggccag gaatcgtggt ccacagagga cccgagaaag ctcctatcac   1020
atcgtcacta tcagccagcc ggagctcgat ggctaggatg gtaaggaatg gatgtttcca   1080
ag                                                                  1082

<210> SEQ ID NO 4
<211> LENGTH: 335
<212> TYPE: PRT
<213> ORGANISM: Rattus norvegicus

<400> SEQUENCE: 4

Met Glu Ser Ser Phe Ser Phe Gly Val Ile Leu Ala Val Leu Thr Ile
1               5                   10                  15

Leu Ile Ile Ala Val Asn Ala Leu Val Val Val Ala Met Leu Leu Ser
            20                  25                  30

Ile Tyr Lys Asn Asp Gly Val Gly Leu Cys Phe Thr Leu Asn Leu Ala
        35                  40                  45

Val Ala Asp Thr Leu Ile Gly Val Ala Ile Ser Gly Leu Val Thr Asp
    50                  55                  60
```

```
Gln Leu Ser Ser Ser Ala Gln His Thr Gln Lys Thr Leu Cys Ser Leu
 65                  70                  75                  80

Arg Met Ala Phe Val Thr Ser Ser Ala Ala Ala Ser Val Leu Thr Val
                 85                  90                  95

Met Leu Ile Ala Phe Asp Arg Tyr Leu Ala Ile Lys Gln Pro Leu Arg
            100                 105                 110

Tyr Phe Gln Ile Met Asn Gly Leu Val Ala Gly Gly Cys Ile Ala Gly
        115                 120                 125

Leu Trp Leu Ile Ser Tyr Leu Ile Gly Phe Leu Pro Leu Gly Val Ser
130                 135                 140

Ile Phe Gln Gln Thr Thr Tyr His Gly Pro Cys Thr Phe Phe Ala Val
145                 150                 155                 160

Phe His Pro Arg Phe Val Leu Thr Leu Ser Cys Ala Gly Phe Phe Pro
                165                 170                 175

Ala Val Leu Leu Phe Val Phe Phe Tyr Cys Asp Met Leu Lys Ile Ala
            180                 185                 190

Ser Val His Ser Gln His Ile Arg Lys Met Glu His Ala Gly Ala Met
        195                 200                 205

Val Gly Ala Cys Arg Pro Pro Arg Pro Val Asn Asp Phe Lys Ala Val
    210                 215                 220

Arg Thr Val Ser Val Leu Ile Gly Ser Phe Thr Leu Ser Trp Ser Pro
225                 230                 235                 240

Phe Leu Ile Thr Ser Ile Val Gln Val Ala Cys His Lys Cys Cys Leu
                245                 250                 255

Tyr Gln Val Leu Glu Lys Tyr Leu Trp Leu Leu Gly Val Gly Asn Ser
            260                 265                 270

Leu Leu Asn Pro Leu Ile Tyr Ala Tyr Trp Gln Arg Glu Val Arg Gln
        275                 280                 285

Gln Leu Cys His Met Ala Leu Gly Val Lys Lys Phe Phe Thr Ser Ile
    290                 295                 300

Phe Leu Leu Leu Ser Ala Arg Asn Arg Gly Pro Gln Arg Thr Arg Glu
305                 310                 315                 320

Ser Ser Tyr His Ile Val Thr Ile Ser Gln Pro Glu Leu Asp Gly
                325                 330                 335

<210> SEQ ID NO 5
<211> LENGTH: 21
<212> TYPE: DNA
<213> ORGANISM: Artificial Sequence
<220> FEATURE:
<223> OTHER INFORMATION: Primer/ Probe
<220> FEATURE:
<221> NAME/KEY: misc_feature
<222> LOCATION: (1)..(21)
<223> OTHER INFORMATION: n=inosine

<400> SEQUENCE: 5
tbdsyvynga ymgntayvtk g                                           21

<210> SEQ ID NO 6
<211> LENGTH: 26
<212> TYPE: DNA
<213> ORGANISM: Artificial Sequence
<220> FEATURE:
<223> OTHER INFORMATION: Primer/ Probe
<220> FEATURE:
<221> NAME/KEY: misc_feature
<222> LOCATION: (1)..(26)
<223> OTHER INFORMATION: n=inosine
```

```
<400> SEQUENCE: 6
ganrsnarng mrtanaynak nggrtt                                    26

<210> SEQ ID NO 7
<211> LENGTH: 25
<212> TYPE: DNA
<213> ORGANISM: Artificial Sequence
<220> FEATURE:
<223> OTHER INFORMATION: Primer/ Probe

<400> SEQUENCE: 7
ttatgcttcc ggctcgtatg ttgtg                                     25

<210> SEQ ID NO 8
<211> LENGTH: 27
<212> TYPE: DNA
<213> ORGANISM: Artificial Sequence
<220> FEATURE:
<223> OTHER INFORMATION: Primer/ Probe

<400> SEQUENCE: 8
atgtgctgca aggcgattta agttggg                                   27

<210> SEQ ID NO 9
<211> LENGTH: 20
<212> TYPE: DNA
<213> ORGANISM: Artificial Sequence
<220> FEATURE:
<223> OTHER INFORMATION: Primer/ Probe

<400> SEQUENCE: 9
tggtctgctg gaatatggag                                           20

<210> SEQ ID NO 10
<211> LENGTH: 25
<212> TYPE: DNA
<213> ORGANISM: Artificial Sequence
<220> FEATURE:
<223> OTHER INFORMATION: Primer/ Probe

<400> SEQUENCE: 10
cttgggtgaa acacagcaaa gaagg                                     25

<210> SEQ ID NO 11
<211> LENGTH: 26
<212> TYPE: DNA
<213> ORGANISM: Artificial Sequence
<220> FEATURE:
<223> OTHER INFORMATION: Primer/ Probe

<400> SEQUENCE: 11
atggaacatg caggagccat ggttgg                                    26

<210> SEQ ID NO 12
<211> LENGTH: 24
<212> TYPE: DNA
<213> ORGANISM: Artificial Sequence
<220> FEATURE:
<223> OTHER INFORMATION: Primer/ Probe

<400> SEQUENCE: 12
aagacaaaga ggagcacagc tggg                                      24
```

<210> SEQ ID NO 13
<211> LENGTH: 24
<212> TYPE: DNA
<213> ORGANISM: Artificial Sequence
<220> FEATURE:
<223> OTHER INFORMATION: Primer/ Probe

<400> SEQUENCE: 13
gctcaagatt gcctctgtgc acag                                            24

<210> SEQ ID NO 14
<211> LENGTH: 35
<212> TYPE: DNA
<213> ORGANISM: Artificial Sequence
<220> FEATURE:
<223> OTHER INFORMATION: Primer/ Probe

<400> SEQUENCE: 14
atctataagc ttaggcactt ggaaacatcc attcc                                35

<210> SEQ ID NO 15
<211> LENGTH: 36
<212> TYPE: DNA
<213> ORGANISM: Artificial Sequence
<220> FEATURE:
<223> OTHER INFORMATION: Primer/ Probe

<400> SEQUENCE: 15
atctatggat cctgtgagaa tctgagctca agaccc                               36

<210> SEQ ID NO 16
<211> LENGTH: 58
<212> TYPE: DNA
<213> ORGANISM: Artificial Sequence
<220> FEATURE:
<223> OTHER INFORMATION: Primer/ Probe

<400> SEQUENCE: 16
ttcaccttaa atctggccgt ggctgatacc ttgattggcg tggctatttc tgggctag       58

<210> SEQ ID NO 17
<211> LENGTH: 61
<212> TYPE: DNA
<213> ORGANISM: Artificial Sequence
<220> FEATURE:
<223> OTHER INFORMATION: Primer/ Probe

<400> SEQUENCE: 17
gctgtgtttc acccaaggtt tgtgctgacc ctctcctgtg ctggcttctt cccagctgtg     60
c                                                                     61

<210> SEQ ID NO 18
<211> LENGTH: 22
<212> TYPE: DNA
<213> ORGANISM: Artificial Sequence
<220> FEATURE:
<223> OTHER INFORMATION: Primer/ Probe

<400> SEQUENCE: 18
cctctaccta gtgctggaac gg                                              22

<210> SEQ ID NO 19
<211> LENGTH: 18
<212> TYPE: DNA
<213> ORGANISM: Artificial Sequence

```
<220> FEATURE:
<223> OTHER INFORMATION: Primer/ Probe

<400> SEQUENCE: 19
gctgcagtcg caccctcct                                                    18

<210> SEQ ID NO 20
<211> LENGTH: 31
<212> TYPE: DNA
<213> ORGANISM: Artificial Sequence
<220> FEATURE:
<223> OTHER INFORMATION: Primer/ Probe

<400> SEQUENCE: 20
tccctgctca acccactcat ctatgcctat t                                      31

<210> SEQ ID NO 21
<211> LENGTH: 19
<212> TYPE: DNA
<213> ORGANISM: Artificial Sequence
<220> FEATURE:
<223> OTHER INFORMATION: Primer/ Probe

<400> SEQUENCE: 21
gtgtagcctt cggatggca                                                    19

<210> SEQ ID NO 22
<211> LENGTH: 21
<212> TYPE: DNA
<213> ORGANISM: Artificial Sequence
<220> FEATURE:
<223> OTHER INFORMATION: Primer/ Probe

<400> SEQUENCE: 22
ggctgcttaa tggccaggta c                                                 21

<210> SEQ ID NO 23
<211> LENGTH: 26
<212> TYPE: DNA
<213> ORGANISM: Artificial Sequence
<220> FEATURE:
<223> OTHER INFORMATION: Primer/ Probe

<400> SEQUENCE: 23
tcctcacggt catgctgatt gccttt                                            26

<210> SEQ ID NO 24
<211> LENGTH: 1056
<212> TYPE: DNA
<213> ORGANISM: mus sp.

<400> SEQUENCE: 24
agtggaagtg ctgctacctc accatggagt catccttctc atttggagtg atccttgctg        60
tcctaaccat cctcatcatt gctgttaatg cactggtagt tgtggctatg ctgctatcaa       120
tctacaagaa tgatggtgtt ggcctttgct tcaccttgaa tctggccgtg gctgatacct       180
tgattggcgt ggctatttct ggtctagtta cagaccagct ctccagctct gctcagcata       240
cacagaagac cttgtgtagc cttcggatgg catttgtcac ttcttctgca gctgcctctg       300
tcctcacggt catgctgatt gcctttgaca gataccttgc cattaagcag cccctccgtt       360
acttccagat catgaatggg cttgtggctg gagcatgcat tgcaggactg tggttggtat       420
cttaccttat cggcttcctc ccactcggag tctccatatt ccagcagacc acctaccatg       480
```

```
gaccctgcag cttctttgct gtgtttcacc caaggtttgt gctgaccctc tcctgtgctg    540
gcttcttccc agctgtgctc ctctttgtct tcttctactg tgacatgctc aagattgcct    600
ctgtgcacag ccagcagatc cggaagatgg aacatgcagg agccatggcc ggagcttatc    660
ggcccccacg gtctgtcaat gacttcaagg ctgttcgtac tatagctgtt cttattggga    720
gcttcactct gtcctggtct cccttttctca taactagcat tgtgcaggtg gcctgccaca    780
aatgctgcct ttaccaagtg ctggaaaagt acctgtggct ccttggagtt ggcaactccc    840
tactcaaccc actcatctat gcctattggc agagggaggt tcggcagcag ctctaccaca    900
tggccctggg agtgaaaaag ttcttcactt caatcctcct ccttctccca gccaggaatc    960
gtggtccaga gaggaccaga gaaagcgcct atcacatcgt cactatcagc catccggagc   1020
tcgatggcta agacggtaag gaaggaatgt ttcaaa                              1056
```

<210> SEQ ID NO 25
<211> LENGTH: 335
<212> TYPE: PRT
<213> ORGANISM: mus sp.

<400> SEQUENCE: 25

```
Met Glu Ser Ser Phe Ser Phe Gly Val Ile Leu Ala Val Leu Thr Ile
1               5                   10                  15

Leu Ile Ile Ala Val Asn Ala Leu Val Val Ala Met Leu Leu Ser
            20                  25                  30

Ile Tyr Lys Asn Asp Gly Val Gly Leu Cys Phe Thr Leu Asn Leu Ala
        35                  40                  45

Val Ala Asp Thr Leu Ile Gly Val Ala Ile Ser Gly Leu Val Thr Asp
    50                  55                  60

Gln Leu Ser Ser Ser Ala Gln His Thr Gln Lys Thr Leu Cys Ser Leu
65                  70                  75                  80

Arg Met Ala Phe Val Thr Ser Ser Ala Ala Ser Val Leu Thr Val
                85                  90                  95

Met Leu Ile Ala Phe Asp Arg Tyr Leu Ala Ile Lys Gln Pro Leu Arg
            100                 105                 110

Tyr Phe Gln Ile Met Asn Gly Leu Val Ala Gly Ala Cys Ile Ala Gly
        115                 120                 125

Leu Trp Leu Val Ser Tyr Leu Ile Gly Phe Leu Pro Leu Gly Val Ser
    130                 135                 140

Ile Phe Gln Gln Thr Thr Tyr His Gly Pro Cys Ser Phe Phe Ala Val
145                 150                 155                 160

Phe His Pro Arg Phe Val Leu Thr Leu Ser Cys Ala Gly Phe Pro
                165                 170                 175

Ala Val Leu Leu Phe Val Phe Phe Tyr Cys Asp Met Leu Lys Ile Ala
            180                 185                 190

Ser Val His Ser Gln Gln Ile Arg Lys Met Glu His Ala Gly Ala Met
        195                 200                 205

Ala Gly Ala Tyr Arg Pro Pro Arg Ser Val Asn Asp Phe Lys Ala Val
    210                 215                 220

Arg Thr Ile Ala Val Leu Ile Gly Ser Phe Thr Leu Ser Trp Ser Pro
225                 230                 235                 240

Phe Leu Ile Thr Ser Ile Val Gln Val Ala Cys His Lys Cys Cys Leu
                245                 250                 255

Tyr Gln Val Leu Glu Lys Tyr Leu Trp Leu Leu Gly Val Gly Asn Ser
            260                 265                 270
```

```
Leu Leu Asn Pro Leu Ile Tyr Ala Tyr Trp Gln Arg Glu Val Arg Gln
        275                 280                 285

Gln Leu Tyr His Met Ala Leu Gly Val Lys Lys Phe Phe Thr Ser Ile
    290                 295                 300

Leu Leu Leu Leu Pro Ala Arg Asn Arg Gly Pro Glu Arg Thr Arg Glu
305                 310                 315                 320

Ser Ala Tyr His Ile Val Thr Ile Ser His Pro Glu Leu Asp Gly
            325                 330                 335

<210> SEQ ID NO 26
<211> LENGTH: 26
<212> TYPE: DNA
<213> ORGANISM: Artificial Sequence
<220> FEATURE:
<223> OTHER INFORMATION: Primer/ Probe

<400> SEQUENCE: 26
ctcatttgga gtgatccttg ctgtcc                                    26

<210> SEQ ID NO 27
<211> LENGTH: 25
<212> TYPE: DNA
<213> ORGANISM: Artificial Sequence
<220> FEATURE:
<223> OTHER INFORMATION: Primer/ Probe

<400> SEQUENCE: 27
acatgagtgg gttgagcagg gagtt                                     25

<210> SEQ ID NO 28
<211> LENGTH: 51
<212> TYPE: DNA
<213> ORGANISM: Artificial Sequence
<220> FEATURE:
<223> OTHER INFORMATION: Primer/ Probe

<400> SEQUENCE: 28
gaagaccttg tgtagccttc ggatggcatt tgtcacttct tctgcagctg c         51

<210> SEQ ID NO 29
<211> LENGTH: 20
<212> TYPE: DNA
<213> ORGANISM: Artificial Sequence
<220> FEATURE:
<223> OTHER INFORMATION: Primer/ Probe

<400> SEQUENCE: 29
cctcaccgtc atgctgattg                                           20

<210> SEQ ID NO 30
<211> LENGTH: 19
<212> TYPE: DNA
<213> ORGANISM: Artificial Sequence
<220> FEATURE:
<223> OTHER INFORMATION: Primer/ Probe

<400> SEQUENCE: 30
caatgcatgc tccagccac                                            19

<210> SEQ ID NO 31
<211> LENGTH: 25
<212> TYPE: DNA
<213> ORGANISM: Artificial Sequence
<220> FEATURE:
<223> OTHER INFORMATION: Primer/ Probe
```

```
<400> SEQUENCE: 31
ttgccattaa gcagccctc cgtta                                          25

<210> SEQ ID NO 32
<211> LENGTH: 25
<212> TYPE: DNA
<213> ORGANISM: Artificial Sequence
<220> FEATURE:
<223> OTHER INFORMATION: Primer/ Probe

<400> SEQUENCE: 32
catccagcat gcctttgtaa gtgga                                         25

<210> SEQ ID NO 33
<211> LENGTH: 25
<212> TYPE: DNA
<213> ORGANISM: Artificial Sequence
<220> FEATURE:
<223> OTHER INFORMATION: primer/probe

<400> SEQUENCE: 33
aatcagcatg acggtgagga cagag                                         25

<210> SEQ ID NO 34
<211> LENGTH: 23
<212> TYPE: DNA
<213> ORGANISM: Artificial Sequence
<220> FEATURE:
<223> OTHER INFORMATION: Primer/ Probe

<400> SEQUENCE: 34
cggcagcagc tctaccacat ggc                                           23

<210> SEQ ID NO 35
<211> LENGTH: 26
<212> TYPE: DNA
<213> ORGANISM: Artificial Sequence
<220> FEATURE:
<223> OTHER INFORMATION: Primer/ Probe

<400> SEQUENCE: 35
caaacaccct ttcagcagta tactcc                                        26
```